(12) United States Patent
Sundaresan et al.

(10) Patent No.: US 8,039,463 B2
(45) Date of Patent: Oct. 18, 2011

(54) PIPERAZINE DERIVATIVES AS INHIBITORS OF STEAROYL-COA DESATURASE

(75) Inventors: Kumar Sundaresan, Tamilnadu (IN); Sandeep N. Raikar, Karwar (IN); Srinivasa Raju Sammeta, Andhra Pradesh (IN); Ganesh Prabhu, Shimoga (IN); Hosahalli Subramanya, Karnataka (IN); Alexander Bischoff, Smithtown, NY (US)

(73) Assignee: Forest Laboratories Holdings Limited, Hamilton (BM)

( * ) Notice: Subject to any disclaimer, the term of this patent is extended or adjusted under 35 U.S.C. 154(b) by 256 days.

(21) Appl. No.: 12/408,367

(22) Filed: Mar. 20, 2009

(65) Prior Publication Data
US 2009/0239848 A1 Sep. 24, 2009

Related U.S. Application Data

(60) Provisional application No. 61/049,474, filed on May 1, 2008.

(30) Foreign Application Priority Data

Mar. 20, 2008 (IN) .............................. 574/KOL/2008

(51) Int. Cl.
| | |
|---|---|
| A61K 31/551 | (2006.01) |
| A61K 31/495 | (2006.01) |
| A61K 31/496 | (2006.01) |
| C07D 295/192 | (2006.01) |
| C07D 213/75 | (2006.01) |
| C07D 231/40 | (2006.01) |
| C07D 261/14 | (2006.01) |
| C07D 263/58 | (2006.01) |
| C07D 271/106 | (2006.01) |
| C07D 271/10 | (2006.01) |
| C07D 277/46 | (2006.01) |
| C07D 333/24 | (2006.01) |

(52) U.S. Cl. .............. 514/218; 514/253.01; 514/254.02; 514/254.03; 514/254.05; 514/255.01; 540/575; 544/360; 544/367; 544/368; 544/369; 544/379; 544/387; 544/371; 544/121; 544/383

(58) Field of Classification Search .................. None
See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 2006/0241121 | A1 | 10/2006 | Greenlee et al. |
| 2006/0252767 | A1 | 11/2006 | Sviridov et al. |

FOREIGN PATENT DOCUMENTS

| | | |
|---|---|---|
| EP | 0433662 A2 | 6/1991 |
| WO | WO0162954 A2 | 8/2001 |
| WO | WO0226944 A2 | 4/2002 |

OTHER PUBLICATIONS

Dobrzyn et al.Drug Discovery Today: Therapeutic Strategies, vol. 2, p. 125-128 (2005).*
Vippagunta et al Advanced Drug Delivery Reviews, vol. 48, pp. 3-26 (2001).*
International Search Report for PCT/US2009/037807, mailed Jul. 2, 2009.
Written Opinion of the International Searching Authority for PCT/US2009/037807, mailed Jul. 2, 2009.
Dobrzyn, Agnieszka, et al., Inhibition of Stearoyl-CoA Desaturase by Cyclic Amine Derivatives, Expert Opin. Ther. Patents, 18(4):457-460, 2008.
Xin, Zhili, et al., Discovery of Piperidine-aryl Urea-based Stearoyl-CoA Desaturase 1 Inhibitors, Bioorganic & Medicinal Chemistry Letters 18, 4298-4302, 2008.
Dean, D., Editor, Recent Advances in the Synthesis and Applications of Radiolabeled Compounds for Drug Discovery and Development, vol. 6, No. 10, pp. i-i(1), 2000.
Lindqvuist, Y., et al., Crystal Structure of Δ9 Stearoyl-acyl Carrier Protein Desaturase From Castor Seed and its Relationship to Other Di-iron Proteins, The EMBO Journal, vol. 15, No. 16, pp. 4081-4092, 1996.
de Antueno, RJ, et al., Relationship Between Mouse Liver Delta 9 Desaturase Activity and Plasma Lipds, Lipids, vol. 28, No. 4, pp. 285-290, 1993.
Kabalka, GW, The Synthesis of Radiolabeled Compounds via Organometallic Intermediates, Tetrahedron, vol. 45, No. 21, pp. 6601-6621, 1989.
Jeffcoat, R., et al., Numa, S., Editor, The Regulation of Desaturation and Elongation of Fatty Acids in Mammals, Fatty Acid Metabolism and its Regulation, pp. 84-112, 1984.
Evans, EA, Synthesis of Radiolabelled Compounds, Journal of Radioanalytical and Nuclear Chemistry, vol. 64, Nos. 1-2, pp. 9-32, 1981.

* cited by examiner

*Primary Examiner* — Emily Bernhardt
(74) *Attorney, Agent, or Firm* — Charles Ryan; Michael Ciraolo; and Hemant Khanna

(57) ABSTRACT

The present invention relates to piperazine derivatives that act as inhibitors of stearoyl-CoA desaturase. The invention also relates to methods of preparing the compounds, compositions containing the compounds, and to methods of treatment using the compounds.

10 Claims, No Drawings

PIPERAZINE DERIVATIVES AS INHIBITORS OF STEAROYL-COA DESATURASE

CROSS-REFERENCE TO RELATED APPLICATIONS

This application claims priority to U.S. Provisional Patent Application 61/049,474, which was filed on May 1, 2008; and to Indian Patent Application 574/KOL/2008, which was filed on Mar. 20, 2008.

FIELD OF THE INVENTION

The present invention relates to piperazine derivatives that act as inhibitors of stearoyl-CoA desaturase. The invention also relates to methods of preparing the compounds, compositions containing the compounds, and to methods of treatment using the compounds.

BACKGROUND OF THE INVENTION

Metabolic syndrome has become one of the leading health problems in the world. As a component of metabolic syndrome, obesity also has causal roles in other components of the syndrome, including insulin resistance, dyslipidemia, and cardiovascular diseases. Effective treatments for metabolic syndrome in general and obesity in particular have been lacking. Effective therapies for the treatment of obesity, a key element of metabolic syndrome, are urgently needed.

A number of mammalian stearoyl-coenzyme A desaturase (SCD) genes have been cloned. For example, two genes have been cloned from rat (SCD1, SCD2) and four SCD genes have been isolated from mouse (SCD1, 2, 3, and 4). While the basic biochemical role of SCD has been known in rats and mice since the 1970's (see, e.g., Jeffcoat, R. et al., Elsevier Science, Vol. 4, pp. 85-112, 1984; de Antueno, R J, Lipids, Vol. 28, No. 4, pp. 285-290, 1993), it has only recently been directly implicated in human disease processes.

A single SCD gene, stearoyl-coenzyme A desaturase-1 (SCD1) has been characterized in humans. SCD1 is described in, e.g., International Publication No. application, WO 01/62954. A second human SCD isoform has recently been identified, and because it bears little sequence homology to alternate mouse or rat isoforms it has been named human SCD5 or hSCD5 (see, e.g., International Publication No. WO 02/26944).

SCD1 catalyzes conversion of saturated fatty acids, stearoyl-CoA and palmitoyl-CoA, to monounsaturated fatty acids, oleoyl-CoA and pamitoleoyl-CoA, respectively. These fatty acids are components of membrane phospholipids, triglycerides, and cholesterol esters. Changes in SCD activity ultimately change membrane fluidity, lipoprotein metabolism, and adiposity. SCD1 inhibition can lead to decreased adiposity and thus be a potential therapy for metabolic syndrome.

Since obesity is becoming increasingly prevalent worldwide, much effort is being devoted to understanding its pathogenesis and treatment. In recent years, several candidate genes have been proposed as therapeutic targets. However, stearoyl-CoA desaturase 1 is of special significance, because it is the major gene target of leptin—a central mediator of energy homeostasis. There is evidence that SCD1 deficiency activates metabolic pathways that promote b-oxidation and decrease lipogenesis in liver and skeletal muscles. One mechanism is via increased activation of AMP-activated protein kinase. SCD1 mutation results also in global changes in expression of genes involved in lipid metabolism. SCD1 deficient mice have increased energy expenditure, reduced body adiposity, and are resistant to diet-induced obesity.

Thus, SCD1 inhibition represents a new and important target for the treatment of various disorders such as obesity and related metabolic disorders. Accordingly, there is a need in the art for derivatives that act as inhibitors of stearoyl-CoA desaturase, such as SCD1.

SUMMARY OF THE INVENTION

The present invention relates to piperazine derivatives that act as inhibitors of stearoyl-CoA desaturase. The invention also relates to methods of preparing the compounds, compositions containing the compounds, and to methods of treatment using the compounds.

DETAILED DESCRIPTION OF THE INVENTION

In one aspect, the present invention includes compounds of the formula:

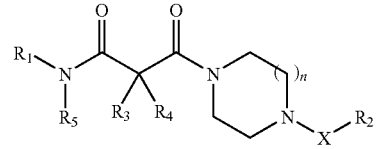

wherein n is 1 or 2;

$R^1$ is aryl, heterocycloalkane, heteroaryl or heterocycle;

$R^2$ is aryl, heteroaryl or heterocycle;

$R^3$ and $R^4$ are each independently hydrogen, halogen or alkyl; or $R^3$ and $R^4$, together with the carbon atom to which they are attached, form a cycloalkyl group;

$R^5$ is hydrogen or alkyl;

wherein when n is 1, then X is —C(O)—, —S(O)$_2$—, or —S(O)—, and when n is 2, then X is —C(O)—, —S(O)$_2$—, —S(O)— or —CR$^6$R$^7$— where R$^6$ and R$^7$ are each independently hydrogen or alkyl;

wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, —O—C(O)—NH—, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;

and pharmaceutically acceptable salts, solvates, hydrates, or solvates of pharmaceutically acceptable salts thereof.

In another aspect, the present invention includes compounds of the formula:

![Structure with R1-N(R5)-C(O)-C(R3)(R4)-C(O)-N(piperazine)n-N-X-R2]

wherein
n is 1 or 2;
$R^1$ is aryl, heteroaryl or heterocycle;
$R^2$ is aryl, heteroaryl or heterocycle;
$R^3$ and $R^4$ are each independently hydrogen, halogen or alkyl; or $R^3$ and $R^4$, together with the carbon atom to which they are attached, form a cycloalkyl group;
$R^5$ is hydrogen or alkyl;
X is —C(O)—, —S(O)$_2$—, —S(O)— or —CR$^6$R$^7$— where $R^6$ and $R^7$ are each independently hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, —O—C(O)—NH—, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, or solvates of pharmaceutically acceptable salts thereof;
with the proviso that said compound is not N-[2,6-bis(1-methylethyl)phenyl]-β-oxo-4-(phenylmethyl)-1-piperazinepropanamide, or a pharmaceutically acceptable salt thereof.

In another aspect, the present invention includes compounds of the formula:

![Structure with R1-N(R5)-C(O)-C(R3)(R4)-C(O)-N(piperazine)n-N-X-R2]

wherein
n is 1;
$R^1$ is aryl, heteroaryl or heterocycle;
$R^2$ is aryl, heteroaryl or heterocycle;
$R^3$ and $R^4$ are each independently hydrogen, halogen or alkyl; or
$R^3$ and $R^4$, together with the carbon atom to which they are attached, form a cycloalkyl group;
$R^5$ is hydrogen or alkyl;
X is —C(O)—, —S(O)$_2$—, or —S(O)—;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, —O—C(O)—NH—, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, or solvates of pharmaceutically acceptable salts thereof.

In another aspect, the present invention includes compounds of the formula:

![Structure with R1-N(R5)-C(O)-C(R3)(R4)-C(O)-N(piperazine)n-N-X-R2]

wherein
n is 1;
$R^1$ is aryl, heteroaryl or heterocycle;
$R^2$ is aryl, heteroaryl or heterocycle;
$R^3$ and $R^4$ are each independently hydrogen, halogen or alkyl; or
$R^3$ and $R^4$, together with the carbon atom to which they are attached, form a cycloalkyl group;
$R^5$ is hydrogen or alkyl;
X is —C(O)—, —S(O)$_2$—, —S(O)— or —CR$^6$R$^7$— where $R^6$ and $R^7$ are each independently hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, —O—C(O)—NH—, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, or solvates of pharmaceutically acceptable salts thereof;
with the proviso that said compound is not N-[2,6-bis(1-methylethyl)phenyl]-β-oxo-4-(phenylmethyl)-1-piperazinepropanamide, or a pharmaceutically acceptable salt thereof.

In other embodiments, a compound is provided having the formula:

![Structure with R1-N(R5)-C(O)-C(H)(H)-C(O)-N(piperazine)n-N-C(O)-R2]

wherein
n is 1 or 2;
$R^1$ is aryl, heterocycloalkane, heteroaryl or heterocycle;
$R^2$ is aryl, heterocycloalkyl, heteroaryl or heterocycle;
$R^5$ is hydrogen or alkyl;

wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, —O—C(O)—NH—, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;

and pharmaceutically acceptable salts, solvates, hydrates, or solvates of pharmaceutically acceptable salts thereof.

In some embodiments, $R^1$ is aryl or heteroaryl, $R^2$ is aryl, $R^5$ is hydrogen, $R^3$ and $R^4$ are each hydrogen or halogen, or $R^3$ and $R^4$, together with the carbon atom to which they are attached form a cycloalkyl group (e.g., $C_3$-$C_6$ cycloalkyl), and X is —C(O)—, —S(O)$_2$— or —CR$^6$R$^7$— where $R^6$ and $R^7$ are each hydrogen.

In some embodiments, $R^1$ is aryl or heteroaryl, $R^2$ is aryl, $R^5$ is hydrogen, $R^3$ and $R^4$ are each hydrogen or halogen, or $R^3$ and $R^4$, together with the carbon atom to which they are attached form a cycloalkyl group (e.g., $C_3$-$C_6$ cycloalkyl), and X is —C(O)—, —S(O)$_2$— or —CR$^6$R$^7$— where $R^6$ and $R^7$ are each hydrogen.

In some embodiments, $R^1$ is optionally substituted aryl (e.g., phenyl), heterocycloalkanyl (e.g., pentyl, hexyl, or heptyl), or heteroaryl (e.g., pyridinyl, thiazolyl). For example, $R^1$ is aryl (e.g., phenyl) or heteroaryl (e.g., pyridinyl, thiazolyl) optionally substituted by one or more aryl (e.g., phenyl), heteroaryl (e.g., oxadiazolyl, methyloxadiazolyl), heterocycle (e.g., piperidinyl), arylalkyloxy (e.g., benzyloxy), alkylamido (e.g., —C(O)NH(CH$_3$)), arylamino (e.g., phenylamino) or —O—C(O)—NH—. For example, $R^1$ may be biphenyl (e.g., 4-biphenyl, 3-biphenyl), (phenyl)pyridinyl (e.g., 5-phenyl-pyridin-2-yl, 6-phenyl-pyridin-3-yl), (oxadiazolyl)phenyl (e.g., [1,2,4]oxadiazol-3-yl-phenyl), (methyloxadiazolyl)phenyl (e.g., 5-methyl[1,3,4]oxadiazol-2-yl-phenyl), benzyloxypyridinyl (e.g., 6-benzyloxy-pyridin-3-yl, 5-benzyloxy-pyridin-2-yl), oxodihydrobenzooxazolyl (e.g., 2-oxo-2,3-dihydro-benzooxazol-5-yl), methylamidophenyl, piperidinylphenyl (e.g., 4-piperidin-1-ylphenyl), phenylthiazolyl (e.g., 4-phenyl-thiazol-2-yl) or (phenylamino)phenyl (e.g., 5-phenylamino-phenyl).

In additional embodiments, $R^2$ is optionally substituted aryl (e.g., phenyl). For example, $R^2$ is aryl (e.g., phenyl) optionally substituted by one or more (such as two or more, or even three or more) halogen (e.g., F, Cl, Br), alkyl (e.g., methyl) or halogenated alkyl (e.g., CF$_3$). For example, $R^2$ is trifluoromethylphenyl (e.g., 2-trifluoromethylphenyl), dichlorophenyl (e.g., 2,5-dichlorophenyl), (trifluoromethyl) fluorophenyl (e.g., 5-fluoro-2-trifluoromethylphenyl), (chloro)difluorophenyl (e.g., 4-chloro-2,5-difluorophenyl), methylphenyl (e.g., 2-methylphenyl), difluorophenyl (e.g., 2,5-difluorophenyl), (bromo)fluorophenyl (e.g., 2-bromo-5-fluorophenyl), trifluorophenyl (e.g., 3,4,5-trifluorophenyl), (chloro)trifluoromethylphenyl (e.g., 2-chloro-5-trifluoromethylphenyl), bromophenyl (e.g., 2-bromophenyl), dichlorofluorophenyl (e.g., 2,4-dichloro-5-fluorophenyl), or fluorophenyl (e.g., 2-fluorophenyl, 3-fluorophenyl, 4-fluorophenyl).

In certain embodiments, X is —C(O)—, —S(O)$_2$— or —CR$^6$R$^7$— where $R^6$ and $R^7$ are each independently hydrogen or alkyl. For example, X is —C(O)—, —S(O)$_2$— or —CH$_2$—. In other embodiments, X is —C(O)—, —S(O)—, or —S(O)$_2$—

In certain embodiments, $R^3$ and $R^4$ are each independently hydrogen, halogen (e.g., F, Cl, Br) or alkyl (e.g., methyl). In other embodiments, $R^3$ and $R^4$ are hydrogen or alkyl (e.g., methyl). In other embodiments, $R^3$ and $R^4$ are hydrogen or halogen (e.g., F). In one embodiment, $R^3$ and $R^4$ are hydrogen. In further embodiments, $R^3$ and $R^4$, together with the carbon atom to which they are attached, form a cycloalkyl group, such as a $C_3$-$C_6$ cycloalkyl ring (e.g., cyclopropyl, cyclobutyl, cyclopentyl, cyclohexyl), e.g., $R^3$ and $R^4$, together with the carbon atom to which they are attached, form a cyclopropyl ring.

In other embodiments, $R^5$ is hydrogen or methyl.

In some embodiments, n is 1 and $R^1$ is aryl, heteroaryl or heterocycle.

In some embodiments, n is 2 and $R^1$ is aryl, heteroaryl or heterocycle.

In some embodiments, R3 and R4 are hydrogen.

In some embodiments, X is —C(O)—.

In some embodiments, R2 is aryl. In some embodiments, R2 is aryl and is substituted by one or more alkyl, halogen, halogenated alkyl, or cyano groups. In some embodiments, R2 is aryl and is substituted by one or more alkyl, halogen, and/or halogenated alkyl groups.

In some embodiments, R1 is aryl. In some embodiments, R1 is aryl and is substituted by one or more aryl, heteroaryl, or heterocycle.

In some embodiments, X is —C(O)—, and R2 is aryl. In some embodiments, X is —C(O)—, and R2 is aryl and is substituted by one or more halogen or halogenated alkyl groups.

In some embodiments, X is —C(O)—, R2 is aryl, and R3 and R4 are hydrogen. In some embodiments, X is —C(O)—, and R2 is aryl and is substituted by one or more halogen or halogenated alkyl groups, and R3 and R4 are hydrogen.

In some embodiments, the compound is selected from:
a) N-Biphenyl-4-yl-3-oxo-3-[4-(2-trifluoromethyl-benzoyl)-piperazin-1-yl]-propionamide,
b) N-Biphenyl-4-yl-3-[4-(2,5-dichloro-benzoyl)-piperazin-1-yl]-3-oxo-propionamide,
c) N-Biphenyl-4-yl-3-[4-(5-fluoro-2-trifluoromethyl-benzoyl)-piperazin-1-yl]-3-oxo-propionamide,
d) N-Biphenyl-4-yl-3-[4-(4-chloro-2,5-difluoro-benzoyl)-piperazin-1-yl]-3-oxo-propionamide,
e) N-Biphenyl-4-yl-3-[4-(2-methyl-benzoyl)-piperazin-1-yl]-3-oxo-propionamide,
f) N-Biphenyl-4-yl-3-[4-(2,5-difluoro-benzoyl)-piperazin-1-yl]-3-oxo-propionamide,
g) N-Biphenyl-4-yl-3-[4-(2-bromo-5-fluoro-benzoyl)-piperazin-1-yl]-3-oxo-propionamide,
h) N-Biphenyl-4-yl-3-oxo-3-[4-(3,4,5-trifluoro-benzoyl)-piperazin-1-yl]-propionamide,
i) N-Biphenyl-4-yl-3-[4-(2-chloro-5-trifluoromethyl-benzoyl)-piperazin-1-yl]-3-oxo-propionamide,
j) N-Biphenyl-4-yl-3-[4-(2-bromo-benzoyl)-piperazin-1-yl]-3-oxo-propionamide, and pharmaceutically acceptable salts thereof, pharmaceutically acceptable solvates thereof, and solvates of pharmaceutically acceptable salts thereof.

In some embodiments, the compound is selected from:
k) N-Biphenyl-4-yl-3-[4-(2,4-dichloro-5-fluoro-benzoyl)-piperazin-1-yl]-3-oxo-propionamide,
l) N-Biphenyl-4-yl-3-[4-(2-fluoro-benzoyl)-piperazin-1-yl]-3-oxo-propionamide, m) Synthesis of N-Biphenyl-4-yl-3-[4-(3-fluoro-benzoyl)-piperazin-1-yl]-3-oxo-propionamide,
n) N-Biphenyl-4-yl-3-[4-(4-fluoro-benzoyl)-piperazin-1-yl]-3-oxo-propionamide,
o) N-Biphenyl-4-yl-3-oxo-3-[4-(2-trifluoromethyl-benzyl)-piperazin-1-yl]-propionamide,
p) N-Biphenyl-4-yl-3-[4-(2-chloro-benzenesulfonyl)-piperazin-1-yl]-3-oxo-propionamide,
q) N-Biphenyl-3yl-3-oxo-[4-(2-trifluoromethyl-benzoyl)-piperazin-1-yl]-propionamide,
r) 3-Oxo-N-(5-phenyl-pyridin-2-yl)-3-[4-(2-trifluoromethyl-benzoyl)-piperazin-1-yl]-propionamide,
s) N-(4-[1,2,4]Oxadiazol-3-yl-phenyl)-3-oxo-3-[4-(2-trifluoromethyl-benzoyl)-piperazin-1-yl]-propionamide,
t) N-[4-(5-Methyl-[1,3,4]oxadiazol-2-yl)-phenyl]-3-oxo-3-[4-(2-trifluoromethyl-benzoyl)-piperazin-1-yl]-propionamide, and pharmaceutically acceptable salts thereof, pharmaceutically acceptable solvates thereof, and solvates of pharmaceutically acceptable salts thereof.

In some embodiments, the compound is selected from:
u) N-(6-Benzyloxy-pyridin-3-yl)-3-oxo-3-[4-(2-trifluoromethyl-benzoyl)-piperazin-1-yl]-propionamide,
v) 3-Oxo-N-(2-oxo-2,3-dihydro-benzooxazol-5-yl)-3-[4-(2-trifluoromethyl-benzoyl)-piperazin-1-yl]-propionamide,
w) N-Methyl-4-{3-oxo-3-[4-(2-trifluoromethyl-benzoyl)-piperazin-1-yl]-propionylamino}-benzamide,
x) 3-Oxo-N-(4-piperidin-1-yl-phenyl)-3-[4-(2-trifluoromethyl-benzoyl)-piperazin-1-yl]-propionamide
y) 3-Oxo-N-(6-phenyl-pyridin-3-yl)-3-[4-(2-trifluoromethyl-benzoyl)-piperazin-1-yl]-propionamide,
z) 3-Oxo-N-(4-phenyl-thiazol-2-yl)-3-[4-(2-trifluoromethyl-benzoyl)-piperazin-1-yl]-propionamide,
aa) 3-Oxo-N-(6-phenyl-pyridin-3-yl)-3-[4-(3,4,5-trifluoro-benzoyl)-piperazin-1-yl]-propionamide,
bb) N-(4-[1,2, and 4]Oxadiazol-3-yl-phenyl)-3-oxo-3-[4-(3,4,5-trifluoro-benzoyl)-piperazin-1-yl]-propionamide,
cc) 3-Oxo-N-(4-phenylamino-phenyl)-3-[4-(2-trifluoromethyl-benzoyl)-piperazin-1-yl]-propionamide:
dd) 3-[4-(2-Bromo-benzoyl)-piperazin-1-yl]-3-oxo-N-(6-phenyl-pyridin-3-yl)-propionamide:

and pharmaceutically acceptable salts thereof, pharmaceutically acceptable solvates thereof, and solvates of pharmaceutically acceptable salts thereof.

In some embodiments, the compound is selected from:
ee) 3-[4-(2-Bromo-benzoyl)-piperazin-1-yl]-N-(4-[1,2, and 4]oxadiazol-3-yl-phenyl)-3-oxo-propionamide,
ff) 3-[4-(2-Bromo-benzoyl)-piperazin-1-yl]-N-(4-morpholin-4-yl-phenyl)-3-oxo-propionamide, and
gg) 3-[4-(2-Bromo-benzoyl)-piperazin-1-yl]-3-oxo-N-[4-(2-oxo-2H-pyridin-1-yl)-phenyl]-propionamide,
hh) 1-[4-(2-Bromo-benzoyl)-piperazine-1-carbonyl]-cyclopropanecarboxylic acid biphenyl-4-ylamide,
ii) N-Biphenyl-4-yl-3-[4-(2-bromo-benzoyl)-piperazin-1-yl]-2-fluoro-3-oxo-propionamide,
jj) N-Biphenyl-4-yl-3-[4-(3-cyano-benzoyl)-piperazin-1-yl]-2-fluoro-3-oxo-propionamide,
kk) N-Biphenyl-4-yl-3-[4-(3-Fluoro-benzoyl)-piperazin-1-yl]-2-fluoro-3-oxo-propionamide,
ll) N-Biphenyl-4-yl-3-[4-(2-bromo-benzoyl)-piperazin-1-yl]-2-methyl-3-oxo-propionamide,
mm) N-Biphenyl-4-yl-3-[4-(2-bromo-benzoyl)-piperazin-1-yl]-N-methyl-3-oxo-propionamide,
oo) 3-[4-(2-Bromo-benzoyl)-piperazin-1-yl]-3-oxo-N-(3-phenyl-isoxazol-5-yl)-propionamide, and pharmaceutically acceptable salts thereof, pharmaceutically acceptable solvates thereof, and solvates of pharmaceutically acceptable salts thereof.

In some embodiments, the compound is selected from:
pp) N-Biphenyl-4-yl-3-(4-cyclohexanecarbonyl-piperazin-1-yl)-3-oxo-propionamide,
qq) N-Biphenyl-4-yl-3-[4-(2-bromo-benzoyl)-[1,4]diazepan-1-yl]-3-oxo-propionamide,
rr) 3-[4-(2-Bromo-benzoyl)-piperazin-1-yl]-N-[5-(4-fluoro-phenyl)-isoxazol-3-yl]-3-oxo-propionamide,
ss) 3-[4-(2-Bromo-benzoyl)-piperazin-1-yl]-3-oxo-N-(4-pyridin-3-yl-phenyl)-propionamide,
tt) 3-[4-(2-Bromo-benzoyl)-piperazin-1-yl]-3-oxo-N-(1-phenyl-1H-pyrazol-4-yl)-propionamide,
uu) N-Biphenyl-4-yl-3-oxo-3-[4-(3,4,5-trifluoro-benzyl)-piperazin-1-yl]-propionamide,
vv) 3-[4-(2-Bromo-benzoyl)-piperazin-1-yl]-3-oxo-N-(4-thiophen-3-yl-phenyl)-propionamide,
ww) 3-[4-(2-Bromo-benzoyl)-piperazin-1-yl]-3-oxo-N-(5-phenyl-pyridin-2-yl)-propionamide,
xx) 3-Oxo-N-(5-phenyl-pyridin-2-yl)-3-[4-(3,4,5-trifluoro-benzoyl)-piperazin-1-yl]-propionamide, and pharmaceutically acceptable salts thereof, pharmaceutically acceptable solvates thereof, and solvates of pharmaceutically acceptable salts thereof;

wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

As used herein the term "halogen" means any suitable halogen, such as F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one or more halogens, such as, but not limited to, —CF$_3$, —CF$_2$CF$_3$, —CHF$_2$, —CH$_2$F, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means —NH$_2$.

The term "alkylamino" means —NH(alkyl), wherein alkyl is as described above.

The term "dialkylamino" means —N(alkyl)$_2$, wherein alkyl is as described above.

The term "aryl" means a substituted or unsubstituted aromatic monocyclic or bicyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means —NH(aryl), wherein aryl is as described above.

The term "diarylamino" means —N(aryl)$_2$, wherein aryl is as described above.

The term "amido" means —CONH$_2$.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means —C(O)OH.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previously described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, but not limited to, halogen, hydroxyl, amino, carboxy, alkylamino, dialkylamino, aryl, heteroaryl, alkoxy, nitro and combinations thereof.

The term "heteroarylalkyl" refers to a -(alkylene)-heteroaryl group wherein the heteroaryl and alkylene portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocyclealkyl" refers to a -(alkylene)-heterocycle group wherein the heterocycle and alkylene portions are in accordance with the previous discussions.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous discussion. Suitable alkoxy groups include, but are not limited to, methoxy, ethoxy, n-propoxy, iso-propoxy, n-butoxy, t-butoxy, pentoxy, hexoxy, heptoxy, octoxy, and the like. For example, the alkoxy can be methoxy or ethoxy.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —SO$_2$R radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —SO$_2$R radical where R is aryl as defined above, e.g., phenylsulfonyl, and the like.

The term "heteroarylsulfinyl" means a —SOR radical where R is heteroaryl as defined above.

The term "heteroarylsulfonyl" means a —SO$_2$R radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

One of ordinary skill in the art will recognize that the compounds of the present invention can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of the present invention can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10) (2000), 110 pp.; Kabalka, George W.; Varma, Rajender S. The synthesis of radiolabeled compounds via organometallic intermediates. Tetrahedron (1989), 45(21), 6601-21; and Evans, E. Anthony. Synthesis of radiolabeled compounds, J. Radioanal. Chem. (1981), 64(1-2), 9-32.]

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, aDIPEAtes, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of the present invention can exist in different solvate forms. Solvates of the compounds of the invention may also form when solvent molecules are incorporated into the crystalline lattice structure of the compound molecule during the crystallization process.

The present invention also includes prodrugs of the compounds discussed herein. The term prodrug is intended to represent covalently bonded carriers, which are capable of releasing the active ingredient of the compounds discussed herein, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the present invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the present invention), amides (e.g., trifluoroacetylamino, acetylamino, and the like), and the like. Prodrugs of compounds discussed herein are also within the scope of this invention.

The present invention also provides processes for preparing the compounds of the present invention. Suitable general reaction schemes are shown below.

Method-I

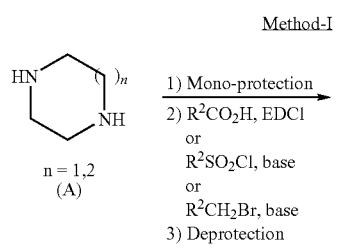

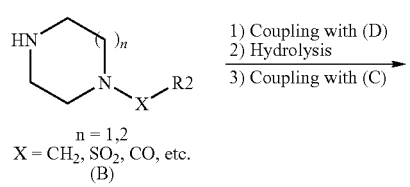

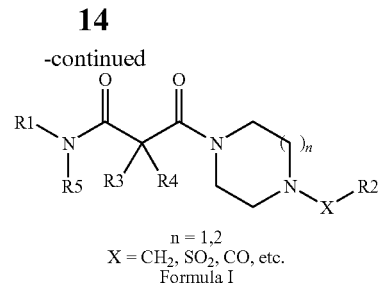

The starting material (A) for the above reaction scheme (commercially available from Aldrich, St Louis, Mo.), is first mono-protected with a Boc, Benzyl or Cbz group via standard conditions known to one of ordinary skill. For example, the protected compound is then reacted with an appropriately substituted carboxylic acid in the presence of a standard peptide coupling reagent (such as EDCI) to give the desired amide product (when X=—C(O)—), which is deprotected to give compound (B). Amine (B) may be reacted with an appropriately substituted carboxylic acid (D) (where Y=OH) in the presence of a standard peptide coupling reagent such as EDCI or, alternatively, amine (B) may be reacted with an appropriately substituted carboxylic acid chloride (D) (where Y=Cl) to give the desired amide product, which undergoes standard hydrolysis procedure known to the one skilled in the art to generate a carboxylic acid which may then be coupled with compound (C) under standard amide bond formation conditions known to the one skilled in the art to give a compound of the present invention.

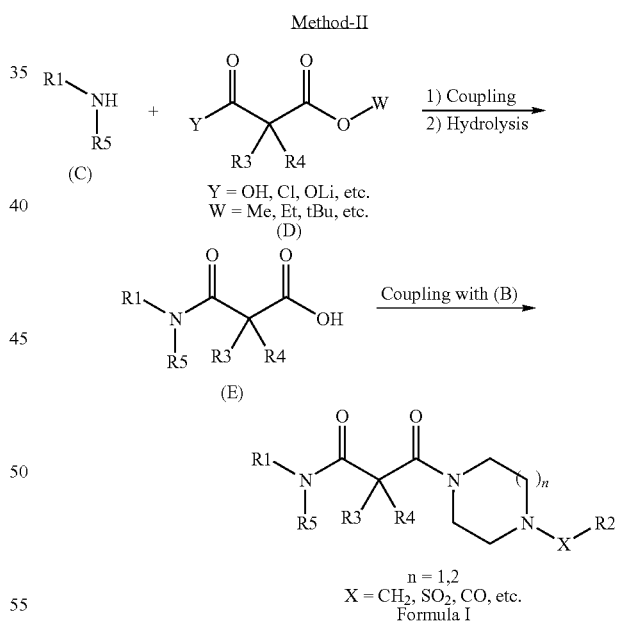

The starting materials for the above reaction scheme are commercially available or may be prepared according to methods known to one of ordinary skill in the art or by methods disclosed herein.

Amine compound (C) may be reacted with an appropriately substituted carboxylic acid (D) (where Y=OH) in the presence of a standard peptide coupling reagent (such as EDCI), or, alternatively, amine (C) may be reacted with an appropriately substituted carboxylic acid chloride (D) (where Y=Cl) to give the desired amide product, which undergoes standard hydrolysis procedures known to the one skilled in the art to generate carboxylic acid (E). The coupling between compounds (B) and (E) under standard amide bond formation conditions known to the one skilled in the art affords the compound of the present invention.

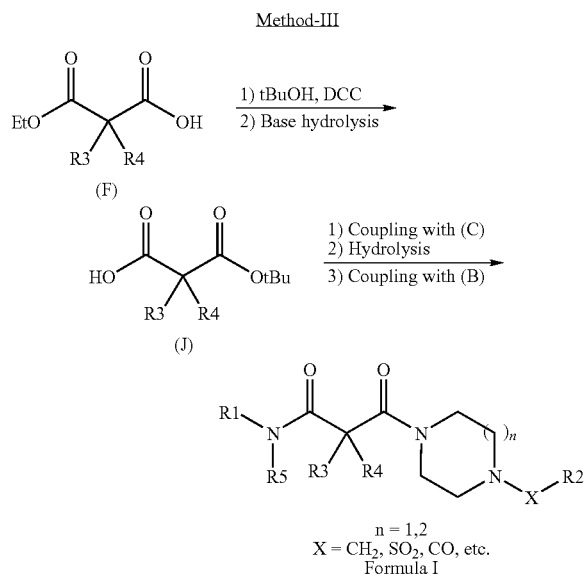

Compound (F) (which is commercially available, for example, from Aldrich, St Louis, Mo.), may be esterified in t-BuOH and subjected to standard hydrolysis procedures to afford compound (J). Coupling between compounds (J) and (B) in presence of a standard peptide coupling reagent (such as EDCI) affords an amide product, which may be further hydrolysed under standard conditions, and then coupled with compound (C) under standard amide bond formation conditions to afford a compound of the present invention.

The compounds of the invention can be administered alone or as an active ingredient of a formulation. Thus, the present invention also includes pharmaceutical compositions of the compounds of the present invention, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of the present invention may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, the compounds of the present invention can be administered by inhalation in the form of a powder (e.g., micronized) or in the form of atomized solutions or suspensions. The aerosol formulation can be placed into a pressurized acceptable propellant.

The compounds of the present invention may be useful as inhibitors of stearoyl-CoA desaturase (SCD) enzymes, for example, as inhibitors of SCD1 enzyme. Therefore, the compounds are useful in the treatment of conditions mediated by stearoyl-CoA desaturase (SCD) enzymes, e.g., SCD1 enzyme.

According to another embodiment, the present invention relates to a method of treating a disease or condition mediated by stearoyl-CoA desaturase (e.g., SCD1) by administering to a patient in need thereof a therapeutically effective amount of a compound of the present invention.

An SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including, but not limited to stroke, ischemic stroke and transient ischemic attack (TIA), peripheral vascular disease, and ischemic retinopathy. In an embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In an embodiment, the compounds discussed herein are useful in the treatment of diabetes mellitus and obesity. In another embodiment, the compounds discussed herein are useful in the treatment of obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes, but is not limited to, a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including, but not limited to, eczema, acne, psoriasis, keloid scar formation or prevention, diseases related to production or secretions from mucous membranes, such as monounsaturated fatty acids, wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

In one embodiment, the compounds of the inventions are useful in the treatment of elevated levels of lipids, cardiovascular diseases, diabetes, obesity, and metabolic syndrome.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a compound of the present invention that, when administered to a patient (e.g., a mammal) for treating a disease, is sufficient to effect such treatment for the disease to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of the present invention may be used in combination with other drugs or therapies that are used in the treatment/prevention/suppression or amelioration of the diseases or conditions for which the compounds discussed herein are useful.

Such other drug(s) may be administered, by a route and in an amount commonly used therefor, contemporaneously or sequentially with a compound of the present invention. When a compound of the present invention is used contemporaneously with one or more other drugs, a pharmaceutical unit dosage form containing such other drugs in addition to the compound of the present invention may be employed. Accordingly, the pharmaceutical compositions of the present invention include those that also contain one or more other active ingredients, in addition to a compound of the present invention.

EXAMPLES

The present invention will now be further described by way of the following non-limiting examples. In applying the disclosure of these examples, it should be kept clearly in mind that other and different embodiments of the synthetic methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The following abbreviations are used herein: Ac (CH$_3$CO), BINAP (2,2'-bis(diphenylphosphino)-1,1'-binaphthyl), Bn (benzyl), DCM (dichloromethane), DMF (dimethylformamide), DIPEA/DIEA (N,N'-diisopropylethylamine), DCC (dicylcohexyl carbodidimide), EDCI (1-ethyl-3-[3-dimethylaminopropyl]carbodiimide hydrochloride), DMAP (N,N-dimethyl aminopyridine), Et (ethyl), HOBT (1-hydroxybenzotriazole), Me (methyl), TFA (trifluoroacetic acid), THF (tetrahydrofuran), EtOAc (ethyl acetate), MeOH (methanol), Pd(OAc)$_2$ (palladium acetate), K$_2$CO$_3$ (potassium carbonate), HCOONH$_4$ (ammonium formate), Pd/C (palladium on carbon), Boc (tert-butoxycarbonyl), Na$_2$SO$_4$ (sodium sulphate), NaHCO$_3$ (sodium bicarbonate) HCl (hydrochloric acid), HBr (hydrogen bromide), NaCl (sodium chloride), brine (saturated sodium chloride solution), CHCl$_3$ (chloroform), Cs$_2$CO$_3$ (caesium carbonate, cesium carbonate), NaClO$_2$ (sodium chlorite), NH$_3$SO$_3$ [NH$_2$.SO$_3$H] (Sulphamic acid), NaOH (sodium hydroxide), CBZ (benzyloxy carbonyl), Boc (tertiary butoxy carbonyl), DMAP (dimethyl amino pyridine), LAH (lithium aluminum hydride), LiOH (lithium hydroxide), KOH (potassium hydroxide), conc. (concentrated), celite (diatomaceous earth), TLC (thin layer chromatography), NMR (nuclear magnetic resonance), DMSO-d$_6$ (deuterated dimethyl sulfoxide), CDCl$_3$ (deuterated chloroform), LC-MS (liquid chromatography-mass spectrometry), HPLC (high pressure liquid chromatography or high performance liquid chromatography).

Synthesis of piperazine-1-carboxylic acid tert-butyl ester

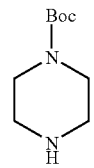

To a stirred solution of piperazine (40 g, 464 mmol) in tert-butanol (553 mL) and water (556 mL) was added NaOH solution dropwise (73 mL, 2.5 N) at 0° C. followed by di-tert-butyl dicarbonate (40.5 g, 185.7 mmol). The stirring was continued at room temperature overnight. The reaction mixture was then stripped of tert-butanol and filtered. The filtrate was extracted with dichloromethane and the organic layer was washed with brine, dried over Na$_2$SO$_4$ and concentrated under reduced pressure to afford 49 g (86.5%) of piperazine-1-carboxylic acid tert-butyl ester. LCMS: 187.14 (M+1)$^+$, 98.54%, $^1$H NMR: (DMSO-d$_6$): δ 3.2 (t, 4H), 2.6 (t, 4H), 1.38 (s, 9H).

Synthesis of 4-(2,5-dichloro-benzoyl)-piperazine-1-carboxylic acid tert-butyl ester

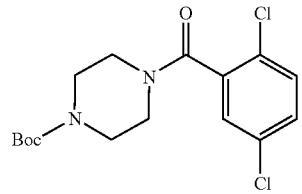

HOBt (213 mg, 1.5 mmol) and DIEA (508 mg, 3.9 mmol) were added to a stirred solution of 2,5-dichlorobenzoicacid (250 mg, 1.3 mmol) in DMF (2.5 mL). The reaction mixture was then cooled to 10° C. and EDCI.HCl (302 mg, 1.5 mmol) followed by piperazine-1-carboxylic acid tert-butyl ester (260 mg, 1.3 mmol) were added. The resulting mixture was stirred at room temperature overnight. The reaction mixture was then diluted with water and the product extracted with ethyl acetate. The ethyl acetate layer was washed with brine solution, dried over Na$_2$SO$_4$, and concentrated under reduced pressure to afford the crude residue which was purified by column chromatography using silica gel 60-120 mesh (30% ethyl acetate in hexane) to afford 396 mg (84%) of 4-(2,5-dichloro-benzoyl)-piperazine-1-carboxylic acid tert-butyl ester, LCMS: 360.08 (M+1)$^+$, 98.2%.

Synthesis of 4-(2,5-dichloro-phenyl)-piperazin-1-yl-methanone.hydrochloride

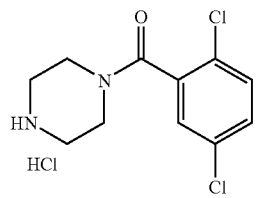

A solution of 4-(2,5-dichloro-benzoyl)-piperazine-1-carboxylic acid tert-butyl ester (390 mg, 1.08 mmol) in 1,4- dioxane (1 mL) was cooled to 0° C. Dioxane.HCl (1 mL) was then added and the resulting mixture stirred for 15 minutes. The reaction mixture was then concentrated under reduced pressure to afford a solid, which was washed with ether and dried to afford 313 mg (97%) of 4-(2,5-dichloro-phenyl)-piperazin-1-yl-methanone.hydrochloride, LCMS: 296.01 (M+1)$^+$, 96.09%.

Synthesis of 4-(5-fluoro-2-trifluoromethyl-benzoyl)-piperazine-1-carboxylic acid tert-butyl ester

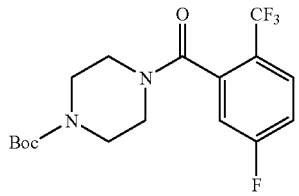

HOBt (163 mg, 1.2 mmol) and DIEA (373 mg, 2.9 mmol) were added to a stirred solution of 5-fluoro-2-trifluoromethyl-benzoic acid (200 mg, 0.9 mmol) in DMF (1.0 mL) and the resulting mixture was cooled to 10° C. EDCI.HCl (231 mg, 1.2 mmol) followed by piperazine-1-carboxylic acid tert-butyl ester (197 mg, 1.0 mmol) were then added and the mixture was stirred at room temperature overnight. The reaction mixture was diluted with water and the product extracted with ethyl acetate. The ethyl acetate layer was washed with brine solution, dried over Na$_2$SO$_4$ and concentrated under reduced pressure to afford the crude residue, which was purified by column chromatography using silica gel 60-120 mesh (30% ethyl acetate in hexane) to afford 301 mg (83%) of 4-(5-fluoro-2-trifluoromethyl-benzoyl)-piperazine-1-carboxylic acid tert-butyl ester, LCMS purity: 99.5%.

Synthesis of (5-fluoro-2-trifluoromethyl-phenyl)-piperazin-1-yl methanone hydrochloride

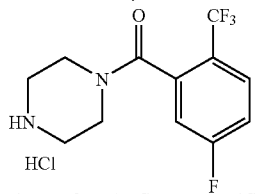

A stirred solution of 4-(5-fluoro-2-trifluoromethyl-benzoyl)-piperazine-1-carboxylic acid tert-butyl ester (295 mg, 0.78 mmol) in dioxane was cooled to 0° C. and dioxane.HCl (1 mL) was added. The reaction mixture was stirred for 15 minutes, then concentrated. The resulting solid was washed with diethyl ether and dried to afford 220 mg (89%) of (5-fluoro-2-trifluoromethyl-phenyl)-piperazin-1-yl methanone hydrochloride, LCMS: 313.07 (M+1)$^+$, 97.2%. Intermediate-3

Synthesis of 4-(2-bromo-benzoyl)-piperazine-1-carboxylic acid tert-butyl ester

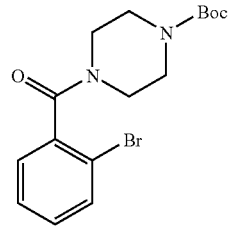

HOBt (4 g, 29.6 mmol) and DIEA (8.7 g, 67.7 mmol) were added to a stirred solution of 2-bromo benzoic acid (5.6 g, 28.3 mmol) in DMF (50 mL). The reaction mixture was cooled to 10° C. and EDCI.HCl (7.76 g, 40.48 mmol) followed by piperazine-1-carboxylic acid tert-butyl ester (5 g, 26.9 mmol) were added. Then reaction mixture was stirred at the room temperature overnight. Water was added and the product was extracted with ethyl acetate. The ethyl acetate was washed with brine solution, dried over Na$_2$SO$_4$, and removed under reduced pressure to afford 9 g (90%) of 4-(2-bromo-benzoyl)-piperazine-1-carboxylic acid tert-butyl ester. $^1$H NMR: (DMSO-d$_6$): δ 7.58 (d, 1H), 7.38 (t, 1H), 7.29 (d, 1H), 7.24 (d, 1H), 3.85 (m, 1H), 3.7 (m, 1H), 3.55 (t, 2H), 3.5 (m, 1H), 3.3 (m, 3H), 3.15 (m, 1H), 1.45 (s, 9H).

Synthesis of (2-bromo-phenyl)-piperazin-1-yl-methanone hydrochloride salt

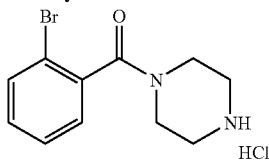

Dioxane.HCl (50 mL) was added to 4-(2-bromo-benzoyl)-piperazine-1-carboxylic acid tert-butyl ester (9 g, 24.4 mmol) at 0° C. The resulting mixture was stirred for 4 hours, then concentrated. The resulting residue was washed with 1% MeOH in ethyl acetate and dried under reduced pressure to afford 7.1 g (95%) of (2-bromo-phenyl)-piperazin-1-yl-methanone hydrochloride salt, LCMS: 306.6 (M+1)$^+$, 86.8%, $^1$H NMR: (DMSO-d$_6$): δ 9.6 (s, 2H), 7.7 (d, 1H), 7.45 (m, 3H), 4.0 (m, 1H), 3.76 (m, 1H), 3.18 (bs, 2H), 3.06 (bs, 2H).

Synthesis of (4-benzyl-piperazin-1-yl)-(2-trifluoromethyl-phenyl)-methanone

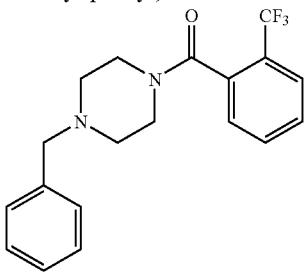

HOBt (4.26 g, 31.5 mmol) and DIEA (10.19 g, 78.89 mmol) were added to a stirred solution of 2-trifluoromethyl-benzoic acid (5 g, 26.3 mmol) in DMF (20 mL). The reaction mixture was cooled to 10° C. and EDCI.HCl (12.6 g, 65.7 mmol) followed by 1-benzyl-piperazine (5.56 g, 31.55 mmol) were then added. The reaction mixture was stirred at room temperature overnight, then diluted with water and the product extracted with ethyl acetate. The ethyl acetate was washed with brine solution, dried over Na$_2$SO$_4$ and evaporated. The resulting residue was purified by column chromatography using silica gel 60-120 mesh with (30% ethyl acetate in hexane) to afford 8.6 g (93%) of (4-benzyl-piperazin-1-yl)-(2-trifluoromethyl-phenyl)-methanone. $^1$H NMR: (DMSO-d$_6$): δ 7.8 (m, 2H), 7.6 (t, 1H), 7.4 (d, 1H), 7.3 (m, 5H), 3.6 (m, 2H), 3.5 (s, 2H), 3.1 (m, 2H), 2.4 (m, 1H), 2.3 (m, 2H), 2.2 (m, 1H).

Synthesis of piperazin-1-yl-(2-trifluoromethyl-phenyl)-methanone

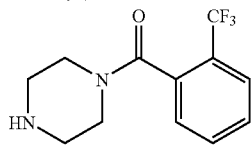

NH$_4$COOH (15.5 g, 247 mmol) and 10% Pd/C (1.8 g) in water (2 mL) were added to a stirred solution of (4-benzyl-piperazin-1-yl)-(2-trifluoromethyl-phenyl)-methanone (8.6 g, 24.7 mmol) in MeOH (40 mL) and the resulting mixture was heated to reflux at 75° C. for 4 hrs. The reaction mixture was then filtered over celite and the filtrate evaporated. The resulting residue was dissolved in ethyl acetate, washed with 10% NaOH solution then brine solution, dried over Na$_2$SO$_4$ and concentrated under reduced pressure to afford 5.5 g (86%) of piperazin-1-yl-(2-trifluoromethyl-phenyl)-methanone. $^1$H NMR: (DMSO-d$_6$): δ 7.8 (d, 1H), 7.7 (t, 1H), 7.6 (t, 1H), 7.4 (d, 1H), 3.5 (m, 2H), 3.0 (m, 2H), 2.7 (m, 5H).

Synthesis of piperazin-1-yl-(2-trifluoromethyl-phenyl)-methanone hydrochloride

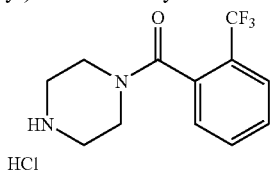

A solution of piperazin-1-yl-(2-trifluoromethyl-phenyl)-methanone (5.5 g, 21.4 mmol) in diethylether.HCl was stirred at 0° C. for 30 minutes. The mixture was then concentrated, and the resulting residue washed with benzene and dried to afford 5.7 g (91%) of piperazin-1-yl-(2-trifluoromethyl-phenyl)-methanone hydrochloride. $^1$H NMR: (DMSO-d$_6$): δ 9.6 (s, 2H), 7.8 (m, 2H), 7.6 (m, 2H), 4.0 (m, 1H), 3.8 (m, 1H), 3.0 (m, 1H), 3.4 (m, 2H), 3.1 (m, 3H), 2.9 (m, 1H).

Synthesis of (4-benzyl-piperazin-1-yl)-(3,4,5-trifluorophenyl)-methanone

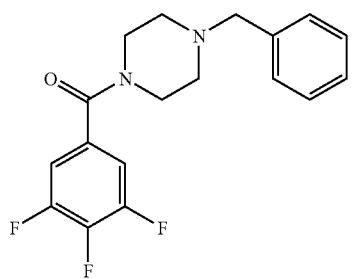

DIC (1.34 g, 10.2 mmol) was added drop wise to a stirred solution of 3,4,5-trifluoro benzoic acid (1.5 g, 8.5 mmol) in THF (10 mL) and the resulting mixture was maintained for 30 minutes at room temperature. Mono benzyl piperazine (1.64 g, 9.35 mmol) was then added and the mixture heated to reflux at 70° C. overnight, under an atmosphere of nitrogen. The resulting solid precipitate was filtered and the filtrate was washed with water and evaporated. The residue was purified by column chromatography using silica gel 60-120 mesh (12% ethyl acetate in hexane) to afford 1.7 g (60%) of (4-benzyl-piperazin-1-yl)-(3,4,5-trifluoro-phenyl)-methanone. $^1$H NMR: (CDCl$_3$): δ 7.32 (m, 5H), 7.06 (t, 2H), 3.75 (bs, 2H), 3.54 (s, 2H), 3.44 (bs, 2H), 2.46 (bs, 4H).

Synthesis of piperazin-1-yl-(3,4,5-trifluoro-phenyl)-methanone

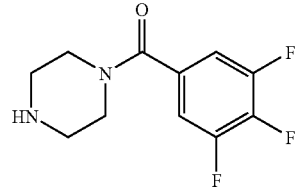

10% Pd/C (80 mg) was added to a stirred solution of (4-benzyl-piperazin-1-yl)-(3,4,5-trifluoro-phenyl)-methanone (800 mg, 2.4 mmol) in methanol (20 mL) and the mixture was stirred under an atmosphere of hydrogen for 6 hours. The mixture was then filtered over celite and the filtrate concentrated to afford 600 mg (95%) of piperazin-1-yl-(3,4,5-trifluoro-phenyl)-methanone. LCMS: 245.09 (M+1)$^+$, 92.4%

Synthesis of N-biphenyl-4-yl-malonamic acid ethyl ester

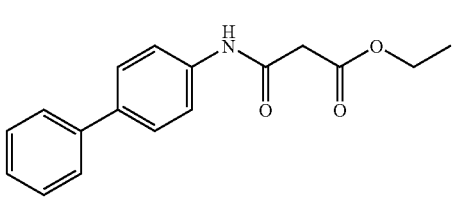

HOBt (160 mg, 1.2 mmol) and DMAP (295 mg, 2.4 mmol) were added to a stirred solution of monoethyl malanoate (173 mg, 1.3 mmol) in DMF (5 mL). The mixture was cooled to 10° C. and EDCI.HCl (345 mg, 1.2 mmol) followed by biphenyl-4-ylamine (200 mg, 1.2 mmol) were then added. After stirring at room temperature overnight, water was added and the product was extracted with ethyl acetate. The organic layer was washed with brine solution, dried over Na$_2$SO$_4$ and concentrated to afford a residue that was purified by column chromatography using silica gel 60-120 mesh and 16% ethyl acetate in Hexane as eluant to afford 100 mg (30%) of N-biphenyl-4-yl-malonamic acid ethyl ester. LCMS: 284.12 (M+1)$^+$, 98.6%, $^1$H NMR: (CDCl$_3$): δ 9.3 (s, 1H), 7.6 (m, 6H), 7.44 (t, 2H), 7.3 (t, 1H), 4.3 (q, 2H), 3.5 (s, 2H), 1.35 (t, 3H).

Synthesis of N-biphenyl-4-yl-malonamic acid

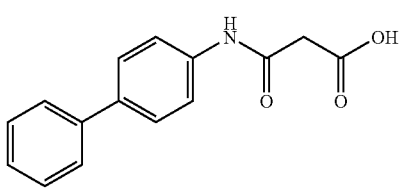

LiOH.H$_2$O (29 mg, 0.7 mmol) was added to a solution of N-biphenyl-4-yl-malonamic acid ethyl ester (100 mg, 0.35 mmol) in methanol (2.1 mL), THF (2.5 mL) and H$_2$O (2.5 mL). The resulting mixture was stirred for 2 hours at room temperature then concentrated. The residue was diluted with water and washed with diethyl ether. The aqueous layer was acidified with concentrated HCl and filtered. The resulting precipitate was dried to afford 80 mg (89%) of N-biphenyl- 4-yl-malonamic acid. $^1$H NMR: (DMSO-$d_6$): δ11.6 (s, 1H), 7.64 (m, 6H), 7.44 (t, 2H), 7.32 (t, 1H), 3.2 (s, 1H).

Example 1

Synthesis of N-Biphenyl-4-yl-3-oxo-3-[4-(2-trifluoromethyl-benzoyl)-piperazin-1-yl]-propionamide

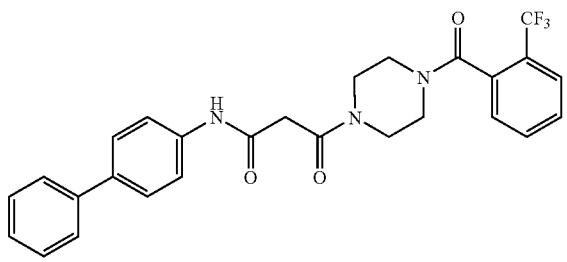

HOBt (19 mg, 0.14 mmol) and DIPEA (0.017 mg, 0.14 mmol) were added to a stirred solution of N-biphenyl-4-yl-malonamic acid (40 mg, 0.14 mmol) in DMF (3 mL). The mixture was cooled to 10° C. and EDCI.HCl (40 mg, 0.2 mmol) followed by piperazin-1-yl-(2-trifluoromethyl-phenyl)-methanone hydrochloride (45 mg, 0.15 mmol) were added. The mixture was stirred at room temperature overnight, then diluted with water. The resulting precipitate was filtered and the residue was purified by column chromatography using silica gel 60-120 mesh and 90% ethyl acetate in hexane as eluant to afford 20 mg (30%) of N-biphenyl-4-yl-3-oxo-3-[4-(2-trifluoromethyl-benzoyl)-piperazin-1-yl]-propionamide. LCMS: 496.18 (M+1)$^+$, 97.3%. $^1$H NMR: (CDCl$_3$): δ 9.6 (d, 1H), 7.76 (d, 1H), 7.6 (m, 7H), 7.44 (t, 2H), 7.35 (t, 2H), 4.0 (m, 2H), 3.7 (m, 4H), 3.5 (m, 4H), 3.25 (m, 2H).

Example 2

Synthesis of N-Biphenyl-4-yl-3-[4-(2,5-dichloro-benzoyl)-piperazin-1-yl]-3-oxo-propionamide

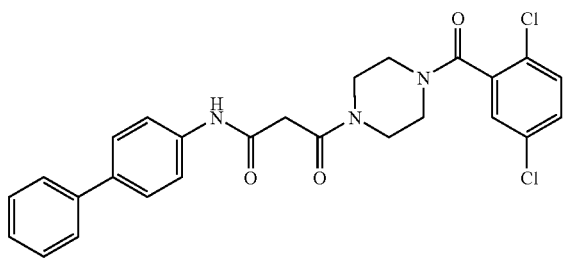

HOBt (25 mg, 0.185 mmol) and DIPEA (22 mg, 0.175 mmol) were added to a stirred solution of N-biphenyl-4-yl-malonamic acid (50 mg, 0.175 mmol) in DMF (3 mL). The reaction mixture was cooled to 10° C. and EDCI.HCl (50 mg, 0.26 mmol) was added followed by the addition of (2,5-dichloro-phenyl)-piperazin-1-yl-methanone hydrochloride (55 mg, 0.187 mmol). The reaction mixture was stirred at room temperature overnight. Water was then added and the resulting precipitate was filtered and purified by column chromatography using silica gel 60-120 mesh and 50% ethyl acetate in hexane as eluant to afford 35 mg (41%) of N-biphenyl-4-yl-3-[4-(2,5-dichloro-benzoyl)-piperazin-1-yl]-3-oxo-propionamide. LCMS: 497.11 M+1)$^+$, 95.5%. $^1$H NMR: (CDCl$_3$): δ 9.6 (d, 1H), 7.64 (m, 2H), 7.58 (m, 4H), 7.44 (m, 3H), 7.38 (d, 2H), 7.32 (m, 2H), 3.95 (m, 2H), 3.8 (m, 1H), 3.75 (m, 4H), 3.65 (m, 1H), 3.52 (d, 3H), 3.34 (m, 3H).

Example 3

Synthesis of N-Biphenyl-4-yl-3-[4-(5-fluoro-2-trifluoromethyl-benzoyl)-piperazin-1-yl]-3-oxo-propionamide

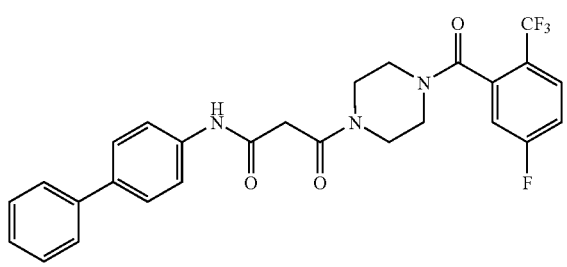

HOBt (25 mg, 0.185 mmol) and DIPEA (22 mg, 0.175 mmol) were added to a stirred solution of N-biphenyl-4-yl-malonamic acid (50 mg, 0.175 mmol) in DMF (3 mL). The reaction mixture was cooled to 10° C. and EDCI.HCl (50 mg, 0.26 mmol) followed by (2-trifluoromethyl-5-fluoro-phenyl)-piperazin-1-yl-methanone hydrochloride (60 mg, 0.193 mmol) were added. The reaction mixture was stirred at room temperature overnight. Water was then added and the resulting precipitate was filtered. The solid was purified by column chromatography using silica gel 60-120 mesh and 40% ethyl acetate in hexane as eluant to afford 34 mg (38%) of N-biphenyl-4-yl-3-[4-(5-fluoro-2-trifluoromethyl-benzoyl)-piperazin-1-yl]-3-oxo-propionamide. LCMS: 514.17M+1)$^+$, 95.5%. $^1$H NMR: (CDCl$_3$): δ 9.6 (d, 1H), 7.75 (m, 1H), 7.6 (m, 6H), 7.44 (t, 2H), 7.35 (t, 1H), 7.2 (m, 1H), 7.06 (m, 1H), 4.0 (m, 2H), 3.7 (m, 4H), 3.56 (s, 2H), 3.48 (s, 1H), 3.26 (m, 3H).

Synthesis of 4-[2-(Biphenyl-4-ylcarbamoyl)-acetyl]-piperazine-1-carboxylic acid tert-butyl ester

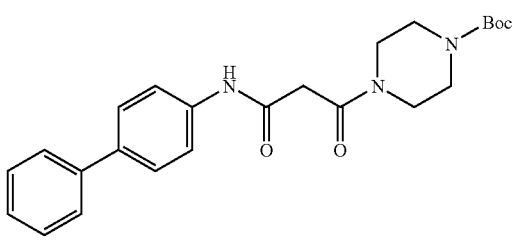

HOBt (570 mg, 4.2 mmol) and DIPEA (541 mg, 4.2 mmol) were added to a stirred solution of N-biphenyl-4-yl-malonamic acid (1 g, 3.5 mmol) in DMF (10 mL). The reaction mixture was cooled to 10° C. and EDCI.HCl (810 mg, 4.2 mmol) followed by piperazine-1-carboxylic acid tert-butyl ester (720 mg, 3.86 mmol) were added. The resulting reaction mixture was stirred at room temperature overnight. Water was then added and the resulting precipitate was filtered and dried to afford 1.4 g (93%) of 4-[2-(biphenyl-4-ylcarbamoyl)-acetyl]-piperazine-1-carboxylic acid tert-butyl ester. $^1$H NMR: (CDCl$_3$): δ 8.6 (s, 1H), 7.9 (m, 2H), 7.7 (m, 2H), 7.65 (m, 1H), 7.5 (m, 3H), 7.4 (s, 1H), 4.1 (m, 2H), 3.6 (m, 4H), 3.4 (m, 2H), 3.1 (m, 2H).

Synthesis of N-Biphenyl-4-yl-3-oxo-3-piperazin-1-yl-propionamide hydrochloride

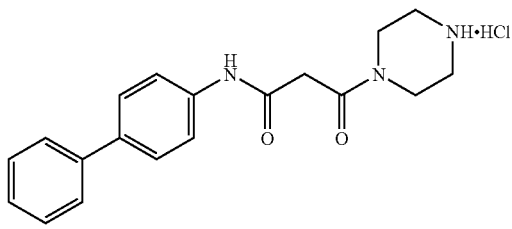

Dioxane.HCl (10 mL) was added to 4-[2-(biphenyl-4-yl-carbamoyl)-acetyl]-piperazine-1-carboxylic acid tert-butyl ester (1.3 g, 3.1 mmol) and the resulting mixture was stirred for 30 minutes, then concentrated. The residue was washed with diethyl ether and dried to afford 1.0 g (90%) of N-Biphenyl-4-yl-3-oxo-3-piperazin-1-yl-propionamide hydrochloride Example 4

Synthesis of N-Biphenyl-4-yl-3-[4-(4-chloro-2,5-difluoro-benzoyl)-piperazin-1-yl]-3-oxo-propionamide

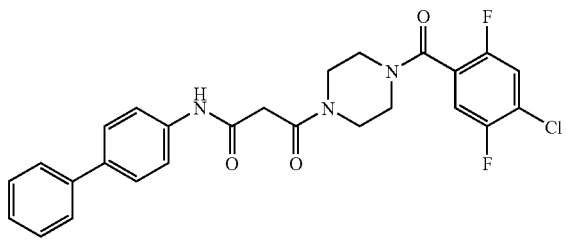

HOBt (34 mg, 0.25 mmol) and DIPEA (67.9 mg, 0.51 mmol) were added to a stirred solution of 4-chloro-2,5-difluoro-benzoic acid (40 mg, 0.21 mmol) in DMF (1 mL). The reaction mixture was cooled to 10° C. and EDCI.HCl (48 mg, 0.25 mmol) followed by N-biphenyl-4-yl-3-oxo-3-piperazin-1-yl-propionamide.hydrochloride (75 mg, 0.2 mmol) were added. The mixture was stirred at room temperature overnight then diluted with water. The resulting precipitate was filtered then purified by column chromatography using silica gel 60-120 mesh and 60% ethyl acetate in hexane to afford 24 mg (23%) of N-biphenyl-4-yl-3-[4-(4-chloro-2,5-difluoro-benzoyl)-piperazin-1-yl]-3-oxo-propionamide. LCMS: 498.18 (M+1)$^+$, 97.0%. $^1$H NMR: (CDCl$_3$): δ 9.6 (d, 1H), 7.52 (m, 6H), 7.49 (t, 2H), 7.35 (t, 1H), 7.25 (t, 1H), 3.7 (m, 3H), 3.56 (d, 3H), 3.55 (d, 2H), 3.4 (m, 2H).

Example 5

Synthesis of N-Biphenyl-4-yl-3-[4-(2-methyl-benzoyl)-piperazin-1-yl]-3-oxo-propionamide

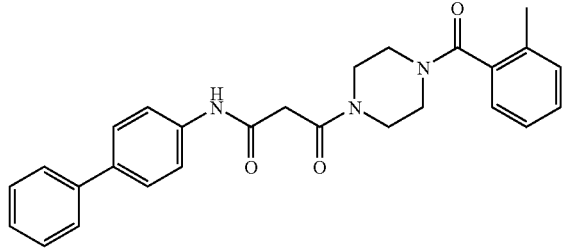

HOBt (34 mg, 0.25 mmol) and DIPEA (67.9 mg, 0.51 mmol) were added to a stirred solution of 2-methyl-benzoic acid (29 mg, 0.21 mmol) in DMF (2 mL). The reaction mixture was cooled to 10° C. and EDCI.HCl (48 mg, 0.25 mmol) followed by N-biphenyl-4-yl-3-oxo-3-piperazin-1-yl-propionamide.hydrochloride (75 mg, 0.2 mmol) were added. The reaction mixture was stirred at room temperature overnight, then diluted with water. The resulting precipitate was filtered then purified by column chromatography using silica gel 60-120 mesh (80% ethyl acetate in hexane) to afford 23 mg (25%) of N-Biphenyl-4-yl-3-[4-(2-methyl-benzoyl)-piperazin-1-yl]-3-oxo-propionamide. LCMS: 442.21 (M+1)$^+$, 95.7%. $^1$H NMR: (CDCl$_3$): δ 9.6 (d, 1H), 7.6 (m, 6H), 7.42 (t, 2H), 7.32 (t, 2H), 7.22 (m, 1H), 7.16 (d, 1H), 3.8 (m, 4H), 3.5 (m, 4H), 3.3 (m, 2H).

Example 6

Synthesis of N-Biphenyl-4-yl-3-[4-(2,5-difluoro-benzoyl)-piperazin-1-yl]-3-oxo-propionamide

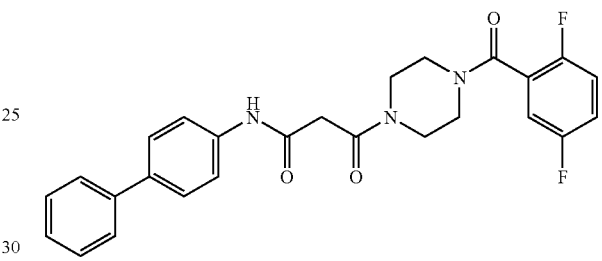

HOBt (34 mg, 0.25 mmol) and DIPEA (67.9 mg, 0.51 mmol) were added to a stirred solution of 2,5-difluorobenzoic acid (34 mg, 0.21 mmol) in DMF (2 mL). The reaction mixture was cooled to 10° C. and EDCI.HCl (48 mg, 0.25 mmol) followed by N-biphenyl-4-yl-3-oxo-3-piperazin-1-yl-propionamide.hydrochloride (75 mg, 0.2 mmol) were added. The reaction mixture was stirred at room temperature overnight, then diluted with water. The resulting precipitate was filtered, then purified by column chromatography using silica gel 60-120 mesh (70% ethyl acetate in hexane) to 36 mg (37%) of N-Biphenyl-4-yl-3-[4-(2,5-difluoro-benzoyl)-piperazin-1-yl]-3-oxo-propionamide. LCMS: 464.17 (M+1)$^+$, 97.6%, $^1$H NMR: (CDCl$_3$): δ 9.6 (d, 1H), 7.6 (m, 6H), 7.42 (t, 2H), 7.34 (t, 1H), 7.12 (m, 3H), 3.85 (d, 3H), 3.7 (m, 3H), 3.55 (d, 2H), 3.4 (m, 2H).

Example 7

Synthesis of N-Biphenyl-4-yl-3-[4-(2-bromo-5-fluoro-benzoyl)-piperazin-1-yl]-3-oxo-propionamide

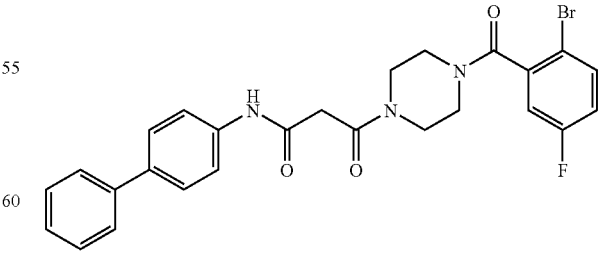

HOBt (34 mg, 0.25 mmol) and DIPEA (67.9 mg, 0.51 mmol) were added to a stirred solution of 2-bromo-5-fluorobenzoic acid (46 mg, 0.21 mmol) in DMF (2 mL). The reaction mixture was cooled to 10° C. and EDCI.HCl (48 mg, 0.25 mmol) followed by N-biphenyl-4-yl-3-oxo-3-piperazin-1-yl-propionamide hydrochloride (75 mg, 0.2 mmol) were added. The reaction mixture was stirred at room temperature overnight, then diluted with water. The resulting precipitate was filtered, then purified by column chromatography using silica gel 60-120 mesh (80% ethyl acetate in hexane) to afford 40 mg (37%) of N-biphenyl-4-yl-3-[4-(2-bromo-5-fluoro-benzoyl)-piperazin-1-yl]-3-oxo-propionamide. LCMS: 524.09 (M+1)+, 96%. ¹H NMR: (CDCl₃): δ 9.6 (d, 1H), 7.6 (m, 7H), 7.42 (t, 2H), 7.34 (t, 1H), 7.0 (m, 2H), 3.96 (m, 2H), 3.7 (m, 4H), 3.5 (d, 2H), 3.3 (m, 2H).

Example 8

Synthesis of N-Biphenyl-4-yl-3-oxo-3-[4-(3,4,5-trifluoro-benzoyl)-piperazin-1-yl]-propionamide

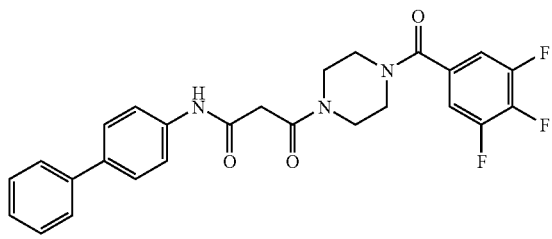

HOBt (34 mg, 0.25 mmol) and DIPEA (67.9 mg, 0.51 mmol) were added to a stirred solution of 3,4,5-trifluorobenzoic acid (37 mg, 0.21 mmol) in DMF (2 mL). The reaction mixture was cooled to 10° C. and EDCI.HCl (48 mg, 0.25 mmol) followed by N-biphenyl-4-yl-3-oxo-3-piperazin-1-yl-propionamide hydrochloride (75 mg, 0.2 mmol) were added. The reaction mixture was stirred at room temperature overnight then diluted with water. The resulting precipitate was filtered and purified by column chromatography using silica gel 60-120 mesh (40% ethyl acetate in hexane) to afford 42 mg (42%) of N-Biphenyl-4-yl-3-oxo-3-[4-(3,4,5-trifluoro-benzoyl)-piperazin-1-yl]-propionamide. LCMS: 482.16 (M+1)+ 94.2%, ¹H NMR: (CDCl₃): δ 9.5 (s, 1H), 7.58 (m, 6H), 7.43 (t, 2H), 7.34 (m, 1H), 7.08 (t, 2H), 3.7 (bs, 8H), 3.54 (s, 2H).

Example 9

Synthesis of N-Biphenyl-4-yl-3-[4-(2-chloro-5-trifluoromethyl-benzoyl)-piperazin-1-yl]-3-oxo-propionamide

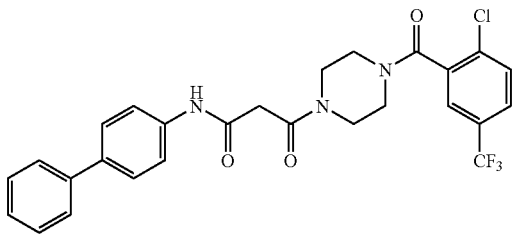

HOBt (34 mg, 0.25 mmol) and DIPEA (67.9 mg, 0.51 mmol) were added to a stirred solution of 2-chloro-5-trifluoromethylbenzoic acid (48 mg, 0.21 mmol) in DMF (3 mL). The reaction mixture was cooled to 10° C. and EDCI.HCl (48 mg, 0.25 mmol) followed by N-biphenyl-4-yl-3-oxo-3-piperazin-1-yl-propionamide hydrochloride (75 mg, 0.2 mmol) were added. The reaction mixture was stirred at room temperature overnight then diluted with water and extracted with ethyl acetate. The ethyl acetate was washed with brine solution, dried over Na₂SO₄ and evaporated. The residue was purified by column chromatography using silica gel 60-120 mesh (60% ethyl acetate in hexane) to afford 53 mg (48%) of N-biphenyl-4-yl-3-[4-(2-chloro-5-trifluoromethyl-benzoyl)-piperazin-1-yl]-3-oxo-propionamide. LCMS: 530.14 (M+1)+ 98.5%, ¹H NMR: (CDCl₃): δ 9.6 (d, 1H), 7.6 (m, 8H), 7.43 (t, 2H), 7.33 (t, 1H), 4.0 (m, 2H), 3.7 (m, 4H), 3.5 (d, 2H), 3.3 (m, 2H).

Example 10

Synthesis of N-Biphenyl-4-yl-3-[4-(2-bromo-benzoyl)-piperazin-1-yl]-3-oxo-propionamide

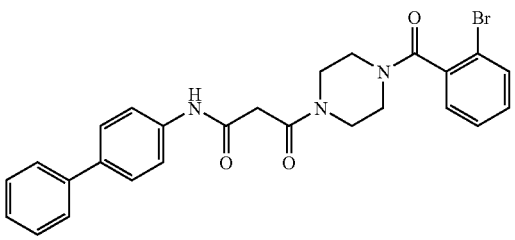

HOBt (34 mg, 0.25 mmol) and DIPEA (67.9 mg, 0.51 mmol) were added to a stirred solution of 2-bromobenzoic acid (42 mg, 0.21 mmol) in DMF (2 mL). The reaction mixture was cooled to 10° C. and EDCI.HCl (48 mg, 0.25 mmol) followed by N-biphenyl-4-yl-3-oxo-3-piperazin-1-yl-propionamide hydrochloride (75 mg, 0.2 mmol) were added. The reaction mixture was stirred at room temperature overnight, then diluted with water and the product extracted with ethyl acetate. The ethyl acetate was washed with brine solution, dried over Na₂SO₄ and evaporated. The residue was purified by column chromatography using silica gel 60-120 mesh (80% ethyl acetate in hexane) to afford 35 mg (33%) of N-biphenyl-4-yl-3-[4-(2-bromo-benzoyl)-piperazin-1-yl]-3-oxo-propionamide. LCMS: 506.10 (M+1)+ 96.5%, ¹H NMR: (CDCl₃): δ 9.6 (d, 1H), 7.6 (m, 6H), 7.35 (m, 5H), 4.0 (m, 1H), 3.74 (m, 4H), 3.54 (d, 2H), 3.3 (m, 2H).

Example 11

Synthesis of N-Biphenyl-4-yl-3-[4-(2,4-dichloro-5-fluoro-benzoyl)-piperazin-1-yl]-3-oxo-propionamide

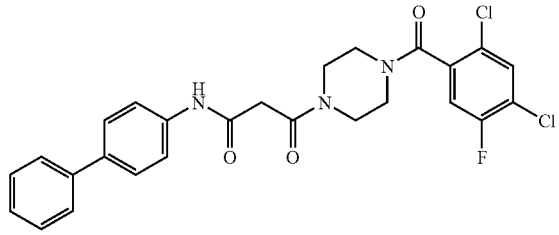

HOBt (23 mg, 0.17 mmol) and DIPEA (44.8 mg, 0.35 mmol) were added to a stirred solution of 2,4-dichloro-5-fluorobenzoic acid (29 mg, 0.14 mmol) in DMF (1 mL). The reaction mixture was cooled to 10° C. and EDCI.HCl (33 mg, 0.17 mmol) followed by N-biphenyl-4-yl-3-oxo-3-piperazin-1-yl-propionamide hydrochloride (50 mg, 0.14 mmol) were added. The reaction mixture was stirred at room temperature overnight, then diluted with water. The resulting precipitate was filtered to afford 50 mg (70%) of N-biphenyl-4-yl-3-[4-(2,4-dichloro-5-fluoro-benzoyl)-piperazin-1-yl]-3-oxo-propionamide. LCMS: 514.11 (M+1)+ 100%. ¹H NMR: (CDCl₃): δ 9.6 (d, 1H), 7.6 (m, 7H), 7.44 (t, 2H), 7.34 (t, 1H), 7.14 (d, 1H), 3.96 (bs, 2H), 3.72 (m, 4H), 3.54 (d, 2H), 3.34 (m, 2H).

Example 12

Synthesis of N-Biphenyl-4-yl-3-[4-(2-fluoro-benzoyl)-piperazin-1-yl]-3-oxo-propionamide

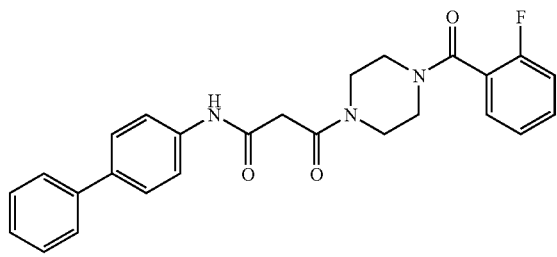

HOBt (34 mg, 0.25 mmol) and DIPEA (67.9 mg, 0.51 mmol) were added to a stirred solution of 2-fluorobenzoic acid (29 mg, 0.21 mmol) in DMF (1.5 mL). The reaction mixture was cooled to 10° C. and EDCI.HCl (48 mg, 0.25 mmol) followed by N-biphenyl-4-yl-3-oxo-3-piperazin-1-yl-propionamide hydrochloride (75 mg, 0.2 mmol) were added. The reaction mixture was stirred at room temperature overnight then diluted with water. The resulting precipitate was dried to afford 87 mg (94%) of N-biphenyl-4-yl-3-[4-(2-fluoro-benzoyl)-piperazin-1-yl]-3-oxo-propionamide. LCMS: 446.18 (M+1)+ 93.2%, ¹H NMR: (CDCl₃): δ 9.7 (d, 1H), 7.6 (m, 6H), 7.44 (t, 4H), 7.34 (t, 1H), 7.22 (m, 1H), 7.14 (t, 1H), 3.86 (m, 6H), 3.54 (d, 2H), 3.4 (bs, 2H).

Example 13

Synthesis of N-Biphenyl-4-yl-3-[4-(3-fluoro-benzoyl)-piperazin-1-yl]-3-oxo-propionamide

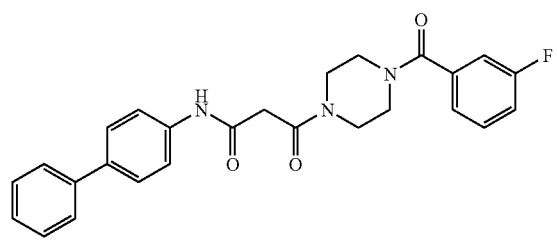

HOBt (34 mg, 0.25 mmol) and DIPEA (67.9 mg, 0.51 mmol) were added to a stirred solution of 3-fluorobenzoic acid (29 mg, 0.21 mmol) in DMF (1.5 mL). The reaction mixture was cooled to 10° C. and EDCI.HCl (48 mg, 0.25 mmol) followed by N-biphenyl-4-yl-3-oxo-3-piperazin-1-yl-propionamide hydrochloride (75 mg, 0.2 mmol) were added. The reaction mixture was stirred at room temperature overnight then diluted with water. The resulting precipitate was filtered and dried to afford 91 mg (98%) of N-biphenyl-4-yl-3-[4-(3-fluoro-benzoyl)-piperazin-1-yl]-3-oxo-propionamide. LCMS: 446.18 (M+1)+ 98.1%, ¹H NMR: (CDCl₃): δ 9.6 (s, 1H), 7.6 (m, 6H), 7.46 (m, 3H), 7.34 (m, 1H), 7.16 (m, 3H), 3.7 (bs, 7H), 3.54 (s, 3H).

Example 14

Synthesis of N-Biphenyl-4-yl-3-[4-(4-fluoro-benzoyl)-piperazin-1-yl]-3-oxo-propionamide

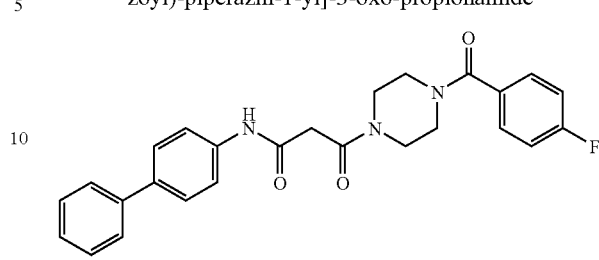

HOBt (34 mg, 0.25 mmol) and DIPEA (67.9 mg, 0.51 mmol) were added to a stirred solution of 4-fluorobenzoic acid (29 mg, 0.21 mmol) in DMF (1.5 mL). The reaction mixture was cooled to 10° C. and EDCI.HCl (48 mg, 0.25 mmol) followed by N-biphenyl-4-yl-3-oxo-3-piperazin-1-yl-propionamide.hydrochloride (75 mg, 0.2 mmol) were added. The reaction mixture was stirred at room temperature overnight, then diluted with water. The resulting precipitate was filtered to afford 90 mg (97%) of N-biphenyl-4-yl-3-[4-(4-fluoro-benzoyl)-piperazin-1-yl]-3-oxo-propionamide. LCMS: 446.18 (M+1)+, 97.9%. ¹H NMR: (CDCl₃): δ 9.8 (s, 1H), 7.6 (m, 6H), 7.44 (m, 3H), 7.34 (t, 1H), 7.14 (t, 2H), 3.7 (m, 10H).

Example 15

Synthesis of N-Biphenyl-4-yl-3-oxo-3-[4-(2-trifluoromethyl-benzyl)-piperazin-1-yl]-propionamide

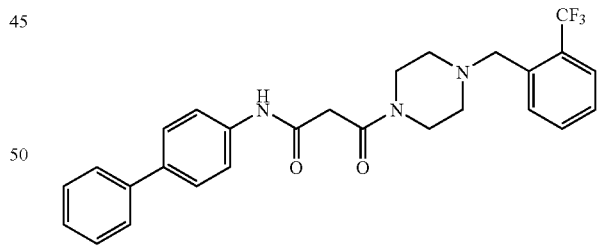

A solution of N-Biphenyl-4-yl-3-oxo-3-piperazin-1-yl-propionamide hydrochloride (75 mg, 0.2 mmol) and K₂CO₃ (58 mg, 0.42 mmol) in DMF (2 mL) was stirred for 15 minutes at room temperature, then cooled to 0° C. and 1-bromomethyl-2-trifluoromethyl-benzene (50 mg, 0.21 mmol) was added. The resulting mixture was stirred at room temperature for 6 hours then diluted with water. The resulting precipitate was filtered to afford 85 mg (85%) of N-biphenyl-4-yl-3-oxo-3-[4-(2-trifluoromethyl-benzyl)-piperazin-1-yl]-propionamide. LCMS: 482.2 (M+1)+, 98.8%. ¹H NMR: (CDCl₃): δ 10.0 (s, 1H), 7.76 (d, 1H), 7.66 (d, 3H), 7.58 (m, 5H), 7.44 (t, 2H), 7.34 (m, 2H), 3.7 (m, 4H), 3.6 (t, 2H), 3.48 (s, 2H).

Example 16

Synthesis of N-Biphenyl-4-yl-3-[4-(2-chloro-benzenesulfonyl)-piperazin-1-yl]-3-oxo-propionamide

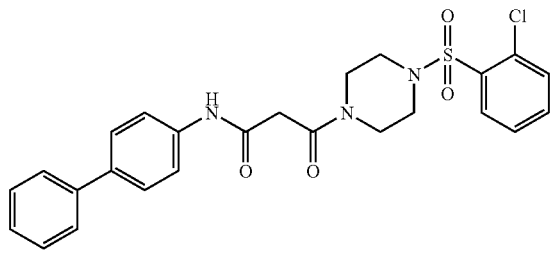

2-Chlorobenzenesulfonyl chloride (35.4 mg, 0.17 mmol) was added at 0° C. to a stirred solution of N-biphenyl-4-yl-3-oxo-3-piperazin-1-yl-propionamide hydrochloride (60 mg, 0.17 mmol) and DIEA (24.6 mg, 0.19 mmol) in dichloromethane (2 mL). the resulting mixture was stirred for 2 hrs then the product was extracted with dichloromethane. The organics was separated and washed with saturated sodium bicarbonate solution, followed by brine, dried over $Na_2SO_4$ and evaporated to dryness. The residue was purified by column chromatography using silica gel 60-120 mesh with 60% ethyl acetate in hexane as eluant to afford 30 mg (36%) of N-Biphenyl-4-yl-3-[4-(2-chloro-benzenesulfonyl)-piperazin-1-yl]-3-oxo-propionamide. LCMS: 498.12 $(M+1)^+$ 96.7%. $^1$H NMR: ($CDCl_3$): δ 9.6 (s, 1H), 8.06 (d, 1H), 7.56 (m, 8H), 7.42 (t, 3H), 7.34 (t, 1H), 3.78 (t, 2H), 3.7 (t, 2H), 3.48 (s, 2H), 3.38 (m, 4H).

Synthesis of 4-(2-Ethoxycarbonyl-acetyl)-piperazine-1-carboxylic acid tert-butyl ester

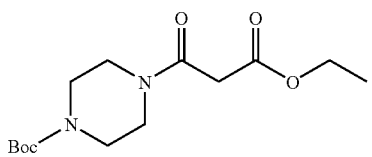

HOBt (3.48 g, 25.8 mmol) and DIPEA (6.94 g, 53.8 mmol) were added to a stirred solution of malonic acid monoethyl ester (2.84 g, 21.5 mmol) in DMF (10 mL). The reaction mixture was cooled to 10° C. and EDCI.HCl (4.95 g, 25.8 mmol) followed by piperazine-1-carboxylic acid tert-butyl ester (4 g, 21.5 mmol) were added. The reaction mixture was stirred at room temperature overnight then diluted with water. The product was extracted with ethyl acetate and the ethyl acetate was washed with brine solution, dried over $Na_2SO_4$ and concentrated to afford 5.2 g (84%) of 4-(2-ethoxycarbonyl-acetyl)-piperazine-1-carboxylic acid tert-butyl ester. LCMS: 301.17 $(M+1)^+$ 84.5%. $^1$H NMR: ($CDCl_3$): δ 4.0 (q, 2H), 3.45 (m, 2H), 3.3 (m, 8H), 1.25 (s, 9H), 1.1 (t, 3H).

Synthesis of 3-Oxo-3-piperazin-1-yl-propionic acid ethyl ester hydrochloride

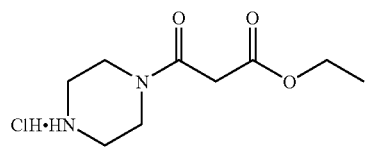

Dioxane.HCl (8 mL) was added to a stirred solution of 4-(2-ethoxycarbonyl-acetyl)-piperazine-1-carboxylic acid tert-butyl ester (5 g, 17 mmol) in dioxane (5.0 mL) at 0° C. and the resulting mixture stirred for 30 minutes. The mixture was then concentrated and the residue was washed with diethyl ether and dried to afford 4.1 g (82%) of 3-oxo-3-piperazin-1-yl-propionic acid ethyl ester hydrochloride. LCMS: 237.1 $(M+1)^+$ 82%

Synthesis of 3-Oxo-3-[4-(2-trifluoromethyl-benzoyl)-piperazin-1-yl]-propionic acid ethyl ester

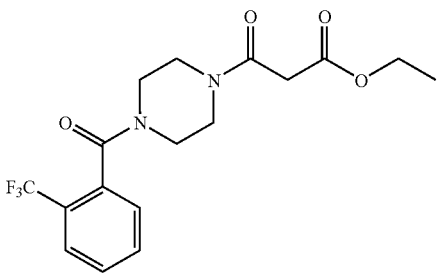

HOBt (1.38 g, 10.2 mmol) and DIPEA (3.68 mL, 21.3 mmol) were added to a stirred solution of 2-trifluoromethyl-benzoic acid (1.62 g, 8.5 mmol) in DMF (5 mL). The reaction mixture was cooled to 10° C. and EDCI.HCl (1.96 g, 10.2 mmol) followed by 3-oxo-3-piperazin-1-yl-propionic acid ethyl ester hydrochloride (2 g, 8.5 mmol) were added. The reaction mixture was stirred at the room temperature overnight, then diluted with water and the product extracted with Ethyl acetate. The ethyl acetate was washed with brine solution, dried over $Na_2SO_4$ and evaporated to dryness. The residue was purified by column chromatography using silica gel 60-120 mesh (50% ethyl acetate in hexane) to afford 1.5 g (48%) of 3-oxo-3-[4-(2-trifluoromethyl-benzoyl)-piperazin-1-yl]-propionic acid ethyl ester. LCMS: 373.13 $(M+1)^+$, 90%

Synthesis of 3-Oxo-3-[4-(2-trifluoromethyl-benzoyl)-piperazin-1-yl]-propionic acid

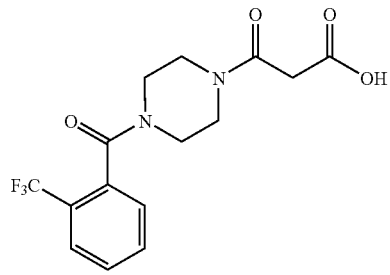

LiOH.$H_2O$ (400 mg, 9.5 mmol) was added to a solution of 3-oxo-3-[4-(2-trifluoromethyl-benzoyl)-piperazin-1-yl]-propionic acid ethyl ester (1.4 g, 3.8 mmol) in methanol (10 mL), THF (4 mL) and $H_2O$ (10 mL) and the resulting mixture was stirred for 2 hours at room temperature. The mixture was and the residue was diluted with water, washed with diethyl ether, acidified with concentrated HCl, extracted with ethyl acetate and evaporated to dryness. The residue was recrystallized from hexane to afford 1.2 g (92%) of 3-oxo-3-[4-(2-trifluoromethyl-benzoyl)-piperazin-1-yl]-propionic acid. LCMS: 345.1 $(M+1)^+$, 96%

Example 17

Synthesis of N-Biphenyl-3yl-3-oxo-[4-(2-trifluoromethyl-benzoyl)-piperazin-1-yl]-propionamide

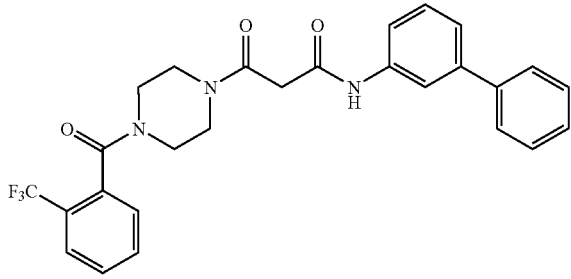

HOBt (44 mg, 0.3 mmol) and DMAP (47 mg, 0.38 mmol) were added to a stirred solution of 3-oxo-3-[4-(2-trifluoromethyl-benzoyl)-piperazin-1-yl]-propionic acid (102 mg, 0.29 mmol) in DMF (5 mL). The reaction mixture was cooled to 10° C. and EDCI.HCl (68 mg, 0.35 mmol) followed by biphenyl-3-yl-amine (55 mg, 0.32 mmol) were added. The reaction mixture was stirred at room temperature overnight, then diluted with water and the product extracted with ethyl acetate. The ethyl acetate was washed with brine solution, dried over $Na_2SO_4$ and concentrated. The residue was purified by column chromatography using silica gel 60-120 mesh using 70% ethyl acetate in hexane to afford 64 mg (44%) of N-biphenyl-3yl-3-oxo-[4-(2-trifluoromethyl-benzoyl)-piperazin-1-yl]-propionamide. LCMS: 496.18 (M+1)$^+$, 98.7%. $^1$H NMR: (DMSO-d$_6$): δ10.2 (d, 2H), 7.94-7.8 (dd, 2H), 7.8 (t, 1H), 7.7-7.52 (m, 5H), 7.52 (t, 2H), 7.42-7.32 (bs, 3H), 3.86-3.5 (m, 6H), 3.5-3.38 (m, 2H), 3.22 (d, 2H).

Synthesis of 5-phenyl-pyridin-2-ylamine

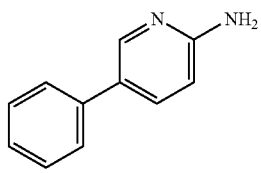

A mixture of toluene (15 mL) and water (5 mL) was degassed with argon gas for 5 minutes. Sodium carbonate (481 mg, 4.5 mmol) was added and the resulting mixture was again degassed with argon gas for 5 minutes. Phenyl boronic acid (353 mg, 2.7 mmol) and 5-iodo-pyridin-2-ylamine (500 mg, 2.27 mmol) were added and the mixture was again degassed with argon gas for 5 minutes. Tetrakis palladium triphenyl phosphine (525 mg, 4.5 mmol) was then added and the mixture was again degassed with argon gas for 5 minutes. The resulting mixture was heated to reflux for 3 hours. The mixture was then diluted with ethyl acetate and washed with water followed by brine solution. The ethyl acetate layer was collected, dried over sodium sulphate and concentrated under reduced pressure. The resulting residue was purified by column chromatography using silica gel 60-120 mesh (35% ethyl acetate in hexane) to afford 10 mg (28%) of 5-phenyl-pyridin-2-ylamine. LCMS: 171.09 (M+1)$^+$, 60.5%.

Example 18

Synthesis of 3-Oxo-N-(5-phenyl-pyridin-2-yl)-3-[4-(2-trifluoromethyl-benzoyl)-piperazin-1-yl]-propionamide

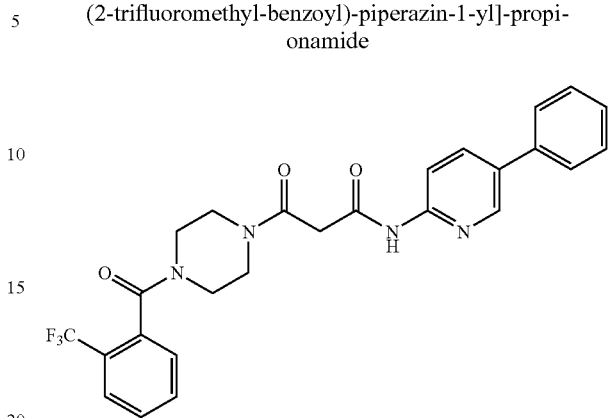

HOBt (57 mg, 0.42 mmol) and DMAP (46 mg, 0.38 mmol) were added to a stirred solution of 3-oxo-3-[4-(2-trifluoromethyl-benzoyl)-piperazin-1-yl]-propionic acid (60 mg, 0.35 mmol) in DMF (2 mL). The reaction mixture was cooled to 10° C. and EDCI.HCl (81 mg, 0.42 mmol) followed by 5-phenyl-pyridin-2-ylamine (120 mg, 0.35 mmol) were added. The reaction mixture was stirred at the room temperature overnight, then diluted with water and the product extracted with ethyl acetate. The ethyl acetate was washed with brine solution, dried over $Na_2SO_4$ and evaporated. The residue was purified by column chromatography using silica gel 60-120 mesh and 80% ethyl acetate in hexane as the eluant to afford 65 mg (38% 0 of 3-oxo-N-(5-phenyl-pyridin-2-yl)-3-[4-(2-trifluoromethyl-benzoyl)-piperazin-1-yl]-propionamide. LCMS: 497.18 (M+1)$^+$, 90.4%, $^1$H NMR: (CDCl$_3$): δ 9.6 (d, 1H), 8.5 (s, 1H), 8.2 (m, 1H), 7.9 (m, 1H), 7.75 (d, 1H), 7.6 (m, 4H), 7.45 (t, 2H), 7.35 (m, 2H), 4.0 (m, 2H), 3.7 (m, 3H), 3.55 (m, 4H), 3.26 (m, 2H).

Synthesis of N-Hydroxy-4-nitro-benzamidine

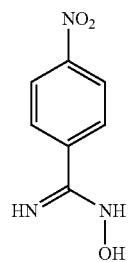

Hydroxylamine hydrochloride (1.9 g, 27.2 mmol) then sodium carbonate (2.2 g, 20.4 mmol) were added to a stirred solution of 4-nitro-benzonitrile (1 g, 6.8 mmol) in ethanol (20 mL) and water (8 mL). The resulting mixture was refluxed at 85° C. under an atmosphere of nitrogen for 2 hours. The volatiles were then evaporated and the residue was extracted with ethyl acetate. The organics were washed with brine solution, dried over $Na_2SO_4$ and evaporated to afford 1.2 g (98%) of N-hydroxy-4-nitro-benzamidine. $^1$H NMR: (DMSO-d$_6$): δ 10.2 (s, 1H), 8.24 (d, 2H), 7.97 (d, 2H), 6.03 (s, 2H).

Synthesis of 3-(4-Nitro-phenyl)-[1,2,4]oxadiazole

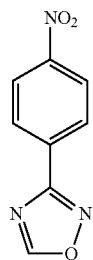

Triethyl orthoformate (2.93 g, 19.8 mmol) was added to a stirred solution of N-hydroxy-4-nitro-benzamidine (1.2 g, 6.6 mmol) in THF (15 mL). The mixture was cooled to 0° C. and boron triflouride dimethyl ether (900 mg, 7.9 mmol) was added drop wise. The mixture was maintained at room temperature for three hours. The volatiles were evaporated and the residue was washed with ether and dried to afford 650 mg (55%) of 3-(4-nitro-phenyl)-[1,2,4]oxadiazole.

Synthesis of 4-[1,2,4]Oxadiazol-3-yl-phenylamine

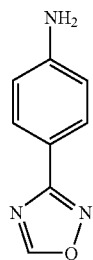

Ammonium chloride (214 mg, 4 mmol) in water (5 mL) was added to a stirred solution of 3-(4-nitro-phenyl)-[1,2,4]oxadiazole (200 mg, 1 mmol) in THF (15 mL). Zinc powder (262 mg, 4 mmol) was then added portion wise. The reaction was stirred at room temperature for 1 hour and then refluxed at 65° C. for 5 hours. The mixture was filtered over celite, the filtrate was evaporated and the residue was extracted with ethyl acetate. The ethyl acetate was washed with brine solution, dried over $Na_2SO_4$ and evaporated to afford 155 mg (92%) of 4-[1,2,4]oxadiazol-3-yl-phenylamine. $^1$H NMR: (DMSO-$d_6$): δ 9.5 (s, 1H), 7.7 (d, 2H), 6.7 (d, 2H), 5.8 (s, 2H).

Example 19

Synthesis of N-(4-[1,2,4]Oxadiazol-3-yl-phenyl)-3-oxo-3-[4-(2-trifluoromethyl-benzoyl)-piperazin-1-yl]-propionamide

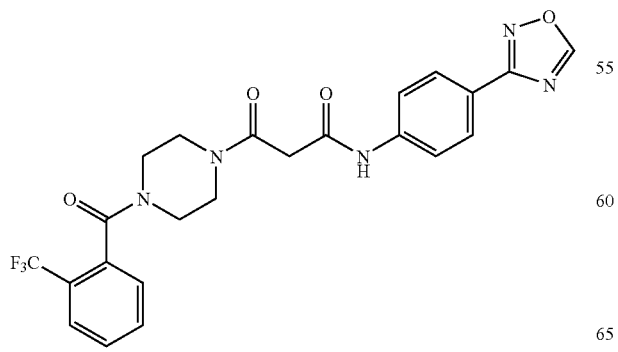

HOBt (153 mg, 1.13 mmol) and DMAP (172 mg, 1.4 mmol) were added to a stirred solution of 3-oxo-3-[4-(2-trifluoromethyl-benzoyl)-piperazin-1-yl]-propionic acid (325 mg, 9.45 mmol) in DMF (2 mL). The reaction mixture was cooled to 10° C. and EDCI.HCl (217 mg, 1.13 mmol) followed by 4-[1,2,4]oxadiazol-3-yl-phenylamine-2-yl-amine (152 mg, 9.4 mmol) were added. The reaction mixture was stirred at the room temperature overnight then diluted with water and the product extracted with ethyl acetate. The organics were washed with brine solution, dried over $Na_2SO_4$ and evaporated. The residue was washed with ether and dried to afford 220 mg (48%) of N-(4-[1,2,4]oxadiazol-3-yl-phenyl)-3-oxo-3-[4-(2-trifluoromethyl-benzoyl)-piperazin-1-yl]-propionamide. LCMS: 488.15 (M+1)$^+$, 96.97%. $^1$H NMR: (CDCl$_3$): δ 10.0 (d, 1H), 8.74 (s, 1H), 8.08 (d, 2H), 7.7 (m, 3H), 7.6 (m, 2H), 7.34 (d, 1H), 4.02 (m, 2H), 3.7 (m, 3H), 3.5 (m, 4H), 3.26 (m, 2H).

Synthesis of 4-Nitro-benzoic acid N'-acetyl-hydrazide

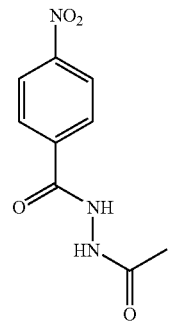

HOBt (972 mg, 7.2 mmol) and DIEA (1.14 g, 8.9 mmol) were added to a stirred solution of 4-nitro-benzoic acid (1 g, 5.96 mmol) in DMF (6 mL). The reaction mixture was cooled to 10° C. EDCI.HCl (1.38 g, 7.2 mmol) followed by acetic acid hydrazide (490 mg, 6.6 mmol) were added. The reaction mixture was stirred at room temperature overnight then diluted with water and the product extracted with ethyl acetate. The organics were washed with saturated sodium bicarbonate solution followed by brine solution, dried over $Na_2SO_4$ and evaporated to afford 700 mg (55%) of 4-nitro-benzoic acid N'-acetyl-hydrazide. $^1$H NMR: (DMSO-$d_6$): δ 10.7 (s, 1H), 10.0 (s, 1H), 8.4 (d, 2H), 8.1 (d, 2H), 1.9 (s, 3H).

Synthesis of 2-Methyl-5-(4-nitro-phenyl)-[1,3,4]oxadiazole

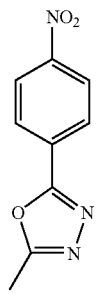

A solution of 4-nitro-benzoic acid N'-acetyl-hydrazide (200 mg, 8.9 mmol) in distilled POCl$_3$ (4 mL) was refluxed at 110° C. under nitrogen for 6 hours. The reaction mixture was concentrated and the residue was quenched with 10% NaOH solution. The resulting precipitate was collected by filtration to afford 160 mg (89%) of 2-Methyl-5-(4-nitro-phenyl)-[1,3,4]oxadiazole. $^1$H NMR: (CDCl$_3$): δ 8.38 (d, 2H), 8.24 (d, 2H), 2.7 (s, 3H).

Synthesis of 4-(5-Methyl-[1,3,4]oxadiazol-2-yl)-phenyl amine

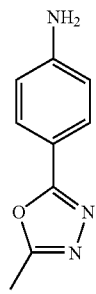

Ammonium chloride (1.12 g, 21 mmol) in water (5 mL) was added to a stirred solution of 2-methyl-5-(4-nitro-phenyl)-[1,3,4]oxadiazole (530 mg, 2.6 mmol) in THF (10 mL). Zinc powder (1.4 g, 21 mmol) was added portion wise and the mixture was stirred at room temperature for 1 hour then heated to reflux at 65° C. for 5 hours. The mixture was then filtered over celite and the filtrate was concentrated. The residue was extracted with ethyl acetate and the organics were washed with brine solution, dried over Na$_2$SO$_4$ and concentrated. The residue was purified by column chromatography using basic alumina (4% methanol in chloroform) to afford 220 mg (48%) of 4-(5-methyl-[1,3,4]oxadiazol-2-yl)-phenyl amine. $^1$H NMR: (CDCl$_3$): δ 7.8 (d, 2H), 6.7 (d, 2H), 4.0 (s, 2H), 2.6 (s, 3H).

Example 20

Synthesis of N-[4-(5-Methyl-[1,3,4]oxadiazol-2-yl)-phenyl]-3-oxo-3-[4-(2-trifluoromethyl-benzoyl)-piperazin-1-yl]-propionamide

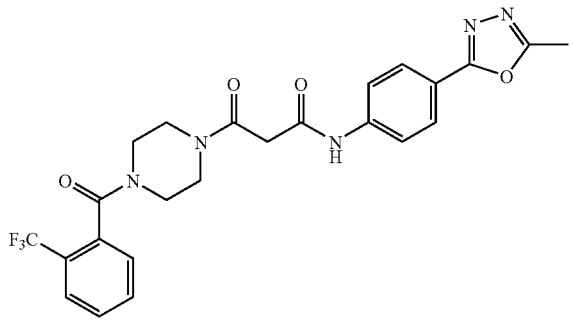

HOBt (72 mg, 0.53 mmol) and DMAP (81 mg, 0.66 mmol) were added to a stirred solution of 3-oxo-3-[4-(2-trifluoromethyl-benzoyl)-piperazin-1-yl]-propionic acid (150 mg, 0.44 mmol) in DMF (2 mL). The reaction mixture was cooled to 10° C. and EDCI.HCl (102 mg, 0.53 mmol) followed by 4-(5-methyl-[1,3,4]oxadiazol-2-yl)-phenylamine (77 mg, 0.44 mmol) were added. The reaction mixture was stirred at room temperature overnight then diluted with water and the product extracted with ethyl acetate. The organics were washed with brine solution, dried over Na$_2$SO$_4$ and concentrated. The residue was purified by column chromatography using basic alumina (80% ethyl acetate in hexane) to afford 40 mg (20%) of N-[4-(5-methyl-[1,3,4]oxadiazol-2-yl)-phenyl]-3-oxo-3-[4-(2-trifluoromethyl-benzoyl)-piperazin-1-yl]-propionamide. LCMS: 502.17 (M+1)$^+$, 94.56%, $^1$H NMR: (DMSO-d$_6$): δ 10.5 (d, 1H), 7.92 (m, 2H), 7.8 (m, 4H), 7.68 (t, 1H), 7.56 (m, 1H), 3.68 (m, 7H), 3.44 (m, 2H), 3.18 (m, 1H), 3.08 (m, 1H), 2.58 (s, 3H).

Synthesis of 2-Benzyloxy-pyridine

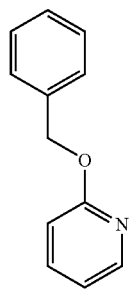

2-Chloro-pyridine (5 g, 44 mmol) was added to a stirred solution of benzylalcohol (6.1 g, 57.2 mmol), KOH (2.9 g, 52.8 mmol) and 18 crown[6] (50 mg) in toluene (20 mL) and the resulting mixture was heated to reflux at 110° C. for 6 hours. The reaction mixture was then cooled to room temperature and concentrated. The residue was diluted with waster and extracted with ethyl acetate. The organic layer was washed with brine solution, dried over Na$_2$SO$_4$ and concentrated to afford 1.85 g (22%) of 2-benzyloxy-pyridine.

Synthesis of 2-Benzyloxy-5-nitro-pyridine

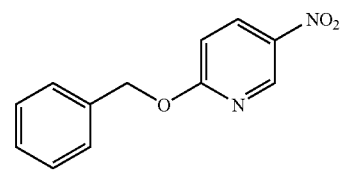

Benzyl alcohol (682 mg, 6.3 mmol), 18 crown ether (2.5 g, 9.4 mmol) and KOH (637 mg, 11.3 mmol) were added to a solution of 2-chloro-5-nitro-pyridine (1 g, 6.3 mmol) in toluene (15 mL) and the reaction mixture was maintained at 80° C. for 2 hours, then diluted with ethyl acetate. The organic layer was washed with brine solution, dried over Na$_2$SO$_4$ and evaporated. The residue was purified by column chromatography using neutral alumina (2% ethyl acetate in hexane) to afford 410 mg (28%) of 2-benzyloxy-5-nitro-pyridine. LCMS: 231.07 (M+1)$^+$, 98.4%

Synthesis of 6-Benzyloxy-pyridin-3-ylamine

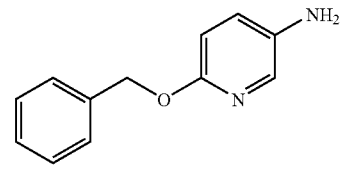

Ammonium chloride (325 mg, 6.0 mmol) in water (10 mL) was added to a solution of 2-benzyloxy-5-nitro-pyridine (350 mg, 1.5 mmol) in THF (15 mL) and the resulting mixture stirred at 75° C. for 30 minutes. Iron powder (340 mg, 6 mmol) was then added portion wise and the mixture stirred for 5 hours at 75° C. The reaction mixture was filtered over celite. The filtrate was basified with sodium bicarbonate solution and the product extracted with ethyl acetate. The organics were washed with brine solution, dried over Na$_2$SO$_4$ and concentrated to afford 320 mg (100%) of 6-benzyloxy-pyridin-3-ylamine.

Example 21

Synthesis of N-(6-Benzyloxy-pyridin-3-yl)-3-oxo-3-[4-(2-trifluoromethyl-benzoyl)-piperazin-1-yl]-propionamide

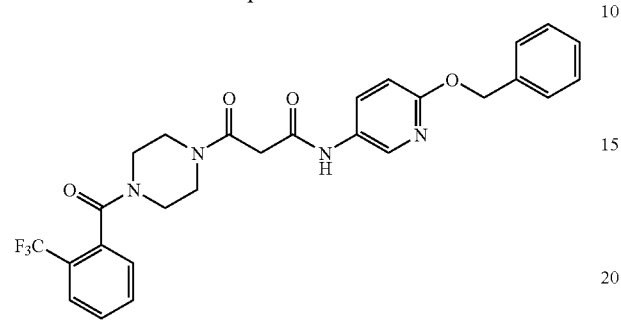

HOBt (43 mg, 0.32 mmol) and DIEA (150 mg, 011 mmol) were added to a stirred solution of 3-oxo-3-[4-(2-trifluoromethyl-benzoyl)-piperazin-1-yl]-propionic acid (100 mg, 0.29 mmol) in DMF (4 mL). The reaction mixture was cooled to 10° C. and EDCI.HCl (111 mg, 0.58 mmol) followed by 6-benzyloxy-pyridin-3-ylamine (81 mg, 0.4 mmol) were added. The reaction mixture was stirred at room temperature overnight then diluted with water and the product extracted with ethyl acetate. The organics were washed with brine solution, dried over Na$_2$SO$_4$ and concentrated to afford a residue which was purified by column chromatography using silica gel 60-120 mesh (80% ethyl acetate in hexane) to afford 60 mg (39%) of N-(5-benzyloxy-pyridin-2-yl)-3-oxo-3-[4-(2-trifluoromethyl-benzoyl)-piperazin-1-yl]-propionamide. LCMS: 527.19 (M+1)$^+$, 98.6%, $^1$H NMR: (DMSO-d$_6$): δ 10.2 (td, 1H), 8.4 (dd, 1H), 8 (dt, 1H), 7.8 (d, 1H), 7.7 (t, 1H), 7.6 (t, 1H), 7.5 (d, 1H), 7.4 (m, 5H), 6.9 (m, 1H), 5.4 (d, 2H), 3.8 (m, 6H), 3.5 (m, 2H), 3.2 (m, 2H).

Synthesis of 5-Nitro-3H-benzooxazol-2-one

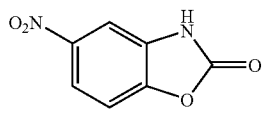

CDI (1.57 g, 19.4 mmol) was added at 0° C. to a stirred solution of 2-amino-4-nitro-phenol (500 mg, 0.6 mmol) in DMF (5 mL) and the resultant was stirred for 30 mins. The mixture was poured onto ice and stirred for 10 minutes. The resulting precipitate was isolated by filtration to afford 470 mg (80%) of 5-nitro-3H-benzooxazol-2-one. $^1$H NMR: (DMSO-d$_6$): δ 12.4 (b s, 1H), 8.05 (dd, 1H), 7.85 (d, 1H), 7.54 (d, 1H).

Synthesis of 5-Amino-3H-benzooxazol-2-one

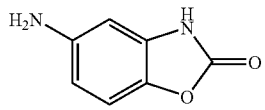

10% Pd/C (50 mg) was added to a stirred solution of 5-nitro-3H-benzooxazol-2-one (450 mg, 2.5 mmol) in MeOH (5 mL) added under an atmosphere of hydrogen and the mixture was stirred for 3 hours. The mixture was then filtered over celite and the filtrate was evaporated to afford 380 mg (95%) of 5-amino-3H-benzooxazol-2-one. $^1$H NMR: (DMSO-d$_6$): δ 6.88 (d, 1H), 6.3 (d, 1H), 6.22 (dd, 1H), 4.5 (s, 2H).

Example 22

Synthesis of 3-Oxo-N-(2-oxo-2,3-dihydro-benzooxazol-5-yl)-3-[4-(2-trifluoromethyl-benzoyl)-piperazin-1-yl]-propionamide

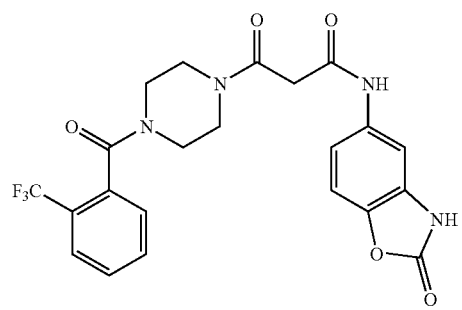

HOBt (72 mg, 0.53 mmol) and DMAP (81 mg, 0.66 mmol) were added to a stirred solution of 3-oxo-3-[4-(2-trifluoromethyl-benzoyl)-piperazin-1-yl]-propionic acid (150 mg, 0.44 mmol) in DMF (2 mL). The reaction mixture was cooled to 10° C. and EDCI.HCl (102 mg, 0.53 mmol) followed by 5-amino-3H-benzooxazol-2-one (66 mg, 0.44 mmol) were added. The reaction mixture was stirred at room temperature overnight then diluted with water and the product extracted with ethyl acetate. The ethyl acetate was washed with brine solution, dried over Na$_2$SO$_4$ and concentrated. The residue was purified by column chromatography using silica gel 60-120 mesh (90% ethyl acetate in hexane) to afford 65 mg (32%) of 3-oxo-N-(2-oxo-2,3-dihydro-benzooxazol-5-yl)-3-[4-(2-trifluoromethyl-benzoyl)-piperazin-1-yl]-propionamide. LCMS: 477.12 (M+1)$^+$, 96.35%, $^1$H NMR: (DMSO-d$_6$): δ 11.6 (s, 1H), 10.2 (d, 1H), 7.8 (q, 2H), 7.6 (m, 3H), 7.22 (m, 1H), 7.08 (t, 1H), 3.74 (m, 1H), 3.6 (s, 2H), 3.52 (s, 1H), 3.32 (s, 1H), 3.16 (m. 1H), 3.8 (m, 1H).

Synthesis of 4-Nitro-benzoyl chloride

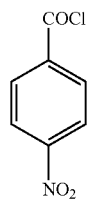

Oxalyl chloride (4.78 g, 37.6 mmol) was added drop wise to a stirred solution of 4-nitrobenzoic acid (4.2 g, 25 mmol) in chloroform (50 mL). After 5 mins DMF (2 drops) was added and the resulting mixture was stirred at room temperature for 2 hours. The solvent was removed to afford 4.7 g (98%) of 4-nitro-benzoyl chloride which was used for next step without further purification.

Synthesis of N-Methyl-4-nitro-benzamide

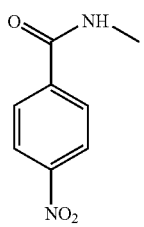

To a mixture of 40% aqueous solution of Methylamine hydrochloride (2.175 g, 33.2 mmol) and Triethyl amine (3.75 g, 37.18 mmol) at 0° C., added 4-Nitro-benzoyl chloride (4.6 g, 24.78 mmol) and stirred for 30 mins. The reaction was monitored by TLC (50% Ethyl acetate in Hexane). The solid precipitate so obtained was filtered, washed with ice cold water and dried to afford 4 g (89%) of N-Methyl-4-nitro-benzamide. $^1$H NMR: (DMSO-d6): δ 8.78 (s, 1H), 8.32 (d, 2H), 8.06 (d, 2H), 2.8 (s, 3H).

Synthesis of 4-Amino-N-methyl-benzamide

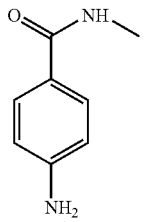

Ammonium chloride (29.6 g, 55.4 mmol) in water (200 mL) and methanol (200 mL) was added to a solution of N-methyl-4-nitro-benzamide (10 g, 55.4 mmol) in THF (160 mL). Zinc powder (29 g, 44.4 mmol) was added portion wise and the mixture stirred for 15 minutes. The reaction mixture was filtered over celite, the filtrate was then concentrated and extracted with ethyl acetate. The organics were washed with brine solution, dried over Na$_2$SO$_4$ and concentrated to afford 7.2 g (86%) of 4-amino-N-methyl-benzamide. $^1$H NMR: (DMSO-d$_6$): δ 7.9 (s, 1H), 7.6 (d, 2H), 6.5 (d, 2H), 5.6 (s, 2H), 2.7 (s, 3H).

Example 23

Synthesis of N-Methyl-4-{3-oxo-3-[4-(2-trifluoromethyl-benzoyl)-piperazin-1-yl]-propionylamino}-benzamide

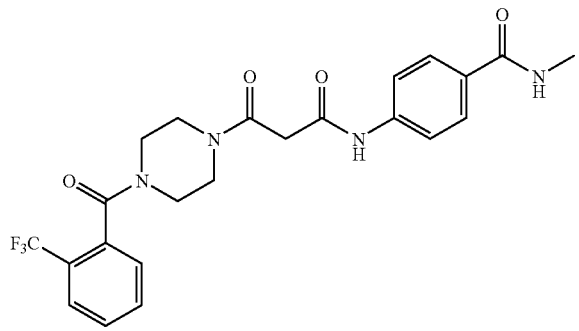

4-Amino-N-methyl-benzamide (40 g, 0.3 mol) was added to a stirred solution of 3-oxo-3-[4-(2-trifluoromethyl-benzoyl)-piperazin-1-yl]-propionic acid (100 mg, 0.3 mmol) and DIC (50 mg, 0.4 mmol) in THF (2 mL) and the mixture was stirred overnight. The resulting precipitate was filtered and extracted with ethyl acetate. The organic layer was washed with brine solution, dried over Na$_2$SO$_4$ and concentrated. The residue was purified by column chromatography using basic alumina (methanol in chloroform) to afford 56 mg (40%) of N-methyl-4-{3-oxo-3-[4-(2-trifluoromethyl-benzoyl)-piperazin-1-yl]-propionylamino}-benzamide. LCMS: 477.17 (M+1)$^+$, 94.5%, $^1$H NMR: (DMSO-d$_6$): δ 7.8 (m, 2H), 7.6 (m, 4H), 7.4 (m, 1H), 4.0 (m, 2H), 3.8 (m, 4H), 3.6 (m, 3H), 3.2 (m, 2H), 3.0 (d, 3H).

Synthesis of 1-(4-Nitro-phenyl)-piperidine

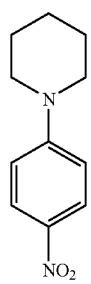

Piperidine (362 mg, 0.2 mmol) was added to a solution of 1-fluoro-4-nitro-benzene (200 mg, 1.4 mmol) in DMSO (10 mL) and the mixture was stirred at 80° C. for 20 hours. The reaction mixture was diluted with water and extracted with ethyl acetate. The organic layer was washed with brine solution, dried over Na$_2$SO$_4$ and concentrated to afford 220 mg (75%) of 1-(4-nitro-phenyl)-piperidine.

Synthesis of 4-Piperidin-1-yl-phenylamine

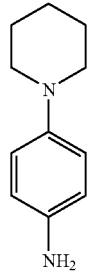

Ammonium chloride (228 mg, 4.2 mmol) in water (4 mL) was added to a solution of 1-(4-nitro-phenyl)-piperidine (220 mg, 1.0 mmol) in THF (6 mL) and the resulting mixture was stirred at 75° C. for 30 minutes. Iron powder (238 mg, 4.2 mmol) was then added portion wise and the mixture stirred for 5 hours at 75° C. The reaction mixture was filtered over celite, the filtrate was basified with sodium bicarbonate solution and the product extracted with ethyl acetate. The organic layer was washed with brine solution, dried over Na$_2$SO$_4$ and concentrated to afford 180 mg (96%) of 4-Piperidin-1-yl-phenylamine. LCMS: 177.13 (M+1)$^+$, 80.6%, $^1$H NMR: (DMSO-d$_6$): δ 6.67 (m, 2H), 6.47 (m, 2H), 4.51 (s, 2H), 2.57 (t, 4H), 1.6 (q, 4H), 1.49 (m, 2H)

Example 24

Synthesis of 3-Oxo-N-(4-piperidin-1-yl-phenyl)-3-[4-(2-trifluoromethyl-benzoyl)-piperazin-1-yl]-propionamide

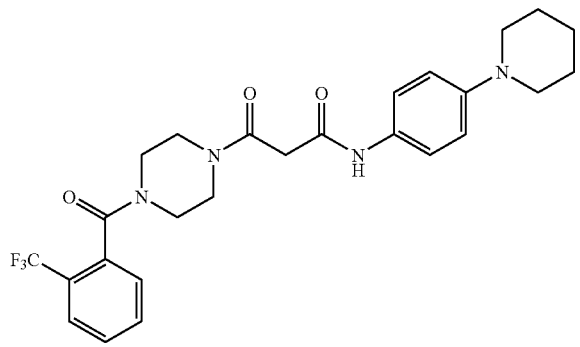

HOBt (43 mg, 0.31 mmol) and DIEA (150 mg, 1.1 mmol) were added to a stirred solution of 3-oxo-3-[4-(2-trifluoromethyl-benzoyl)-piperazin-1-yl]-propionic acid (100 mg, 0.29 mmol) in DMF. The reaction mixture was cooled to 10° C. and EDCI.HCl (111 mg, 0.58 mmol) followed by 4-piperidin-1-yl-phenylamine (61.4 mg, 0.34 mmol) were added. The reaction mixture was stirred at room temperature overnight then diluted with water and the product extracted with ethyl acetate. The ethyl acetate layer was washed with brine solution, dried over $Na_2SO_4$ and concentrated. The residue was purified by column chromatography using silica gel 60-120 mesh (80% ethyl acetate in hexane) to afford 69 mg (47%) of. LCMS: 503.22 (M+1)$^+$, 94.4%, $^1$H NMR: (CDCl$_3$): δ 9.3 (d, 1H), 7.8 (d, 1H), 7.7 (m, 2H), 7.5 (m, 3H), 7.0 (d, 2H), 4.5 (s, 1H), 4.1-3.8 (m, 2H), 3.8-3.6 (m, 3H), 3.6-3.4 (m, 3H), 3.3-3.2 (m, 2H), 3.1 (t, 4H), 1.9-1.7 (m, 7H), 1.6 (q, 2H).

Synthesis of 5-Nitro-2-phenyl-pyridine

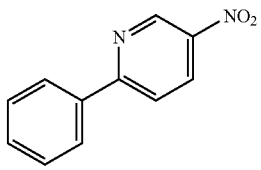

A mixture of toluene (15 mL) and water (5 mL) was degassed with argon for 5 minutes. Sodium carbonate (0.80 g, 4.54 mmol) was added and the mixture was degassed with argon gas for 5 minutes. Phenyl boronic acid (0.59 g, 4.54 mmol) and 2-chloro-5-nitro-pyridine (0.6 g, 3.78 mmol) were added and the mixture was again degassed with argon gas for 5 minutes. Tetrakis palladium triphenyl phosphine (0.88 g, 0.76 mmol) was added and the mixture was degassed with argon gas for 5 minutes. The resulting mixture was heated to reflux for 3 hours. The mixture was then diluted with ethyl acetate, washed with water then brine solution. The organic layer was dried over sodium sulphate and concentrated under reduced pressure to afford a residue which was purified by column chromatography using silica gel 60-120 mesh (5% ethyl acetate in hexane) to afford 0.5 g (66%) of 5-nitro-2-phenyl-pyridine. LCMS purity: 201 (M+1)$^+$, 98.2%, $^1$H NMR (DMSO-d$_6$): δ 9.5 (s, 1H), 8.55 (dd, 1H), 8.1 (m, 2H), 7.9 (d, 1H), 7.55 (m, 3H).

Synthesis of 6-Phenyl-pyridin-3-ylamine

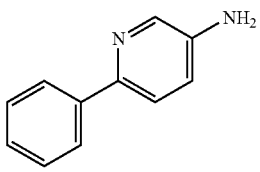

Ammonium chloride (1.1 g, 0.020 mol) dissolved in water (15 mL) was added to a stirred solution of 5-nitro-2-phenyl-pyridine (0.5 g, 2.5 mmol) in THF (10 mL) Methanol (5 mL) was then added, affording a clear solution. Zinc powder (1.3 g, 0.020 mol) was then added portion wise at room temperature and the resulting mixture maintained for 1 hour, then filtered over celite. The filtrate was concentrated and the residue was extracted with ethyl acetate. The organics were washed with brine solution, dried over $Na_2SO_4$ and concentrated under reduced pressure to afford 0.35 g (82%) of 6-phenyl-pyridin-3-ylamine. LCMS purity: 171.08 (M+1)$^+$, 87.9%, $^1$H NMR (DMSO-d$_6$): δ 8.12 (d, 1H), 8.0 (d, 2H), 7.72 (d, 1H), 7.48 (t, 2H), 7.36 (t, 1H), 7.1 (dd, 1H), 5.6 (s, 2).

Example 25

Synthesis of 3-Oxo-N-(6-phenyl-pyridin-3-yl)-3-[4-(2-trifluoromethyl-benzoyl)-piperazin-1-yl]-propionamide

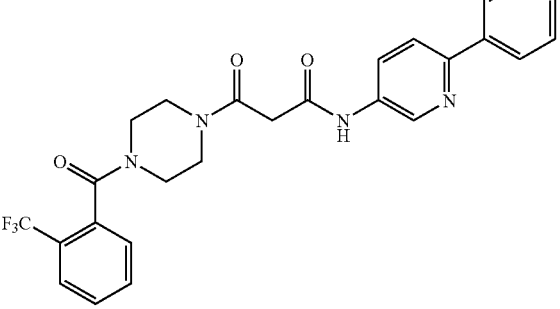

HOBt (48 mg, 0.35 mmol) and DMAP (54 mg, 0.44 mmol) were added to a stirred solution of 3-oxo-3-[4-(2-trifluoromethyl-benzoyl)-piperazin-1-yl]-propionic acid (100 mg, 0.29 mmol) in DMF (2 mL). The reaction mixture was cooled to 10° C. and EDCI.HCl (67 mg, 0.35 mmol) followed by 6-phenyl-pyridin-3-ylamine (50 mg, 0.29 mmol) were added. The reaction mixture was stirred at the room temperature overnight then diluted with water and the product extracted with ethyl acetate. The organic layer was washed with brine solution, dried over $Na_2SO_4$ and concentrated. The residue was purified by column chromatography using silica gel 60-120 mesh (60% ethyl acetate in hexane) to afford 36 mg (25%) of 3-oxo-N-(6-phenyl-pyridin-3-yl)-3-[4-(2-trifluoromethyl-benzoyl)-piperazin-1-yl]-propionamide. LCMS: 497.16 (M+1)$^+$, 97.8%, $^1$H NMR: (CDCl$_3$): δ 10.0 (d, 1H), 8.7 (d, phenyl-pyridine. LCMS purity: 201 (M+1)$^+$, 98.2%, $^1$H NMR (DMSO-d$_6$): δ 9.5 (s, 1H), 8.55 (dd, 1H), 8.1 (m, 2H), 7.9 (d, 1H), 7.55 (m, 3H).

Synthesis of N-(4-Phenyl-thiazol-2-yl)-malonamic acid ethyl ester

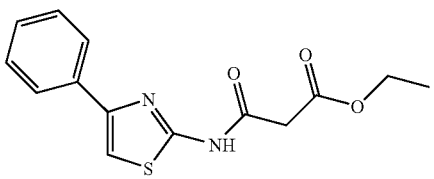

Mono ethyl malonyl chloride (375 mg, 2.49 mmol) was added dropwise to a stirred solution of 4-phenyl-thiazol-2-ylamine (400 mg, 2.26 mmol) and DIEA (733 mg, 5.67 mmol) in CHCl$_3$ (4 mL) at 0° C. and the resulting mixture was stirred for 20 minutes at room temperature. The mixture was diluted with water (5 mL) and extracted with chloroform. The organic layer was washed with saturated sodium bicarbonate solution, brine, dried over Na$_2$SO$_4$, and concentrated to afford 302 mg (46%) of N-(4-phenyl-thiazol-2-yl)-malonamic acid ethyl ester.

Synthesis of N-(4-Phenyl-thiazol-2-yl)-malonamic acid

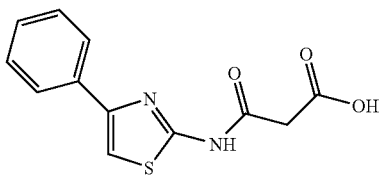

LiOH.H$_2$O (85 mg, 2.0 mmol) was added to a solution of N-(4-phenyl-thiazol-2-yl)-malonamic acid ethyl ester (292 mg, 1.0 mmol) in methanol (1.0 mL), THF (1.5 mL) and H$_2$O (1 mL). The resulting mixture was stirred for 1 hour at room temperature then concentrated. The residue was diluted with water, acidified with concentrated HCl and extracted with ethyl acetate. The organics were washed with brine, dried over Na$_2$SO$_4$ and concentrated to afford 230 mg (87%) of N-(4-Phenyl-thiazol-2-yl)-malonamic acid.

Example 26

Synthesis of 3-Oxo-N-(4-phenyl-thiazol-2-yl)-3-[4-(2-trifluoromethyl-benzoyl)-piperazin-1-yl]-propionamide

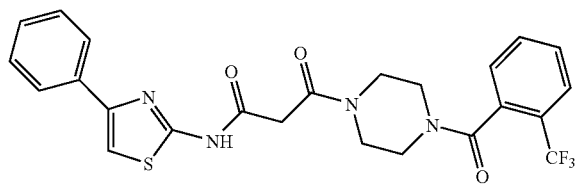

HOBt (38 mg, 0.29 mmol) and DIEA (111 mg, 0.85 mmol) were added to a stirred solution of N-(4-phenyl-thiazol-2-yl)-malonamic acid (75 mg, 0.29 mmol) in DMF (1.5 mL). The reaction mixture was cooled to 10° C. and EDCI.HCl (66 mg, 0.34 mmol) followed by piperazin-1-yl-(2-trifluoromethyl-phenyl)-methanone hydrochloride (92 mg, 0.3 mmol) were added. The reaction mixture was stirred at room temperature overnight then diluted with water and the product extracted with ethyl acetate. The organic layer was washed with sodium bicarbonate and brine solution, dried over Na$_2$SO$_4$ and concentrated to afford 21 mg (13%) of 3-Oxo-N-(4-phenyl-thiazol-2-yl)-3-[4-(2-trifluoromethyl-benzoyl)-piperazin-1-yl]-propionamide. LCMS: 503.13 (M+1)$^+$, 97.4%, $^1$H NMR: (CDCl$_3$): δ 7.85 (d, 2H), 7.74 (d, 1H), 7.6 (m, 2H), 7.4 (td, 2H), 7.33 (m, 2H), 7.15 (d, 1H), 4.02 (m, 2H), 3.7 (m, 4H), 3.52 (m, 2H), 3.24 (m, 2H).

Synthesis of 3-Oxo-3-[4-(3,4,5-trifluoro-benzoyl)-piperazin-1-yl]-propionic acid ethyl ester

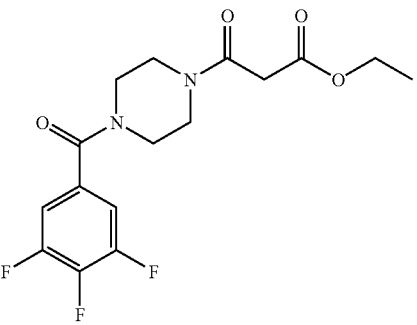

Mono-ethyl malonyl chloride (235 mg, 1.56 mmol) was added drop wise to a stirred solution of piperazin-1-yl-(3,4,5-trifluoro-phenyl)-methanone (380 mg, 1.56 mmol) in dichloromethane (10 mL) at 0° C. and the resulting mixture was refluxed for 30 minutes. The mixture was then diluted with water and the product was extracted with dichloromethane. The organic layer was washed with saturated sodium bicarbonate solution, followed by brine, dried over Na$_2$SO$_4$ and concentrated to afford 450 mg (81%) of 3-oxo-3-[4-(3,4,5-trifluoro-benzoyl)-piperazin-1-yl]-propionic acid ethyl ester. LCMS: 359.12 (M+1)$^+$, 98.9%, $^1$H NMR: (CDCl$_3$): δ 7.0 (t, 2H), 4.2 (q, 2H), 3.5 (m, 10H), 1.4 (t, 3H).

Synthesis of 3-Oxo-3-[4-(3,4,5-trifluoro-benzoyl)-piperazin-1-yl]-propionic acid

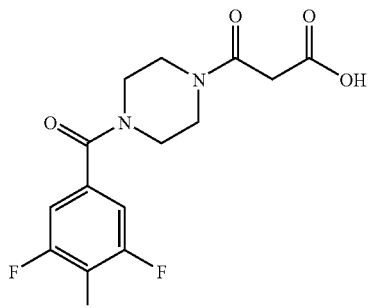

LiOH.H$_2$O (93 mg, 2.2 mmol) was added to a solution of 3-oxo-3-[4-(3,4,5-trifluoro-benzoyl)-piperazin-1-yl]-propionic acid ethyl ester (400 mg, 1.1 mmol) in a mixture of methanol (2 mL), THF (5 mL) and H$_2$O (2 mL). The resulting mixture was stirred for 2 hours at room temperature. The mixture was then concentrated and the residue was diluted with water, washed with diethyl ether and acidified with concentrated HCl. The residue was extracted with ethyl acetate and concentrated to afford 230 mg (62%) of 3-oxo-3-[4-(3,4, 1H), 8.2 (dd, 1H), 8.0 (d, 2H), 7.7 (m, 4H), 7.4 (m, 4H), 4.03 (m, 2H), 3.7 (m, 3H), 3.54 (m, 3H), 3.23 (m. 2H).

5-trifluoro-benzoyl)-piperazin-1-yl]-propionic acid. LCMS: 331.09 (M+1)+, 90.2%, ¹H NMR: (CDCl₃): δ 7.0 (t, 2H), 3.7 (s, 4H), 3.5 (m, 6H).

Example 27

Synthesis of 3-Oxo-N-(6-phenyl-pyridin-3-yl)-3-[4-(3,4,5-trifluoro-benzoyl)-piperazin-1-yl]-propionamide

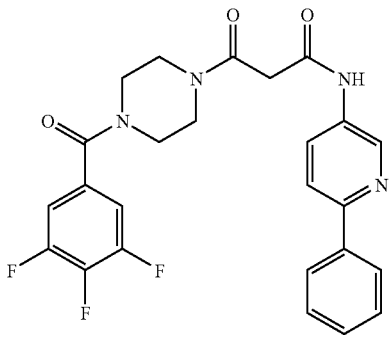

HOBt (40 mg, 0.3 mmol) and DMAP (46 mg, 0.37 mmol) were added to a stirred solution of 3-oxo-3-[4-(3,4,5-trifluoro-benzoyl)-piperazin-1-yl]-propionic acid (83 mg, 0.25 mmol) in DMF (2 mL). The reaction mixture was cooled to 10° C. and EDCI.HCl (58 mg, 0.3 mmol) followed by 6-phenyl-pyridin-3-ylamine (51 mg, 0.3 mmol) were added. The reaction mixture was stirred at room temperature overnight, diluted with water and the product was extracted with ethyl acetate. The organic layer was washed with brine solution, dried over Na₂SO₄ and concentrated to afford 44 mg (36%) of 3-oxo-N-(6-phenyl-pyridin-3-yl)-3-[4-(3,4,5-trifluoro-benzoyl)-piperazin-1-yl]-propionamide. LCMS: 483.16 (M+1)+, 97.0%, ¹H NMR: (DMSO-d₆): δ 10.5 (s, 1H), 8.8 (d, 1H), 8.2-8.1 (m, 1H), 8.1 (d, 2H), 8.0 (d, 1H), 7.6-7.4 (m, 5H), 3.4-3.2 (m. 10H).

Example 28

Synthesis of N-(4-[1,2, and 4]Oxadiazol-3-yl-phenyl)-3-oxo-3-[4-(3,4,5-trifluoro-benzoyl)-piperazin-1-yl]-propionamide

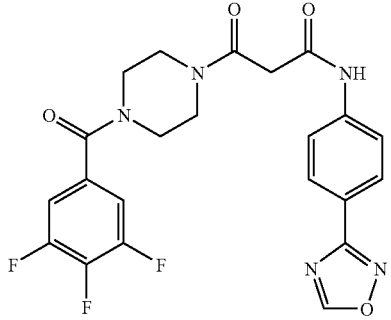

HOBt (49 mg, 0.36 mmol) and DMAP (55 mg, 0.45 mmol) were added to a stirred solution of 3-oxo-3-[4-(3,4,5-trifluoro-benzoyl)-piperazin-1-yl]-propionic acid (100 mg, 0.3 mmol) in DMF (2 mL). The reaction mixture was cooled to 10° C. and EDCI.HCl (69 mg, 0.36 mmol) followed by 4-[1, 2,4]-oxadiazol-3-yl-phenylamine (53 mg, 0.33 mmol) were added. The reaction mixture was stirred at room temperature overnight then diluted with water and the product extracted with ethyl acetate. The organic layer was washed with brine solution, dried over Na₂SO₄ and concentrated. The residue was purified by column chromatography using silica 60-120 mesh (30% ethyl acetate in hexane) to afford 15 mg (11%) of N-(4-[1,2, and 4]oxadiazol-3-yl-phenyl)-3-oxo-3-[4-(3,4,5-trifluoro-benzoyl)-piperazin-1-yl]-propionamide. LCMS: 474.13 (M+1)+, 98.2%, ¹H NMR: (DMSO-d₆): δ 10.5 (s, 1H), 9.7 (s, 1H), 8.0 (d, 2H), 7.8 (d, 2H), 7.5 (t, 2H), 3.6 (m, 10H).

Synthesis of N-Phenyl-benzene-1,4-diamine

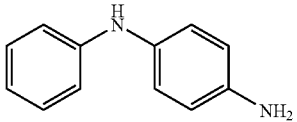

Ammonium chloride (48 mg, 9 mmol) in water (1 mL) was added to a stirred solution of (4-nitro-phenyl)-phenyl-amine (200 mg, 0.9 mmol) in THF (4 mL). Zinc powder (48 mg, 7.4 mmol) was then added portion wise and the resulting mixture was stirred at room temperature for 2 hours then filtered over celite. The filtrate was extracted with ethyl acetate and the ethyl acetate was washed with brine solution, dried over Na₂SO₄ and concentrated to 160 mg (96%) of N-phenyl-benzene-1,4-diamine. LCMS: 185.1 (M+1)+, 93.9%, ¹H NMR: (DMSO-d₆): 67.2 (t, 2H), 7.0 (d, 2H), 6.8 (m, 2H), 6.7 (d, 2H).

Example 29

Synthesis of 3-Oxo-N-(4-phenylamino-phenyl)-3-[4-(2-trifluoromethyl-benzoyl)-piperazin-1-yl]-propionamide

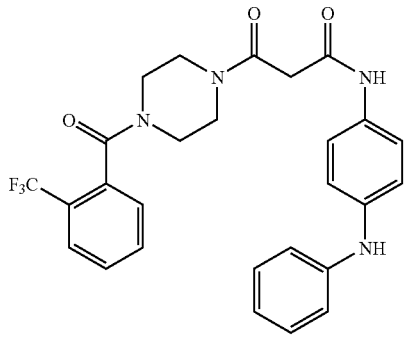

HOBt (70 mg, 0.5 mmol) and DIEA (11 mg, 0.9 mmol) were added to a stirred solution of 3-oxo-3-[4-(2-trifluoromethyl-benzoyl)-piperazin-1-yl]-propionic acid (50 mg, 0.3 mmol) in DMF (3 mL). The reaction mixture was cooled to 10° C. and EDCI.HCl (80 mg, 0.5 mmol) followed by N-phenyl-benzene-1,4-diamine (100 mg, 0.3 mmol) were added. The reaction mixture was stirred at room temperature overnight then diluted with water and the product extracted with ethyl acetate. The organic layer was washed with brine solution, dried over Na₂SO₄ and concentrated. The residue was purified by column chromatography using basic alumina (10% methanol in chloroform) to afford 15 mg (10%) of 3-oxo-N-(4-phenylamino-phenyl)-3-[4-(2-trifluoromethyl-benzoyl)-piperazin-1-yl]-propionamide. LCMS: 511.19 (M+1)+, 96.55%, ¹H NMR: (CDCl₃): δ 7.7 (m, 1H), 7.6 (m, 2H), 7.4 (m, 4H), 7.1 (m, 1H), 7.0 (m, 3H), 6.8 (m, 1H), 4.0 (m, 2H), 3.8 (m, 2H), 3.4 (m, 3H), 3.2 (m, 2H).

Synthesis of N-(6-Phenyl-pyridin-3-yl)-malonamic acid ethyl ester

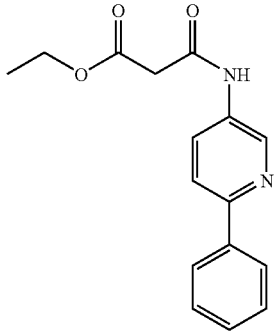

Mono ethyl malonyl chloride (132 mg, 0.88 mmol) was added drop wise to a stirred solution of 6-phenyl-pyridin-3-ylamine (100 mg, 0.58 mmol) in dichloromethane (1 mL) at 0° C. and the resulting mixture was stirred for 1 hour. The mixture was then diluted with water and the product extracted with dichloromethane. The organic layer was washed with saturated sodium bicarbonate solution, followed by brine, dried over $Na_2SO_4$ and concentrated to afford 150 mg (90%) of N-(6-phenyl-pyridin-3-yl)-malonamic acid ethyl ester. $^1H$ NMR: ($CDCl_3$): δ 9.5 (s, 1H), 9.3 (s, 1H), 8.7 (d, 1H), 8.3 (dd, 1H), 8.0-7.9 (m, 2H), 7.7 (d, 1H), 7.54-7.38 (m, 3H), 4.3 (q, 2H), 3.5 (s, 2H), 1.4 (t, 3H).

Synthesis of N-(6-Phenyl-pyridin-3-yl)-malonamic acid

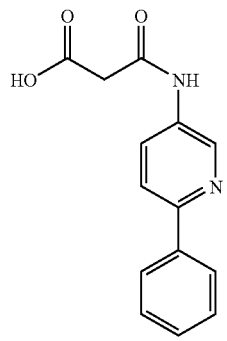

$LiOH \cdot H_2O$ (11 mg, 0.26 mmol) was added to a solution of N-(6-phenyl-pyridin-3-yl)-malonamic acid ethyl ester (50 mg, 0.17 mmol) in a mixture of methanol (0.5 mL), THF (1 mL) and $H_2O$ (0.3 mL). The reaction mixture was stirred for 1 hour at room temperature then concentrated. The residue was diluted with water, acidified with concentrated HCl and the resulting precipitate was filtered to afford 25 mg (44%) of N-(6-phenyl-pyridin-3-yl)-malonamic acid. LCMS: 257.09 $(M+1)^+$, 96%, $^1H$ NMR: (DMSO-$d_6$): δ 10.5 (s, 1H), 8.8 (d, 1H), 8.2 (dd, 1H), 8.0 (d, 2H), 7.9 (d, 1H), 7.5-7.3 (m, 3H), 3.4 (s, 2H).

Example 30

Synthesis of 3-[4-(2-Bromo-benzoyl)-piperazin-1-yl]-3-oxo-N-(6-phenyl-pyridin-3-yl)-propionamide

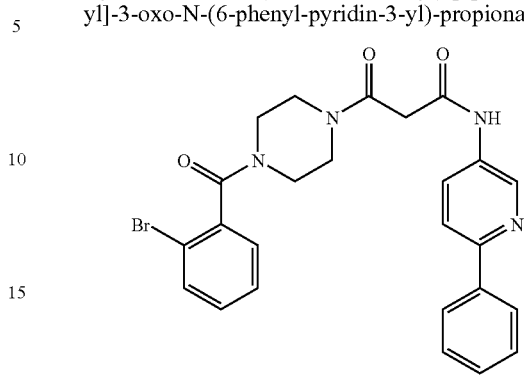

HOBt (41 mg, 0.3 mmol) and DIEA (98 mg, 0.76 mmol) were added to a stirred solution of N-(6-phenyl-pyridin-3-yl)-malonamic acid (65 mg, 0.25 mmol) in DMF (2 mL). The reaction mixture was cooled to 10° C. and EDCI.HCl (58 mg, 0.3 mmol) followed by (2-bromo-phenyl)-piperazin-1-yl-methanone hydrochloride (93 mg, 0.3 mmol) were added. The reaction mixture was stirred at room temperature overnight then diluted with water and the product extracted with ethyl acetate. The organic layer was washed with brine solution, dried over $Na_2SO_4$ and concentrated to afford 58.5 mg (46%) of 3-[4-(2-bromo-benzoyl)-piperazin-1-yl]-3-oxo-N-(6-phenyl-pyridin-3-yl)-propionamide. LCMS: 507.1 $(M+1)^+$ 98.54%, $^1H$ NMR: (DMSO-$d_6$): δ 10.5 (d, 1H), 8.8 (dd, 1H), 8.2-7.86 (m, 4H), 7.5 (d, 1H), 7.34 (m, 6H), 3.8-3.4 (m, 8H), 3.2-3.1 (m. 2H).

Synthesis of Malonic acid tert-butyl ester ethyl ester

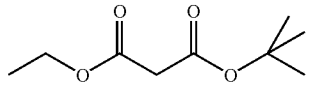

tert-butanol (2.8 mL, 37.8 mmol) was added to a stirred solution of malonic acid monoethyl ester (5 g, 37.8 mmol) in acetonitrile (45 mL). DCC (8.58 g, 41.6 mmol) dissolved in acetonitrile (5 mL) was added dropwise with stirring over a period of 2 hours. The reaction mixture was filtered and the filtrate was concentrated to afford 4.72 g (66%) of malonic acid tert-butyl ester ethyl ester. LCMS: 189.11 $(M+1)^+$ 93.4%, $^1H$ NMR: ($CDCl_3$): δ 4.2 (q, 2H), 3.3 (s, 2H), 1.4 (s, 9H), 1.3 (t, 3H).

Synthesis of Lithium tert-butoxycarbonyl-acetate

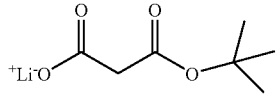

$LiOH \cdot H_2O$ (1.57 g, 37 mmol) was added to a solution of malonic acid tert-butyl ester ethyl ester (4.7 g, 25 mmol) in a mixture of methanol (23 mL), THF (47 mL) and $H_2O$ (14 mL). The reaction mixture was stirred for 1 hour at room temperature then concentrated to afford 4.0 g (96%) of lithium tert-butoxycarbonyl-acetate. $^1H$ NMR: (DMSO-$d_6$): δ 2.8 (s, 2H), 1.4 (s, 9H).

Synthesis of 3-[4-(2-Bromo-benzoyl)-piperazin-1-yl]-3-oxo-propionic acid tert-butyl ester

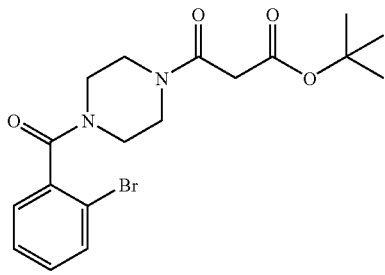

HOBt (585 mg, 4.3 mmol) and DIEA (933 mg, 7.2 mmol) were added to a stirred solution of lithium tert-butoxycarbonyl-acetate (600 mg, 3.6 mmol) in DMF (6 mL). The reaction mixture was cooled to 10° C. and EDCI.HCl (830 mg, 4.3 mmol) followed by (2-bromo-phenyl)-piperazin-1-yl-methanone hydrochloride (1.3 g, 4.3 mmol) were added. The reaction mixture was stirred at room temperature overnight then diluted with water and the product extracted with ethyl acetate. The organic layer was washed with brine solution, dried over $Na_2SO_4$ and concentrated. The residue was purified by column chromatography using neutral alumina (3% methanol in chloroform) to afford 530 mg (31%) of 3-[4-(2-bromo-benzoyl)-piperazin-1-yl]-3-oxo-propionic acid tert-butyl ester. LCMS: 412.08 $(M^+)^+$, 52.6%, $^1$H NMR: (DMSO-$d_6$): δ 7.7 (d, 1H), 7.5 (m, 1H), 7.4 (m, 2H), 3.7-3.4 (m, 8H), 3.2-3.1 (m, 2H), 1.4 (s, 9H).

Synthesis of 3-[4-(2-Bromo-benzoyl)-piperazin-1-yl]-3-oxo-propionic acid

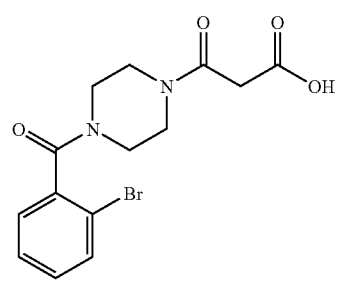

A solution of 3-[4-(2-bromo-benzoyl)-piperazin-1-yl]-3-oxo-propionic acid tert-butyl ester (400 mg, 0.97 mmol) in dioxane.HCl (4 mL) was stirred at 0° C. for 30 minutes. The reaction mixture was concentrated to afford 300 mg of 3-[4-(2-bromo-benzoyl)-piperazin-1-yl]-3-oxo-propionic acid. LCMS: 356.02 $(M+1)^+$, 96.9%, $H^1$NMR: (DMSO-$d_6$): δ 12.6 (s, 1H), 7.7 (d, 1H), 7.54-7.32 (m, 3H), 3.7-3.4 (m, 8H), 3.2-3.06 (m, 2H).

Example 31

Synthesis of 3-[4-(2-Bromo-benzoyl)-piperazin-1-yl]-N-(4-[1,2, and 4]oxadiazol-3-yl-phenyl)-3-oxo-propionamide

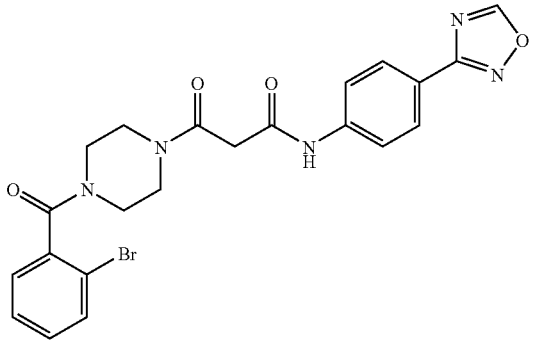

HOBt (36 mg, 0.27 mmol) and DMAP (41 mg, 0.3 mmol) were added to a stirred solution of 3-[4-(2-bromo-benzoyl)-piperazin-1-yl]-3-oxo-propionic acid (80 mg, 0.2 mmol) in DMF (1 mL). The reaction mixture was cooled to 10° C. and EDCI.HCl (52 mg, 0.27 mmol) followed by 4-[1,2,4]oxadiazol-3-yl-phenylamine (43 mg, 0.27 mmol) was added. The reaction mixture was stirred at room temperature overnight then diluted with water and the product extracted with ethyl acetate. The organic layer was washed with brine solution, dried over $Na_2SO_4$ and concentrated to afford 41.7 mg (37%) of 3-[4-(2-bromo-benzoyl)-piperazin-1-yl]-N-(4-[1,2, and 4]oxadiazol-3-yl-phenyl)-3-oxo-propionamide. LCMS: 499.07 $(M+1)^+$, 97.3%, $^1$H NMR: (DMSO-$d_6$): δ 10.5 (s, 1H), 8.8 (d, 1H), 8.2 (d, 1H), 8.1 (d, 2H), 8.0 (d, 1H), 7.5-7.3 (m, 3H), 3.8-3.7 (m, 1H), 3.7-3.5 (m, 7H), 3.2-3.1 (m, 2H).

Synthesis of 4-(4-Nitro-phenyl)-morpholine

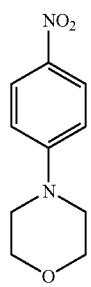

A mixture of 1-fluoro-4-nitro-benzene (500 mg, 3.54 mmol), morpholine (620 mg, 7.08 mmol) and $K_2CO_3$ (733 mg, 5.3 mmol) in DMSO (5 mL) was irradiated in a microwave (160 W) for 30 seconds (3×10 seconds). The reaction mixture was cooled to room temperature and poured onto ice. The resulting precipitated was filtered to afford 490 mg (66%) of 4-(4-nitro-phenyl)-morpholine. $^1$H NMR: (DMSO-$d_6$): δ 8.1 (m, 2H), 7.1 (m, 2H), 3.42 (t, 4H), 3.4 (t, 4H).

55

Synthesis of 4-Morpholin-4-yl-phenylamine

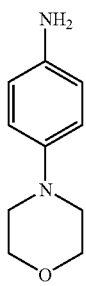

Ammonium chloride (1.2 g, 23.0 mmol) in water (4.5 mL) then MeOH (9 mL) were added to a stirred solution of 4-(4-nitro-phenyl)-morpholine (480 mg, 2.3 mmol) in THF (9 mL). Zinc powder (1.2 g, 18.4 mmol) was then added portion wise and the resulting mixture was stirred at room temperature for 15 minutes. The reaction mixture was filtered over celite and the filtrate was extracted with ethyl acetate. The organic layer was washed with brine, dried over $Na_2SO_4$ and concentrated to afford 316 mg (77%) of 4-morpholin-4-yl-phenylamine. $^1$H NMR: (DMSO-$d_6$): δ 6.7 (m, 2H), 6.5 (m, 2H), 4.6 (s, 2H), 3.7 (t, 4H), 2.8 (t, 4H).

Example 32

Synthesis of 3-[4-(2-Bromo-benzoyl)-piperazin-1-yl]-N-(4-morpholin-4-yl-phenyl)-3-oxo-propionamide

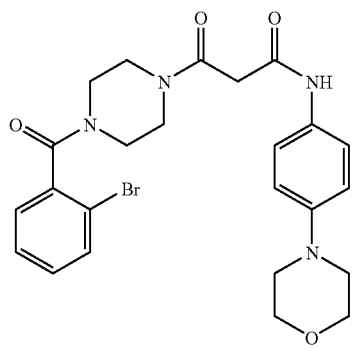

HOBt (31 mg, 0.23 mmol) and DMAP (42 mg, 0.34 mmol) were added to a stirred solution of 3-[4-(2-bromo-benzoyl)-piperazin-1-yl]-3-oxo-propionic acid (75 mg, 0.2 mmol) in DMF (1 mL). The reaction mixture was cooled to 0° C. and EDCI.HCl (48 mg, 0.25 mmol) followed by 4-morpholin-4-yl-phenylamine (41 mg, 0.23 mmol) were added. The reaction mixture was stirred at room temperature overnight then diluted with water. The resulting precipitate was filtered and washed with hexane to afford 45 mg (41%) of 3-[4-(2-bromo-benzoyl)-piperazin-1-yl]-N-(4-morpholin-4-yl-phenyl)-3-oxo-propionamide. LCMS: 516.12 (M+1)$^+$, 97.57%, $^1$H NMR: (DMSO-$d_6$): δ 7.7 (m, 1H), 7.5-7.32 (m, 5H), 6.9-6.8 (m, 2H), 3.8-3.7 (bs, 5H), 3.6-3.4 (m, 7H), 3.2-3.08 (m, 2), 3.04-2.98 (m, 3H).

56

Synthesis of 1H-Pyridin-2-one

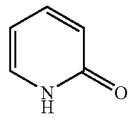

10% Pd/C (700 mg) was added to a stirred of 2-benzyloxy-pyridine (3.5 g, 18.9 mmol) in MeOH the reaction mixture was maintained under an atmosphere of hydrogen 30 minutes. The mixture was then filtered over celite and the filtrate was concentrated to afford 1.73 g (95%) of 1H-Pyridin-2-one. $^1$H NMR: (DMSO-$d_6$): δ 11.8 (bs, 1H), 7.4 (m, 2H), 6.3 (m, 1H), 6.2 (m, 1H).

Synthesis of 1-(4-Nitro-phenyl)-1H-pyridin-2-one

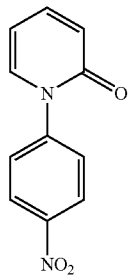

A solution of 1H-pyridin-2-one (950 mg, 10 mmol), 1-bromo-4-nitro-benzene (2.4 g, 12 mmol) and CuI (400 mg, 2 mmol) in dioxane (15 mL) was stirred for 15 minutes. N,N'-dimethyl ethylenediamine (363 mg, 4 mmol) was then added, followed by the addition of $K_3PO_4$ (4.25 g, 20 mmol). The resulting mixture was heated to reflux at 110° C. for 2 hours under an atmosphere of nitrogen. The reaction mixture was then cooled to room temperature and poured onto ice. The resulting precipitate was filtered and purified by column chromatography using silica gel 60-120 mesh (50-100% ethyl acetate in hexane) to afford 1.86 g (89%) of 1-(4-nitro-phenyl)-1H-pyridin-2-one. $^1$H NMR: (DMSO-$d_6$): δ 8.46 (d, 2H), 7.8 (m, 3H), 7.6 (t, 1H), 6.6 (d, 1H).

Synthesis of 1-(4-Amino-phenyl)-1H-pyridin-2-one

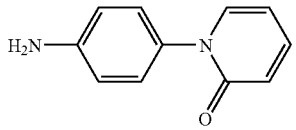

Ammonium chloride (4.45 g, 83.26 mmol) in water (10 mL) and methanol (20 mL) was added to a stirred solution of 1-(4-nitro-phenyl)-1H-pyridin-2-one (1.8 g, 8.3 mmol) in THF (20 mL). Zinc powder (4.3 g, 66.6 mmol) was then added portion wise and the resulting mixture was stirred at room temperature for 30 minutes. The mixture was filtered over celite and the filtrate was concentrated and extracted with ethyl acetate. The organic layer was washed with brine solution, dried over $Na_2SO_4$ and concentrated to afford 1.23 g (79%) of 1-(4-amino-phenyl)-1H-pyridin-2-one. $^1$H NMR: (DMSO-$d_6$): δ 7.6-7.4 (m, 2H), 7.0 (d, 2H), 6.7 (d, 2H), 6.45 (d, 1H), 6.3 (t, 1H), 5.4 (s, 2H).

Synthesis of N-[4-(2-Oxo-2H-pyridin-1-yl)-phenyl]-malonamic acid ethyl ester

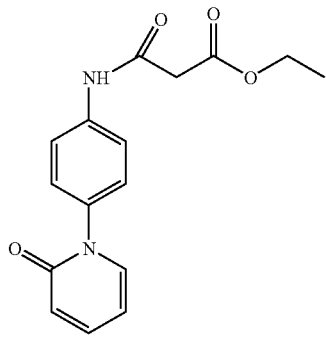

Mono ethyl malonyl chloride (182 mg, 1.2 mmol) was added drop wise to a stirred solution of 1-(4-amino-phenyl)-1H-pyridin-2-one (200 mg, 1.1 mmol) in CHCl$_3$ (10 mL) at 0° C. was and the resulting mixture was stirred for 1 hour. The mixture was then diluted with water and the product extracted with CHCl$_3$. The organic layer was washed with saturated sodium bicarbonate solution, followed by brine, dried over Na$_2$SO$_4$ and concentrated to afford 226 mg (68%) of N-[4-(2-oxo-2H-pyridin-1-yl)-phenyl]-malonamic acid ethyl ester. $^1$H NMR: (DMSO-d$_6$): δ 10.4 (s, 1H), 7.8-7.6 (m, 3H), 7.5 (t, 1H), 7.4 (d, 2H), 6.5 (d, 1H), 6.3 (t, 1H), 4.2 (q, 2H), 1.3 (t, 3H).

Synthesis of N-[4-(2-Oxo-2H-pyridin-1-yl)-phenyl]-malonamic acid

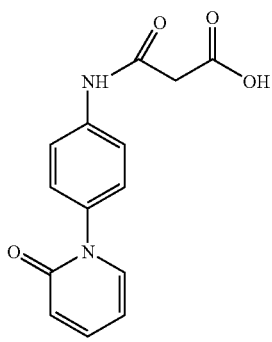

LiOH.H$_2$O (56 mg, 1.3 mmol) was added to a solution of N-[4-(2-oxo-2H-pyridin-1-yl)-phenyl]-malonamic acid ethyl ester (200 mg, 0.6 mmol) in methanol (0.5 mL), THF (1 mL) and H$_2$O (0.5 mL) and the resulting mixture was stirred for 1 hour at room temperature then concentrated. The residue was diluted with water and acidified with concentrated HCl. The resulting precipitate was isolated by filtration to afford 156 mg (86%) of N-[4-(2-oxo-2H-pyridin-1-yl)-phenyl]-malonamic acid. $^1$H NMR: (DMSO-d$_6$): δ 12.8 (s, 1H), 10.3 (s, 1H), 7.78-7.6 (m, 3H), 7.5 (t, 1H), 7.4-7.3 (m, 2H), 6.5 (d, 1H), 6.38 (t, 1H), 3.4 (d, 2H).

Example 33

Synthesis of 3-[4-(2-Bromo-benzoyl)-piperazin-1-yl]-3-oxo-N-[4-(2-oxo-2H-pyridin-1-yl)-phenyl]-propionamide

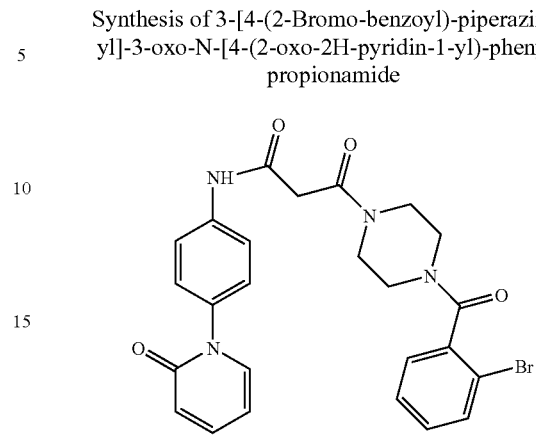

HOBt (75 mg, 0.55 mmol) and DIPEA (213 mg, 1.65 mmol) were added to a stirred solution of N-[4-(2-oxo-2H-pyridin-1-yl)-phenyl]-malonamic acid (150 mg, 0.55 mmol) in DMF (2.0 mL). The reaction mixture was cooled to 0° C. and EDCI.HCl (126 mg, 0.66 mmol) followed by (2-bromo-phenyl)-piperazin-1-yl-methanone hydrochloride (185 mg, 0.6 mmol) were added. The reaction mixture was stirred at room temperature overnight then diluted with water. The resulting precipitate was recrystallized from ethyl acetate: hexane (1:1) to afford 180 mg (21%) of 3-[4-(2-bromo-benzoyl)-piperazin-1-yl]-3-oxo-N-[4-(2-oxo-2H-pyridin-1-yl)-phenyl]-propionamide. LCMS: 524.09 (M+1)$^+$,89.7%, $^1$H NMR: (DMSO-d6): δ 7.7-7.2 (m, 8H), 6.5 (m, 1H), 6.3 (m, 1H), 3.8-3.6 (m, 5H), 3.6-3.34 (m, 3H), 3.2 (m, 2H).

Synthesis of 4-(3-Fluoro-benzoyl)-piperazine-1-carboxylic acid tert-butyl ester

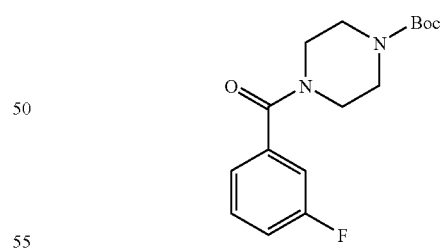

HOBt (290 mg, 2.14 mmol), DIEA (461 mg, 3.5 mmol), EDCI.HCl (410 mg, 2.14 mmol) followed by piperazine-1-carboxylic acid tert-butyl ester (398 mg, 2.14 mmol) were added to a stirred solution of 3-fluorobenzoic acid (250 mg, 1.78 mmol) in DMF (3 mL). The reaction mixture was stirred overnight and then diluted with cold water. The product was extracted with ethyl acetate and the organic layer was washed with brine solution, dried over Na$_2$SO$_4$, and concentrated under reduced pressure to afford 590 mg (92%) of 4-(3-fluoro-benzoyl)-piperazine-1-carboxylic acid tert-butyl ester.

Synthesis of (3-Fluoro-phenyl)-piperazin-1-yl-methanone hydrochloride

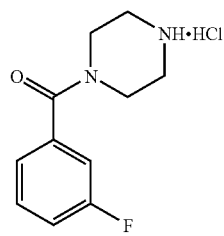

A cold solution of 4-(3-fluoro-benzoyl)-piperazine-1-carboxylic acid tert-butyl ester (400 mg, 1.29 mmol) in 1,4-dioxane.HCl (1 mL) was stirred at 0° C. for 1 hour. The reaction mixture was then concentrated under reduced pressure and the resulting crude residue was washed with ether and dried to afford 280 mg (89%) of (3-fluoro-phenyl)-piperazin-1-yl-methanone.hydrochloride.

Synthesis of 4-(3-Cyano-benzoyl)-piperazine-1-carboxylic acid tert-butyl ester

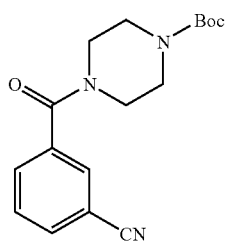

DIEA (527 mg, 4.07 mmol), HOBt (322 mg, 2.45 mmol), EDCI.HCl (302 m, 1.5 mmol) and piperazine-1-carboxylic acid tert-butyl ester (456 mg, 2.45 mmol) were added to a stirred solution of 3-cyano-benzoicacid (300 mg, 2.03 mmol) in DMF (3 mL) and the resulting mixture was stirred at ambient temperature overnight. The reaction mixture was then diluted with water and the product was extracted with ethyl acetate. The ethyl acetate layer was washed with brine solution, dried over $Na_2SO_4$, and concentrated under reduced pressure to afford 590 mg (92%) of 4-(3-cyano-benzoyl)-piperazine-1-carboxylic acid tert-butyl ester.

Synthesis of (3-Cyano-phenyl)-piperazin-1-yl-methanone.hydrochloride

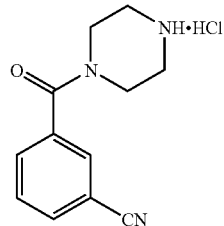

A solution of 4-(3-cyano-benzoyl)-piperazine-1-carboxylic acid tert-butyl ester (590 mg, 1.87 mmol) in 1,4-dioxane-.HCl (3 mL) was stirred at 0° C. for 1 hour. The reaction mixture was then concentrated under reduced pressure and the resulting residue was washed with ether and dried to afford 350 mg (75%) of (3-cyano-phenyl)-piperazin-1-yl-methanone.hydrochloride.

Synthesis of Cyclopropane-1,1-dicarboxylic acid methyl ester

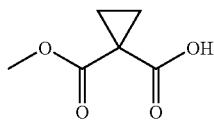

KOH (42 mg, 0.75 mmol) was added to a solution cyclopropane-1,1-dicarboxylic acid dimethyl ester (100 mg, 0.63 mmol) in methanol. The resulting mixture was stirred for 4 hours at ambient temperature then concentrated. The residue was diluted with water, acidified with conc. HCl and the product was extracted with dichloromethane. The organic layer was dried over sodium sulfate and concentrated under reduced pressure to afford 65 mg (71%) of cyclopropane-1,1-dicarboxylic acid methyl ester.

Synthesis of 1-(Biphenyl-4-ylcarbamoyl)-cyclopropanecarboxylic acid methyl ester

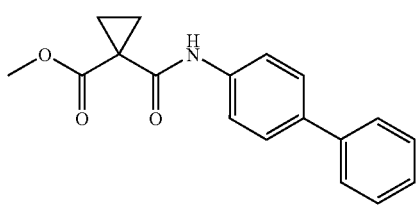

HOBt (70 mg, 0.54 mmol), DMAP (110 mg, 0.9 mmol), EDCI.HCl (104 mg, 0.54 mmol) followed by biphenyl-4-ylamine (92 mg, 0.54 mmol) were added to a stirred solution of cyclopropane-1,1-dicarboxylic acid methyl ester (65 mg, 0.45 mmol) in DMF (2 mL) and the resulting mixture was stirred at ambient temperature overnight. The reaction mixture was then diluted with water. The resulting precipitate was isolated by filtration and dried to afford 100 mg (75%) of 1-(biphenyl-4-ylcarbamoyl)-cyclopropanecarboxylic acid methyl ester.

Synthesis of 1-(Biphenyl-4-ylcarbamoyl)-cyclopropanecarboxylic acid

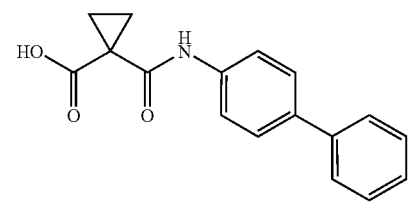

$LiOH.H_2O$ (21 mg, 0.5 mmol) was added to a solution of 1-(biphenyl-4-ylcarbamoyl)-cyclopropanecarboxylic acid methyl ester (100 mg, 0.33 mmol) in methanol (0.5 mL), THF (1 mL) and $H_2O$ (0.3 mL) and the resulting mixture was stirred for 2 hours at ambient temperature. The reaction mixture was then concentrated and the residue was diluted with water, acidified with conc. HCl. The resulting precipitate was isolated by filtration and dried to afford 55 mg (58%) of 1-(biphenyl-4-ylcarbamoyl)-cyclopropanecarboxylic acid

Example 34

Synthesis of 1-[4-(2-Bromo-benzoyl)-piperazine-1-carbonyl]-cyclopropanecarboxylic acid biphenyl-4-ylamide

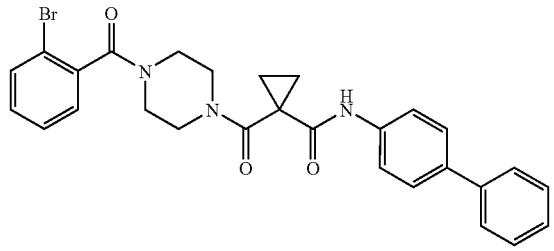

HOBt (32 mg, 0.23 mmol), DIPEA (91 mg, 0.7 mmol) and EDCI.HCl (45 mg, 0.23 mmol) were added to a stirred solution of N-biphenyl-4-yl-malonamic acid (55 mg, 0.19 mmol) in DMF (2.0 mL). 2-Bromo-phenyl)-piperazin-1-yl-methanone hydrochloride (72 mg, 0.23 mmol) was then added and the resulting mixture was stirred at the ambient temperature overnight. The mixture was then diluted with water and the product was extracted with ethyl acetate. The organics were washed with brine and concentrated to afford 32 mg (31%) of 1-[4-(2-bromo-benzoyl)-piperazine-1-carbonyl]-cyclopropanecarboxylic acid biphenyl-4-ylamide. LCMS: 532.12 $(M+1)^+$, 94.09%, $^1$H NMR (DMSO-$d_6$): δ 9.8 (s, 1H), 7.8-7.2 (m, 13H), 3.8-3.4 (m, 6H), 3.2-3.1 (m, 2H), 1.5-1.2 (m, 4H).

Synthesis of 2-Fluoro-malonic acid monomethyl ester

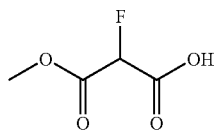

KOH (38 mg, 0.67 mmol) was added to a solution 2-fluoro-malonic acid diethyl ester (100 mg, 0.563 mmol) in methanol (0.7 mL). The reaction mixture was stirred for 4 hours at ambient temperature then concentrated. The residue was diluted with water, acidified with conc. HCl, and the product was extracted with dichloromethane. The organic layer was dried over sodium sulfate and concentrated under reduced pressure to afford 70 mg (77%) of 2-fluoro-malonic acid monomethyl ester Synthesis of N-Biphenyl-4-yl-2-fluoro-malonamic acid methyl ester

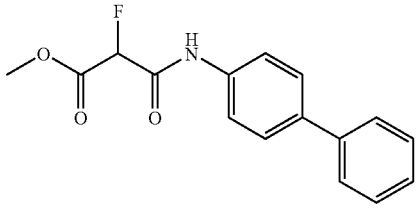

HOBt (83 mg, 0.61 mmol), DMAP (125 mg, 1.02 mmol) and EDCI.HCl (118 mg, 0.61 mmole) were added to a stirred solution of 2-fluoro-malonic acid monomethyl ester (70 mg, 0.514 mmol) in DMF (2 mL). Biphenyl-4-ylamine (100 mg, 0.61 mmol) was then added and the resulting mixture was stirred at ambient temperature overnight. The mixture was then diluted with water and the product was extracted with ethyl acetate. The ethyl acetate layer was washed with brine solution, dried over sodium sulphate and concentrated under reduced pressure to afford 114 mg (80%) of N-biphenyl-4-yl-2-fluoro-malonamic acid methyl ester Synthesis of N-Biphenyl-4-yl-2-fluoro-malonamic acid

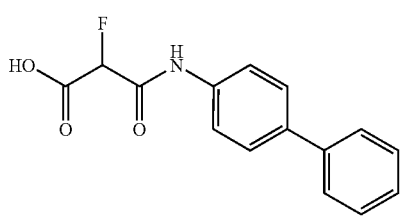

LiOH.H$_2$O (25 mg, 0.59 mmol) was added to a solution of N-biphenyl-4-yl-2-fluoro-malonamic acid methyl ester (114 mg, 0.39 mmol) in a mixture of methanol (0.5 mL), THF (1 mL) and H$_2$O (0.3 mL). The resulting mixture was stirred for 2 hours at ambient temperature then concentrated. The resulting residue was diluted with water, acidified with conc. HCl. The resulting precipitate was isolated by filtration and dried to afford 35 mg (32%) of N-biphenyl-4-yl-2-fluoro-malonamic acid

Example 35

Synthesis of N-Biphenyl-4-yl-3-[4-(2-bromo-benzoyl)-piperazin-1-yl]-2-fluoro-3-oxo-propionamide

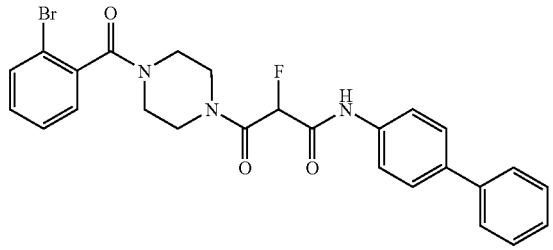

HOBt (21 mg, 0.15 mmol), DIPEA (49.6 mg, 0.384 mmol) and EDCI.HCl (29 mg, 0.15 mmol) followed by 2-bromo-phenyl)-piperazin-1-yl-methanone hydrochloride (47 mg, 0.15 mmol), were added to a stirred solution of N-biphenyl-4-yl-2-fluoro-malonamic acid (35 mg, 0.12 mmole) in DMF (1 mL) and the resulting mixture was stirred at ambient temperature overnight. The mixture was then diluted with water and the product was extracted with ethyl acetate. The organics were washed with brine and concentrated to afford 25 mg (37%) of N-biphenyl-4-yl-3-[4-(2-bromo-benzoyl)-piperazin-1-yl]-2-fluoro-3-oxo-propionamide. LCMS: 524.09 $(M+1)^+$, 94.45%, $^1$H NMR (DMSO-$d_6$): δ 8.2 (s, 1H), 7.7-7.2 (m, 13H), 6.0-5.6 (m, 1H), 4.4-3.9 (m, 3H), 3.8-3.3 (m, 5H).

Example 36

Synthesis of N-Biphenyl-4-yl-3-[4-(3-cyano-benzoyl)-piperazin-1-yl]-2-fluoro-3-oxo-propionamide

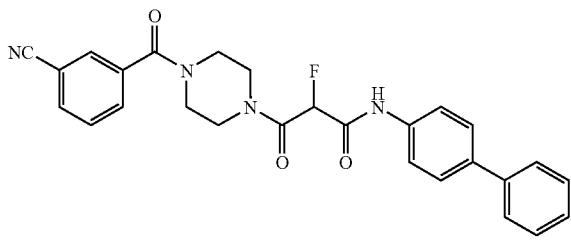

HOBt (60 mg, 0.43 mmol), DIPEA (141 mg, 1.09 mmol), EDCI.HCl (84 mg, 0.43 mmol), 3-cyano-phenyl)-piperazin-1-yl-methanone hydrochloride (110 mg, 0.439 mmol) were added to a stirred solution of N-biphenyl-4-yl-2-fluoro-malonamic acid (100 mg, 0.36 mmol) in DMF (2.0 mL) and the resulting mixture was stirred at the ambient temperature overnight. The mixture was then diluted with water and the product was extracted with ethyl acetate. The organics were washed with brine and concentrated to afford 51 mg (29.65%) of N-Biphenyl-4-yl-3-[4-(3-cyano-benzoyl)-piperazin-1-yl]-2-fluoro-3-oxo-propionamide. LCMS: 471.18 (M+1)$^+$, 95.1%, $^1$H NMR (DMSO-$d_6$): δ 8.3 (s, 1H), 7.8-7.3 (m, 13H), 4.3-3.7 (m, 3H), 3.7-3.3 (m, 5H).

Example 37

Synthesis of N-Biphenyl-4-yl-3-[4-(3-Fluoro-benzoyl)-piperazin-1-yl]-2-fluoro-3-oxo-propionamide

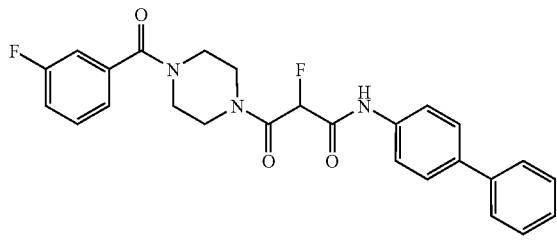

HOBt (29 mg, 0.219 mmol), DIPEA (71 mg, 0.54 mmol), EDCI.HCl (42 mg, 0.219 mmol) followed by 3-fluoro-phenyl)-piperazin-1-yl-methanone hydrochloride (53 mg, 0.219 mmol) were added to a stirred solution of N-biphenyl-4-yl-2-fluoro-malonamic acid (50 mg, 0.18 mmol) in DMF (1 mL) and the resulting mixture was stirred at ambient temperature overnight. The mixture was then diluted with water and the product was extracted with ethyl acetate. The organics were washed with brine and concentrated to afford 25 mg (29%) N-biphenyl-4-yl-3-[4-(3-fluoro-benzoyl)-piperazin-1-yl]-2-fluoro-3-oxo-propionamide. LCMS: 464.17 (M+1)$^+$, 90.15%, $^1$H NMR (CDCl$_3$): δ 8.2 (bs, 1H), 7.7-7.3 (m, 10H), 7.2-7.0 (m, 3H), 6.0-5.6 (m, 1H), 4.3 (m, 2H), 3.8-3.5 (m, 6H).

Synthesis of 2-Methyl-malonic acid monomethyl ester

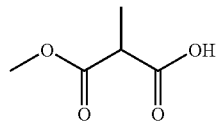

KOH (386 mg, 6.88 mmol) was added to a solution 2-methyl-malonic acid diethyl ester (1 g, 5.74 mmol) in methanol (7 mL). The resulting mixture was stirred overnight at ambient temperature then concentrated. The resulting residue was diluted with water, acidified with conc. HCl and the product was extracted with dichloromethane. The organic layer was dried over sodium sulfate and concentrated under reduced pressure to afford 360 mg (47%) of 2-methyl-malonic acid monomethyl ester Synthesis of N-Biphenyl-4-yl-2-Methyl-malonamic acid methyl ester

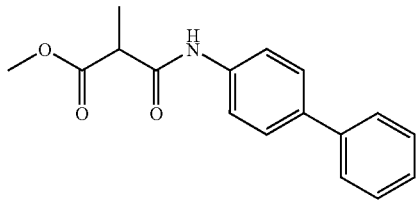

HOBt (245 mg, 1.8 mmol), DMAP (370 mg, 3.0 mmol), EDCI.HCl (348 mg, 1.8 mmol) followed by biphenyl-4-ylamine (307 mg, 1.8 mmol) were added to a stirred solution of 2-methyl-malonic acid monomethyl ester (200 mg, 1.5 mmol) in DMF (3 mL) and the resulting mixture was stirred at ambient temperature overnight. The reaction mixture was then diluted with water and the product was extracted with ethyl acetate. The ethyl acetate layer was washed with brine solution and concentrated under reduced pressure to afford 330 mg (77%) of N-biphenyl-4-yl-2-Methyl-malonamic acid methyl ester.

Synthesis of N-Biphenyl-4-yl-2-Methyl-malonamic acid

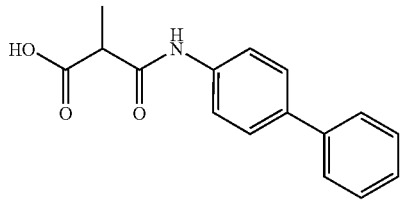

LiOH.H$_2$O (73 mg, 1.7 mmol) was added to a solution of N-biphenyl-4-yl-2-methyl-malonamic acid methyl ester (330 mg, 1.16 mmol) in a mixture of methanol (1.75 mL), THF (10 mL) and H$_2$O (1 mL). The resulting mixture was stirred for 2 hours at ambient temperature then concentrated. The residue was diluted with water, acidified with conc. HCl. The resulting precipitate was isolated by filtration and dried to afford 260 mg (83%) of N-biphenyl-4-yl-2-methyl-malonamic acid.

Example 38

Synthesis of N-Biphenyl-4-yl-3-[4-(2-bromo-benzoyl)-piperazin-1-yl]-2-methyl-3-oxo-propionamide

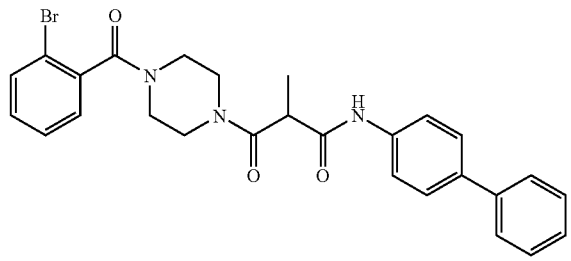

HOBt (60 mg, 0.44 mmol), DIPEA (140 mg, 1.1 mmol), EDCI.HCl (85 mg, 0.44 mmol) followed by (2-bromo-phenyl)-piperazin-1-yl-methanone hydrochloride (136 mg, 0.44 mmol), were added to a stirred solution of N-biphenyl-4-yl-2-methyl-malonamic acid (100 mg, 0.37 mmol) in DMF (2.0 mL). The resulting mixture was stirred at ambient temperature overnight then diluted with water. The product was extracted with ethyl acetate. The ethyl acetate layer was washed with brine and concentrated under reduced pressure to afford 140 mg (73%) of N-biphenyl-4-yl-3-[4-(2-bromo-benzoyl)-piperazin-1-yl]-2-methyl-3-oxo-propionamide. LCMS: 520.12 (M+1)$^+$, 97.32%, $^1$H NMR (DMSO-d$_6$): δ 10.2 (d, 1H), 7.8-7.3 (m, 13H), 4.0-3.4 (m, 7H), 3.2-3.0 (m, 2H), 1.3 (m, 3H).

Synthesis of N-Biphenyl-4-yl-formamide

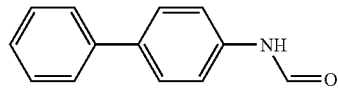

A mixture of biphenyl-4-ylamine (100 mg, 0.59 mmol) and ethylformate (1 mL) was stirred at reflux temperature for 1 hr. After the completion of the reaction, the reaction mixture was quenched with cold water. The precipitate was filtered to afford 100 mg (86.2% Yield) of N-biphenyl-4-yl-formamide as the required product.

Synthesis of Biphenyl-4-yl-methyl-amine

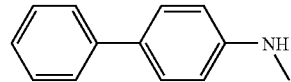

LAH (96 mg, 2.5 mmol) was added portionwise to a cold (at 0° C.) solution of N-biphenyl-4-yl-formamide (100 mg, 0.5 mmol) in THF (2 mL) and the stirring was continued at the same temperature for 30 minutes. After completion of the reaction, the reaction mixture was quenched with 3% aq NaOH solution, the precipitate obtained was filtered, the filtrate was collected was concentrated under reduced pressure to get a residue. The residue was diluted with ethyl acetate, the organic layer was washed with brine solution and dried over sodium sulfate. The organic layer was concentrated under reduced pressure to afford 85 mg (91.39% Yield) of biphenyl-4-yl-methyl-amine.

Synthesis of N-Biphenyl-4-yl-N-methyl-malonamic acid ethyl ester

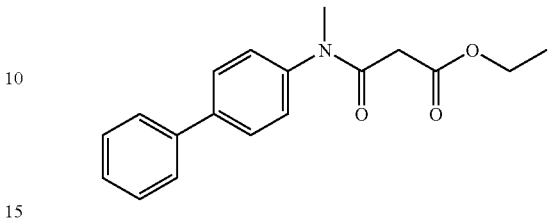

A solution of (400 mg, 2.26 mmol) and mono ethylmalonylchloride (375 mg, 2.49 mmol) was stirred at ambient temperature for 1 hr. The mixture was diluted with water (5 mL) and extracted with DCM. The organic layer was washed with brine solution, dried over Na$_2$SO$_4$, and concentrated to afford 116 mg (85.29% Yield) of N-biphenyl-4-yl-N-methyl-malonamic acid ethyl ester.

Synthesis of N-Biphenyl-4-yl-N-methyl-malonamic acid

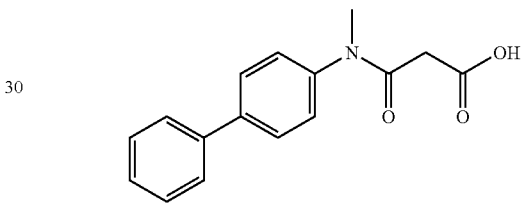

LiOH.H$_2$O (25 mg, 0.58 mmol) was added to a solution of N-biphenyl-4-yl-N-methyl-malonamic acid ethyl ester (116 mg, 0.39 mmol) in a mixture of Methanol (0.6 mL), THF (1.5 mL) and H$_2$O (0.4 mL). The resulting mixture was stirred at ambient temperature for 2 hrs. The reaction mixture was concentrated to get a residue. The residue was diluted with water, acidified with conc. HCl. The precipitate was collected and dried to afford 100 mg (95.24%) of N-biphenyl-4-yl-N-methyl-malonamic acid

Example 39

Synthesis of N-Biphenyl-4-yl-3-[4-(2-bromo-benzoyl)-piperazin-1-yl]-N-methyl-3-oxo-propionamide

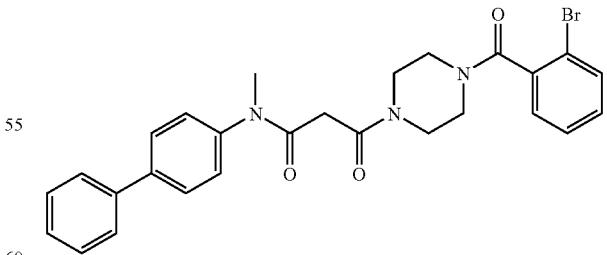

DIPEA (140 mg, 1.1 mmol) was added to a stirred solution of N-biphenyl-4-yl-N-methyl-malonamic acid (100 mg, 0.37 mmol) in DMF (2.0 mL) followed by HOBt (60 mg, 0.44 mmol) and EDCI.HCl (85 mg, 0.44 mmol). After 2 minutes of stirring, (2-bromo-phenyl)-piperazin-1-yl-methanone hydrochloride (136 mg, 0.44 mmol) was added and stirring was continued at ambient temperature overnight. The reaction mixture was diluted with water, extracted with ethyl acetate, washed with brine and concentrated under reduced pressure to get the residue. Purification by column chromatography, (using silica gel 60-120, 100% EtOAc as eluent) to afford 14.8 mg (12.95%) of 1-[4-(2-bromo-benzoyl)-piperazine-1-carbonyl]-cyclopropanecarboxylic acid biphenyl-4-ylamide. LC/MS [M+H]+: 520.12, 89.73%. $^1$H NMR (300 MHz, CDCl$_3$): δ 7.7-7.3 (m, 2H), 7.3-7.2 (m, 2H), 4.0-3.6 (m, 5H), 3.58-3.4 (m, 5H), 3.4-3.2 (m, 3H).

Synthesis of N-(3-Phenyl-isoxazol-5-yl)-malonamic acid ethyl ester

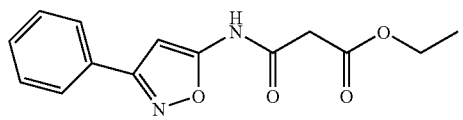

A solution of 3-phenyl-isoxazol-5-ylamine (500 mg, 0.31 mmol) and mono-ethyl malonyl chloride (56 mg, 0.37 mmol) in dichloromethane (2 mL) was stirred at ambient temperature overnight. The mixture was diluted with water and extracted with dichloromethane. The dichloromethane layer was washed with saturated sodium bicarbonate solution, followed by brine, dried over Na$_2$SO$_4$, concentrated to afford 78 mg (92.85% Yield) of N-(3-phenyl-isoxazol-5-yl)-malonamic acid ethyl ester.

Synthesis of N-(3-phenyl-isoxazol-5-yl)-malonamic acid

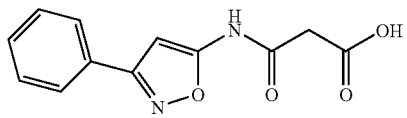

NaOH (57 mg, 1.4 mmol) was added to a stirred solution of N-(3-phenyl-isoxazol-5-yl)-malonamic acid ethyl ester (78 mg, 0.28 mmol) in a mixture of THF (12 mL) and H$_2$O (12 mL) and stirring was continued at ambient temperature overnight. The reaction mixture was concentrated. The residue was diluted with water, washed with diethyl ether, acidified with concentrated HCl. The precipitate was filtered to afford 45 mg (64.28% Yield) of N-(3-phenyl-isoxazol-5-yl)-malonamic acid.

Example 40

Synthesis of 3-[4-(2-Bromo-benzoyl)-piperazin-1-yl]-3-oxo-N-(3-phenyl-isoxazol-5-yl)-propionamide

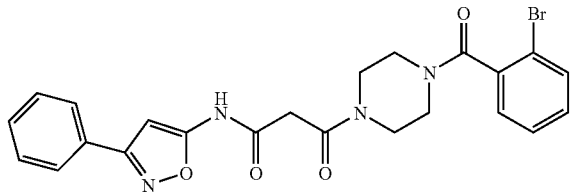

DIPEA (69.2 mg, 0.55 mmol) was added to a stirred solution of N-(3-phenyl-isoxazol-5-yl)-malonamic acid (45 mg, 0.18 mmol) in DMF (2 mL) followed by HOBt (29 mg, 0.22 mmol). After 2 minutes of stirring, (2-bromo-phenyl)-piperazin-1-yl-methanone hydrochloride (67 mg, 0.22 mmol) was added and stirring was continued at ambient temperature overnight. The reaction mixture was diluted with water and extracted with ethyl acetate. The organic layer was washed with brine solution, dried over Na$_2$SO$_4$ and concentrated to afford 38.9 mg (43.22% Yield) of 3-[4-(2-bromo-benzoyl)-piperazin-1-yl]-3-oxo-N-(3-phenyl-isoxazol-5-yl)-propionamide. LC/MS [M+1]+: 497.07, 97.0%. $^1$H NMR: (300 MHz, DMSO-d$_6$): δ 11.8 (bs, 1H), 7.92-7.8 (m, 2H), 7.5 (d, 1H), 7.6-7.3 (m, 6H), 6.8-6.7 (d, 1H), 3.8-3.4 (m, 8H), 3.24-3.04 (m, 2H).

Example 41

Synthesis of N-Biphenyl-4-yl-3-(4-cyclohexanecarbonyl-piperazin-1-yl)-3-oxo-propionamide

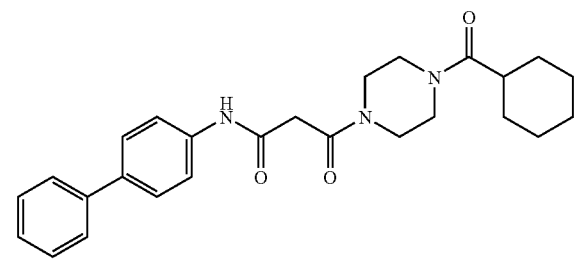

DIPEA (182 mg, 1.4 mmol) was added to a stirred solution of cyclohexane carboxylic acid (60 mg, 0.46 mmol) in DMF (2 mL) followed by HOBt (76 mg, 0.56 mmol) and EDCI.HCl (107 mg, 0.56 mmol). After 2 minutes of stirring, N-biphenyl-4-yl-3-oxo-3-piperazin-1-yl-propionamide hydrochloride (53 mg, 0.219 mmol) was added and stirring was continued at ambient temperature overnight. The reaction mixture was diluted with water, extracted with ethyl acetate, washed with brine and concentrated under reduced pressure to afford 48 mg (23.76%) of N-biphenyl-4-yl-3-[4-(3-fluoro-benzoyl)-piperazin-1-yl]-2-fluoro-3-oxo-propionamide. LC/MS [M+H]+: 434.24, 90.15%. $^1$H NMR (300 MHz, DMSO-d$_6$): δ10.2 (s, 1H), 7.74-7.58 (m, 6H), 7.5-7.4 (m, 2H), 7.4-7.3 (m, 1H), 3.6-3.5 (m, 9H), 2.6 (m, 1H), 1.7-1.6 (m, 5H), 1.4-1.2 (m, 6H).

Synthesis of 4-(2-Bromo-benzoyl)-[1,4]diazepane-1-carboxylic acid tert-butyl ester

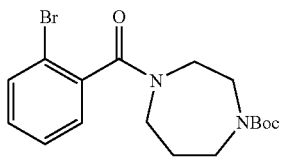

DIPEA (460 mg, 0.63 mL, 3.68 mmol) was added dropwise to 2-bromo-benzoic acid (370 mg, 1.84 mmol) in DMF (4 mL). This was followed by the addition of EDCI (423 mg, 2.2 mmol) and HOBT (298 mg, 2.2 mmol). After 2 minutes of stirring, [1,4]diazepane-1-carboxylic acid tert-butyl ester (150 mg, 0.47 mmol) was added. The resulting mixture was stirred at room temperature overnight. Cold water was then added and extracted with ethyl acetate. The organic layer was washed with brine, dried over Na$_2$SO$_4$, and concentrated under reduced pressure to afford 500 mg (71.12% yield) of 4-(2-bromo-benzoyl)-[1,4]diazepane-1-carboxylic acid tert-butyl ester.

Synthesis of
(2-Bromo-phenyl)-[1,4]diazepan-1-yl-methanone hydrochloride

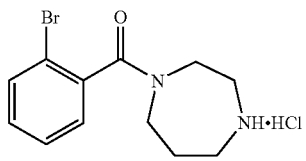

A solution of 4-(2-bromo-benzoyl)-[1,4]diazepane-1-carboxylic acid tert-butyl ester (500 mg, 1.3 mmol) in 1,4-dioxane.HCl (3 mL) was stirred at 0° C. for 30 minutes. The reaction was monitored by TLC (10% MeOH in CHCl$_3$). The reaction mixture was concentrated under reduced pressure to get a solid, which was washed with ether and dried to afford 400 mg (95.69% Yield) of (2-bromo-phenyl)-[1,4]diazepan-1-yl-methanone hydrochloride.

Example 42

Synthesis of N-Biphenyl-4-yl-3-[4-(2-bromo-benzoyl)-[1,4]diazepan-1-yl]-3-oxo-propionamide

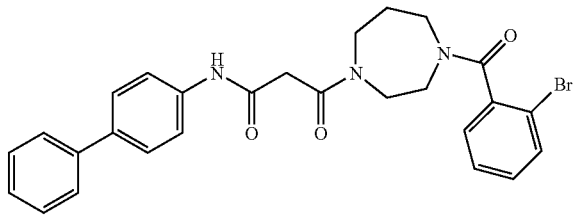

DIPEA (146 mg, 0.2 mL, 1.17 mmol) was added dropwise to N-biphenyl-4-yl-malonamic acid (100 mg, 0.39 mmol) in DMF (2 mL) followed by EDCI (90 mg, 0.47 mmol) and HOBT (63 mg, 0.47 mmol). After 2 minutes, (2-bromo-phenyl)-[1,4]diazepan-1-yl-methanone hydrochloride (150 mg, 0.47 mmol) was added and stirring was continued at room temperature overnight. Cold water was then added and extracted with ethyl acetate. The organic layer was washed with brine, dried over Na$_2$SO$_4$, and concentrated under reduced pressure to afford 110 mg (54.18% yield) of N-biphenyl-4-yl-3-[4-(2-bromo-benzoyl)-[1,4]diazepan-1-yl]-3-oxo-propionamide. LC/MS [M+H]$^+$: 520.12, 96.67%. $^1$H NMR (300 MHz, DMSO-d$_6$): δ 10.3-10.2 (m, 1H), 7.8-6.7 (m, 13H), 4.1-3.4 (m, 9H), 3.3-3.0 (m, 2H), 2.0-1.8 (m, 1H), 1.7-1.5 (m, 1H).

Synthesis of
N-[5-(4-Fluoro-phenyl)-isoxazol-3-yl]-malonamic acid ethyl ester

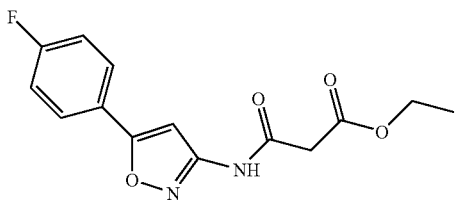

Diisopropyl carbodiimide (0.07 mL, 0.45 mmol) and 5-(4-fluoro-phenyl)-isoxazol-3-ylamine (67 mg, 0.037 mmol) were added to a stirred solution of malonic acid monoethyl ester (50 mg, 0.37 mmol) in THF (1 mL) and stirring was continued at reflux temperature for 4 hrs. The mixture was concentrated under reduced pressure. The residue obtained was diluted with ethyl acetate and washed with water, followed by brine solution. The organic layer collected was dried over Na$_2$SO$_4$ and concentrated under reduced pressure to afford 90 mg (81.8% Yield) of N-[5-(4-fluoro-phenyl)-isoxazol-3-yl]-malonamic acid ethyl ester.

Synthesis of
N-[5-(4-Fluoro-phenyl)-isoxazol-3-yl]-malonamic acid

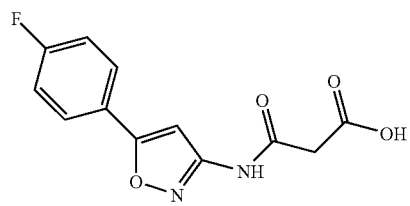

NaOH (34 mg, 8.5 mmol) was added to a solution of N-[5-(4-fluoro-phenyl)-isoxazol-3-yl]-malonamic acid ethyl ester (292 mg, 1.0 mmol) in the mixture of THF (13 mL) and H$_2$O (13 mL) and stirred for 1 hr at room temperature. The reaction mixture was concentrated and the obtained residue was diluted with water, acidified with concentrated HCl, and extracted with ethyl acetate. The ethyl acetate layer was washed with brine, dried over Na$_2$SO$_4$ and concentrated to afford 40 mg (90.9% Yield) of N-[5-(4-fluoro-phenyl)-isoxazol-3-yl]-malonamic acid.

Example 43

Synthesis of 3-[4-(2-Bromo-benzoyl)-piperazin-1-yl]-N-[5-(4-fluoro-phenyl)-isoxazol-3-yl]-3-oxo-propionamide

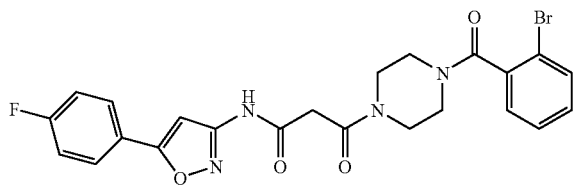

DIPEA (57 mg, 0.078 mL, 0.45 mmol) was added dropwise to N-[5-(4-fluoro-phenyl)-isoxazol-3-yl]-malonamic acid (40 mg, 0.15 mmol) in DMF (2 mL) followed by EDCI (35 mg, 0.18 mmol) and HOBT (24 mg, 0.18 mmol). After 2 minutes, (2-bromo-phenyl)-piperazin-1-yl-methanone hydrochloride (55 mg, 0.18 mmol) was added and stirring was continued at room temperature overnight. The reaction mixture was quenched with cold water and was then extracted with ethyl acetate, washed with brine, dried over Na$_2$SO$_4$, and concentrated under reduced pressure. Purification by preparative HPLC afforded 22 mg (28.27% yield) of 3-[4-(2-bromo-benzoyl)-piperazin-1-yl]-N-[5-(4-fluoro-phenyl)-isoxazol-3-yl]-3-oxo-propionamide. LC/MS [M+H]$^+$: 515.07, 96.02%. $^1$H NMR (300 MHz, DMSO-d$_6$): δ 11.4-

11.2 (m, 1H), 7.8 (m, 2H), 7.6 (d, 1H), 7.4-7.2 (m, 5H), 7.1 (t, 2H), 6.6 (d, 1H), 4.1-3.9 (m, 2H), 3.8-3.2 (m, 10H).

Example 44

Synthesis of 3-[4-(2-Bromo-benzoyl)-piperazin-1-yl]-3-oxo-N-(4-pyridin-3-yl-phenyl)-propionamide

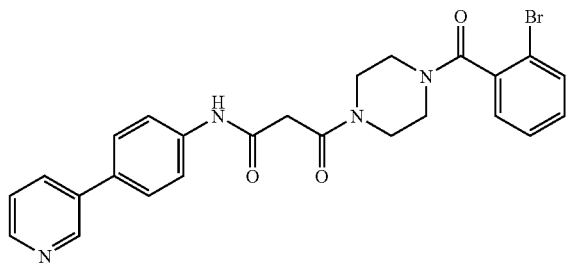

DMAP (68 mg, 0.56 mmol) was added to 3-[4-(2-bromo-benzoyl)-piperazin-1-yl]-3-oxo-propionic acid (100 mg, 0.28 mmol) in DMF (2 mL) followed by EDCI (64 mg, 0.33 mmol) and HOBT (45 mg, 0.33 mmol). After 2 minutes, 4-pyridin-3-yl-phenylamine (55 mg, 0.18 mmol) was added and it was stirred at room temperature overnight. Cold water was then added and the reaction mixture was extracted with ethyl acetate. The organic layer was washed with brine, dried over $Na_2SO_4$, and concentrated under reduced pressure to afford 55 mg (38.73% yield) of 3-[4-(2-bromo-benzoyl)-piperazin-1-yl]-3-oxo-N-(4-pyridin-3-yl-phenyl)-propionamide. LC/MS [M+H]$^+$: 507.1, 90.55%. $^1$H NMR (300 MHz, DMSO-$d_6$): δ 10.25 (d, 1H), 8.9 (bt, 1H), 8.5 (d, 1H), 8.1-8.0 (m, 1H), 7.7 (d, 5H), 7.52-7.3 (m, 4H), 3.8-3.46 (m, 8H), 3.2 (bt, 1H), 3.1 (bt, 1H).

Synthesis of 4-Nitro-1-phenyl-1H-pyrazole

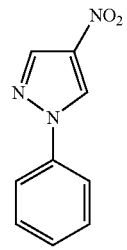

1-Phenyl-1H-pyrazole (500 mg, 3.4 mmol) was added to a cold mixture (−10° C.) of acetic anhydride (2.6 mL) and conc. $HNO_3$ (0.3 mL) and stirring was continued at ambient temperature for 4 hrs. The reaction mixture quenched with cold water and filtered. Isolation of the filter cake afforded 240 mg (36.58% Yield) of 4-nitro-1-phenyl-1H-pyrazole.

Synthesis of 4-Amino-1-phenyl-1H-pyrazole

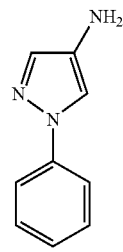

10% Pd/C (25 mg) was added to a stirred solution of 4-nitro-1-phenyl-1H-pyrazole (240 mg, 1.2 mmol) in a mixture of MeOH (2.5 mL) and EtOAc (2.5 mL) and stirred under $H_2$ atmosphere overnight. The reaction mixture was filtered through celite and the filtrate so obtained was concentrated under reduced pressure to afford 140 mg (69365% Yield) of 4-amino-1-phenyl-1H-pyrazole.

Example 45

Synthesis of 3-[4-(2-Bromo-benzoyl)-piperazin-1-yl]-3-oxo-N-(1-phenyl-1H-pyrazol-4-yl)-propionamide

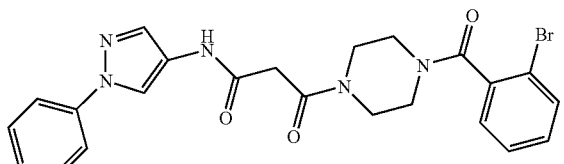

DMAP (68 mg, 0.56 mmol) was added to 3-[4-(2-bromo-benzoyl)-piperazin-1-yl]-3-oxo-propionic acid (100 mg, 0.28 mmol) in DMF (2 mL) followed by EDCI (64 mg, 0.33 mmol) and HOBT (45 mg, 0.33 mmol). After 2 minutes, 1-phenyl-1H-pyrazol-4-ylamine (54 mg, 0.33 mmol) was added and stirring was continued at room temperature overnight. Cold water was then added and the mixture was extracted with ethyl acetate. The organic layer was washed with brine, dried over $Na_2SO_4$, and concentrated under reduced pressure to afford 50 mg (35.97% yield) of 3-[4-(2-bromo-benzoyl)-piperazin-1-yl]-3-oxo-N-(1-phenyl-1H-pyrazol-4-yl)-propionamide. LC/MS [M+H]$^+$: 596.09, 87.79%. $^1$H NMR (300 MHz, DMSO-$d_6$): δ 10.4 (d, 1H), 8.5 (d, 1H), 7.84-7.64 (m, 4H), 7.54-7.2 (m, 5H), 4.0-3.8 (m, 7H), 3.2-3.1 (m, 2H).

Example 46

Synthesis of N-Biphenyl-4-yl-3-oxo-3-[4-(3,4,5-trifluoro-benzyl)-piperazin-1-yl]-propionamide

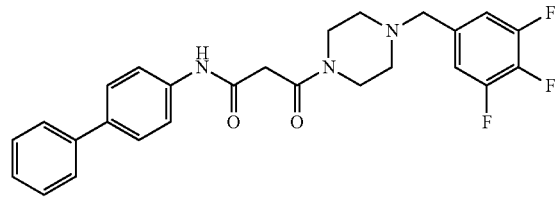

DIPEA (140 mg, 0.193 mL, 1.1 mmol) was added to N-biphenyl-4-yl-malonamic acid (95 mg, 0.37 mmol) in DMF (2 mL) followed by EDCI (86 mg, 0.44 mmol) and HOBT (50 mg, 0.44 mmol). After 2 minutes, 1-(3,4,5-trifluoro-benzyl)-piperazine hydrochloride (119 mg, 0.44 mmol), which was prepared according to method I using commercial 2,3,4-trifluoromethyl bromide, was added and stirring was continued at room temperature overnight. Cold water was then added and extracted with ethyl acetate. The organic layer was washed with brine, dried over $Na_2SO_4$, and concentrated under reduced pressure. The residue obtained was purified by column chromatography (using 60-120 silica gel and 1% MeOH in $CHCl_3$ as eluent) to afford 40 mg (23.12% yield) of N-biphenyl-4-yl-3-oxo-3-[4-(3,4,5-trifluoro-benzyl)-piperazin-1-yl]-propionamide. LC/MS [M+H]$^+$: 568.18, 98.56%. $^1$H NMR (300 MHz, DMSO-$d_6$): δ 10.2 (s, 1H), 7.7-7.6 (m, 6H), 7.5-7.4 (m, 2H), 7.38-7.2 (m, 3H), 3.6-3.4 (m, 8H), 2.5-2.3 (m, 4H).

Synthesis of N-(4-Bromo-phenyl)-acetamide

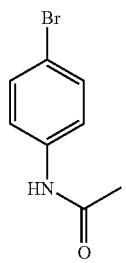

Pyridine (551 mg, 5.8 mmol) and acetic anhydride (650 mg, 0.6 mL, 6.4 mmol) were added to a cold solution (at 0° C.) of 4-bromo-phenylamine (1 g, 5.8 mmol) in DCM (10 mL) and stirring was continued at ambient temperature for 2 hrs. The reaction mixture was diluted with DCM and washed the organic layer with water followed by brine solution. The organic layer collected was dried over sodium sulfate and concentrated under reduced pressure to afford 900 mg (69.5% yield) of N-(4-bromo-phenyl)-acetamide.

Synthesis of N-(4-Thiophen-3-yl-phenyl)-acetamide

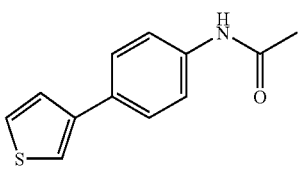

A mixture of toluene (7.5 mL) and water (3 mL) was degassed with argon for 10 min, to which sodium carbonate (297 mg, 2.8 mmol) was added and the mixture was further degassed with argon for 5 min. Thiophene-3-boronic acid (215 mg, 1.68 mmol) and N-(4-bromo-phenyl)-acetamide (300 mg, 2.27 mmol) were added and the mixture was degassed with argon for another 10 min. To the above resulting mixture was added tetrakispalladium triphenylphosphine (161 mg, 0.14 mmol) and the mixture was degassed with argon for another 10 min. The resulting reaction mixture was heated to reflux for 3 hrs. After completion, the reaction mixture was diluted with ethyl acetate and washed with water followed by brine solution. The ethyl acetate layer collected was dried over sodium sulphate and concentrated under reduced pressure. Purification by column chromatography, (using silica gel 60-120 and 35% ethyl acetate in hexane as eluent) afforded 193 mg (63.44% Yield) of N-(4-thiophen-3-yl-phenyl)-acetamide.

Synthesis of 4-Thiophen-3-yl-phenylamine

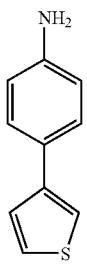

A mixture of N-(4-thiophen-3-yl-phenyl)-acetamide (90 mg, 0.41 mmol), NaOH (133 mg, 3.3 mmol), MeOH (2 mL) and water (7 mL) was heated to reflux for 12 hr. After completion of the reaction, the reaction mixture was diluted with water, extracted with ethyl acetate, washed with brine solution and dried over sodium sulphate. The organic layer collected was concentrated under reduced pressure to afford 83 mg (crude) of 4-thiophen-3-yl-phenylamine.

Example 47

Synthesis of 3-[4-(2-Bromo-benzoyl)-piperazin-1-yl]-3-oxo-N-(4-thiophen-3-yl-phenyl)-propionamide

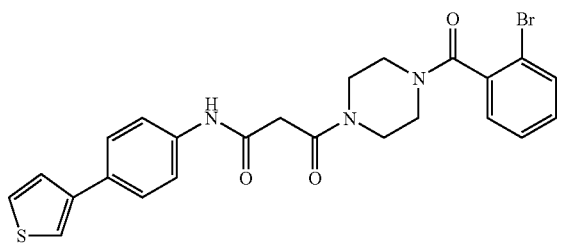

DMAP (104 mg, 0.85 mmol) was added to 3-[4-(2-bromo-benzoyl)-piperazin-1-yl]-3-oxo-propionic acid (167 mg, 0.47 mmol) in DMF (2 mL) followed by EDCI (90 mg, 0.47 mmol) and HOBT (63 mg, 0.47 mmol). After 2 minutes, 4-thiophen-3-yl-phenylamine (75 mg, 0.43 mmol) was added and stirring was continued at room temperature overnight. Cold water was added and the formed precipitate was collected. Purification by preparative HPLC afforded 42 mg (19.2% yield) of 3-[4-(2-bromo-benzoyl)-piperazin-1-yl]-3-oxo-N-(4-thiophen-3-yl-phenyl)-propionamide. LC/MS [M+H]$^+$: 512.06, 93.02%. $^1$H NMR (300 MHz, CDCl$_3$): δ 9.6 (d, 1H), 7.85-7.5 (m, 5H), 7.46-7.34 (m, 4H), 7.34-7.26 (m, 2H), 4.09-3.9 (m, 2H), 3.82-3.64 (m, 4H), 3.58-3.52 (s, 1H), 3.5-3.44 (s, 1H), 3.42-3.32 (m, 1H), 3.3-3.18 (m, 1H).

Example 48

Synthesis of 3-[4-(2-Bromo-benzoyl)-piperazin-1-yl]-3-oxo-N-(5-phenyl-pyridin-2-yl)-propionamide

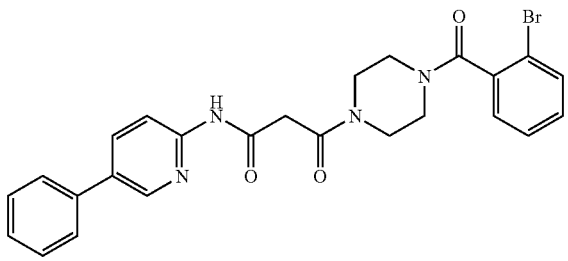

DMAP (137 mg, 1.1 mmol) was added to 3-[4-(2-bromo-benzoyl)-piperazin-1-yl]-3-oxo-propionic acid (200 mg, 0.56 mmol) in DMF (2 mL) followed by EDCI (129 mg, 0.67 mmol) and HOBT (91 mg, 0.67 mmol). After 2 minutes, 5-phenyl-pyridin-2-ylamine (115 mg, 0.67 mmol) was added and stirring was continued at room temperature overnight. Cold water was then added and it was extracted with ethyl acetate. The organic layer was washed with brine, dried over Na$_2$SO$_4$, and concentrated under reduced pressure to afford 77 mg (27% yield) of 3-[4-(2-bromo-benzoyl)-piperazin-1-yl]-3-oxo-N-(5-phenyl-pyridin-2-yl)-propionamide. LC/MS [M+H]$^+$: 507.1, 97.03%. $^1$H NMR (300 MHz, DMSO-d$_6$): δ

10.8 (d, 1H), 8.7-8.6 (bs, 1H), 8.2-8.06 (m, 2H), 7.76-7.64 (m, 3H), 7.54-7.34 (m, 6H), 3.8-3.4 (m, 8H), 3.24-3.1 (m, 2H).

Example 49

Synthesis and purification of 3-Oxo-N-(5-phenyl-pyridin-2-yl)-3-[4-(3,4,5-trifluoro-benzoyl)-piperazin-1-yl]-propionamide

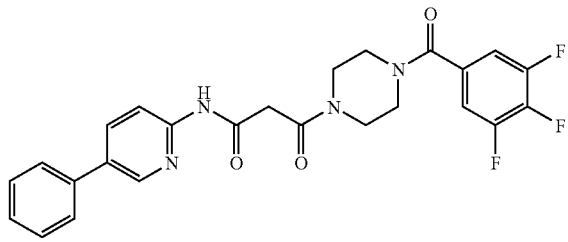

DIPEA (453 mg, 3.51 mmol) was added to N-(5-phenyl-pyridin-2-yl)-malonamic acid (300 mg, 1.17 mmol), which was prepared following the synthetic route described in method II, in DMF (3 mL) followed by EDCI (336 mg, 1.75 mmol) and HOBT (189 mg, 1.4 mmol). After 2 minutes, piperazin-1-yl-(3,4,5-trifluoro-phenyl)-methanone hydrochloride (328 mg, 1.17 mmol) was added and stirring was continued at room temperature overnight. Cold water was then added and extracted with ethyl acetate. The organic layer was washed with brine, dried over $Na_2SO_4$, and concentrated under reduced pressure. Purification by preparative HPLC afforded 85 mg (15% yield) of 3-oxo-N-(5-phenyl-pyridin-2-yl)-3-[4-(3,4,5-trifluoro-benzoyl)-piperazin-1-yl]-propionamide. LC/S [M+H]$^+$: 483.16, 97.03%. $^1$H NMR (300 MHz, DMSO-$d_6$): δ 10.7 (s, 1H), 8.7 (s, 1H), 8.1 (s, 2H), 7.7 (d, 2H), 7.5 (m, 4H), 7.4 (m, 1H), 3.7-3.1 (bs, 2H), 3.6-3.2 (m, 8H).

The entire disclosures of all applications, patents and publications, cited above and below, are hereby incorporated by reference.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:

1. A compound selected from the group consisting of:
N-Biphenyl-4-yl-3-oxo-3-[4-(2-trifluoromethyl-benzoyl)-piperazin-1-yl]-propionamide,
N-Biphenyl-4-yl-3-[4-(2,5-dichloro-benzoyl)-piperazin-1-yl]-3-oxo-propionamide,
N-Biphenyl-4-yl-3-[4-(5-fluoro-2-trifluoromethyl-benzoyl)-piperazin-1-yl]-3-oxo-propionamide,
N-Biphenyl-4-yl-3-[4-(4-chloro-2,5-difluoro-benzoyl)-piperazin-1-yl]-3-oxo-propionamide,
N-Biphenyl-4-yl-3-[4-(2-methyl-benzoyl)-piperazin-1-yl]-3-oxo-propionamide,
N-Biphenyl-4-yl-3-[4-(2,5-difluoro-benzoyl)-piperazin-1-yl]-3-oxo-propionamide,
N-Biphenyl-4-yl-3-[4-(2-bromo-5-fluoro-benzoyl)-piperazin-1-yl]-3-oxo-propionamide,
N-Biphenyl-4-yl-3-oxo-3-[4-(3,4,5-trifluoro-benzoyl)-piperazin-1-yl]-propionamide,
N-Biphenyl-4-yl-3-[4-(2-chloro-5-trifluoromethyl-benzoyl)-piperazin-1-yl]-3-oxo-propionamide, and
N-Biphenyl-4-yl-3-[4-(2-bromo-benzoyl)-piperazin-1-yl]-3-oxo-propionamide,
or pharmaceutically acceptable salts thereof.

2. A compound selected from the group consisting of:
N-Biphenyl-4-yl-3-[4-(2,4-dichloro-5-fluoro-benzoyl)-piperazin-1-yl]-3-oxo-propionamide,
N-Biphenyl-4-yl-3-[4-(2-fluoro-benzoyl)-piperazin-1-yl]-3-oxo-propionamide,
N-Biphenyl-4-yl-3-[4-(3-fluoro-benzoyl)-piperazin-1-yl]-3-oxo-propionamide,
N-Biphenyl-4-yl-3-[4-(4-fluoro-benzoyl)-piperazin-1-yl]-3-oxo-propionamide,
N-Biphenyl-4-yl-3-oxo-3-[4-(2-trifluoromethyl-benzyl)-piperazin-1-yl]-propionamide,
N-Biphenyl-4-yl-3-[4-(2-chloro-benzenesulfonyl)-piperazin-1-yl]-3-oxo-propionamide,
N-Biphenyl-3-yl-3-oxo-[4-(2-trifluoromethyl-benzoyl)-piperazin-1-yl]-propionamide,
3-oxo-N-(5-phenyl-pyridin-2-yl)-3-[4-(2-trifluoromethyl-benzoyl)-piperazin-1-yl]-propionamide,
N-(4-[1,2,4]Oxadiazol-3-yl-phenyl)-3-oxo-3-[4-(2-trifluoromethyl-benzoyl)-piperazin-1-yl]-propionamide, and
N-[4-(5-Methyl-[1,3,4]oxadiazol-2-yl)-phenyl]-3-oxo-3-[4-(2-trifluoromethyl-benzoyl)-piperazin-1-yl]-propionamide,
or pharmaceutically acceptable salts thereof.

3. A compound selected from the group consisting of:
N-(6-Benzyloxy-pyridin-3-yl)-3-oxo-3-[4-(2-trifluoromethyl-benzoyl)-piperazin-1-yl]-propionamide,
3-Oxo-N-(2-oxo-2,3-dihydro-benzooxazol-5-yl)-3-[4-(2-trifluoromethyl-benzoyl)-piperazin-1-yl]-propionamide,
N-Methyl-4-{3-oxo-3-[4-(2-trifluoromethyl-benzoyl)-piperazin-1-yl]-propionylamino}-benzamide,
3-Oxo-N-(4-piperidin-1-yl-phenyl)-3-[4-(2-trifluoromethyl-benzoyl)-piperazin-1-yl]-propionamide
3-oxo-N-(6-phenyl-pyridin-3-yl)-3-[4-(2-trifluoromethyl-benzoyl)-piperazin-1-yl]-propionamide,
3-oxo-N-(4-phenyl-thiazol-2-yl)-3-[4-(2-trifluoromethyl-benzoyl)-piperazin-1-yl]-propionamide,
3-Oxo-N-(6-phenyl-pyridin-3-yl)-3-[4-(3,4,5-trifluoro-benzoyl)-piperazin-1-yl]-propionamide,
N-(4-[1,2,4]Oxadiazol-3-yl-phenyl)-3-oxo-3-[4-(3,4,5-trifluoro-benzoyl)-piperazin-1-yl]-propionamide,
3-oxo-N-(4-phenylamino-phenyl)-3-[4-(2-trifluoromethyl-benzoyl)-piperazin-1-yl]-propionamide, and
3-[4-(2-Bromo-benzoyl)-piperazin-1-yl]-3-oxo-N-(6-phenyl-pyridin-3-yl)-propionamide,
or pharmaceutically acceptable salts thereof.

4. A compound selected from the group consisting of:
3-[4-(2-Bromo-benzoyl)-piperazin-1-yl]-N-(4-[1,2,4]oxadiazol-3-yl-phenyl)-3-oxo-propionamide,
3-[4-(2-Bromo-benzoyl)-piperazin-1-yl]-N-(4-morpholin-4-yl-phenyl)-3-oxo-propionamide,
3-[4-(2-Bromo-benzoyl)-piperazin-1-yl]-3-oxo-N-[4-(2-oxo-2H-pyridin-1-yl)-phenyl]-propionamide,
1-[4-(2-Bromo-benzoyl)-piperazine-1-carbonyl]-cyclopropanecarboxylic acid biphenyl-4-ylamide,
N-Biphenyl-4-yl-3-[4-(2-bromo-benzoyl)-piperazin-1-yl]-2-fluoro-3-oxo-propionamide,
N-Biphenyl-4-yl-3-[4-(3-cyano-benzoyl)-piperazin-1-yl]-2-fluoro-3-oxo-propionamide, N-Biphenyl-4-yl-3-[4-(3-Fluoro-benzoyl)-piperazin-1-yl]-2-fluoro-3-oxo-propionamide,
N-Biphenyl-4-yl-3-[4-(2-bromo-benzoyl)-piperazin-1-yl]-2-methyl-3-oxo-propionamide,
N-Biphenyl-4-yl-3-[4-(2-bromo-benzoyl)-piperazin-1-yl]-N-methyl-3-oxo-propionamide, and
3-[4-(2-Bromo-benzoyl)-piperazin-1-yl]-3-oxo-N-(3-phenyl-isoxazol-5-yl)-propionamide,
or pharmaceutically acceptable salts thereof.

5. A compound selected from the group consisting of:
N-Biphenyl-4-yl-3-[4-(2-bromo-benzoyl)-[1,4]diazepan-1-yl]-3-oxo-propionamide,
3-[4-(2-Bromo-benzoyl)-piperazin-1-yl]-N-[5-(4-fluoro-phenyl)-isoxazol-3-yl]-3-oxo-propionamide,
3-[4-(2-Bromo-benzoyl)-piperazin-1-yl]-3-oxo-N-(4-pyridin-3-yl-phenyl)-propionamide,
3-[4-(2-Bromo-benzoyl)-piperazin-1-yl]-3-oxo-N-(1-phenyl-1H-pyrazol-4-yl)-propionamide,
N-Biphenyl-4-yl-3-oxo-3-[4-(3,4,5-trifluoro-benzyl)-piperazin-1-yl]-propionamide,
3-[4-(2-Bromo-benzoyl)-piperazin-1-yl]-3-oxo-N-(4-thiophen-3-yl-phenyl)-propionamide,
3-[4-(2-Bromo-benzoyl)-piperazin-1-yl]-3-oxo-N-(5-phenyl-pyridin-2-yl)-propionamide, and
3-oxo-N-(5-phenyl-pyridin-2-yl)-3-[4-(3,4,5-trifluoro-benzoyl)-piperazin-1-yl]-propionamide,
or pharmaceutically acceptable salts thereof.

6. A pharmaceutical composition comprising a compound of claim 1 and a pharmaceutically acceptable carrier.

7. A pharmaceutical composition comprising a compound of claim 2 and a pharmaceutically acceptable carrier.

8. A pharmaceutical composition comprising a compound of claim 3 and a pharmaceutically acceptable carrier.

9. A pharmaceutical composition comprising a compound of claim 4 and a pharmaceutically acceptable carrier.

10. A pharmaceutical composition comprising a compound of claim 5 and a pharmaceutically acceptable carrier.

* * * * *